United States Patent [19]

Okada et al.

[11] Patent Number: 5,547,817
[45] Date of Patent: Aug. 20, 1996

[54] PHOTOGRAPHIC PROCESSING USING A NOVEL CHELATING COMPLEX

[75] Inventors: Hisashi Okada; Tadashi Inaba; Ryo Suzuki; Hideaki Nomura, all of Kanagawa, Japan

[73] Assignee: Fuji Photo Film Co., Ltd., Kanagawa, Japan

[21] Appl. No.: 528,015

[22] Filed: Sep. 14, 1995

[30]   Foreign Application Priority Data

Oct. 20, 1994  [JP]  Japan .................................. 6-279793
May 25, 1995  [JP]  Japan .................................. 7-149761

[51] Int. Cl.$^6$ .................. G03C 7/00; G03C 5/18; G03C 5/26; G03C 5/44
[52] U.S. Cl. .................. 430/393; 430/372; 430/428; 430/430; 430/461; 430/463; 430/488; 430/490; 430/491
[58] Field of Search ..................... 430/372, 393, 430/428, 430, 448, 461, 463, 490, 491, 488

[56]     References Cited

U.S. PATENT DOCUMENTS 5,352,567  10/1994  Okada et al. ......................... 430/393

FOREIGN PATENT DOCUMENTS 3-192254  8/1991  Japan .
5-134364  5/1993  Japan .

Primary Examiner—Janet C. Baxter
Assistant Examiner—J. Pasterczyk
Attorney, Agent, or Firm—Sughrue, Mion, Zinn, Macpeak & Seas

[57]     ABSTRACT

Photographic processing using an additive represented by formula (I):

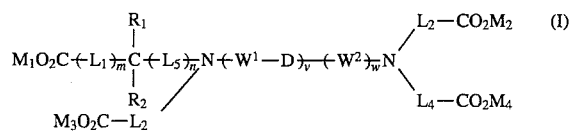

wherein $R_1$ is an aliphatic hydrocarbon group, an aryl group, or a heterocyclic ring group; $R_2$ is hydrogen, an aliphatic hydrocarbon group, an aryl group, or a heterocyclic ring group; $L_1, L_2, L_3, L_4$ and $L_5$ are independently an alkylene group; m and n are independently 0 or 1; $W^1$ and $W^2$ are independently an alkylene group, an arylene group, aralkylene group or a divalent nitrogen-containing heterocyclic ring group; D is a single bond, —O—, —S— or —N($R_w$), where $R_2$ is hydrogen, an aliphatic hydrocarbon group or an aryl group; v is 0 or an integer or from 1 to 3; w is an integer of from 1 to 3; and $M_1, M_2, M_3$ and $M_4$ are independently hydrogen or a cation.

6 Claims, No Drawings

PHOTOGRAPHIC PROCESSING USING A NOVEL CHELATING COMPLEX

FIELD OF THE INVENTION

This invention relates to a novel iron complex available as an oxidizing agent, particularly as an oxidizing agent for use in a field of silver halide photosensitive material, for example, available as a bleaching agent for use in bleaching or bleach-fixing a silver halide color photosensitive material.

This invention also relates to an additive for silver halide photography and a processing process using the same. More specifically, it relates to a novel bleaching agent used in a bleaching or bleach-fixing stage after color development and a novel chelating agent for masking metal ions harmful for photographic processing.

BACKGROUND OF THE INVENTION

Conventionally, iron complexes have been widely used for medical use, and in cosmetic preparations, photographs, information recording materials (magnetically recording materials, laser recording materials, etc.), copying materials (heat-sensitive materials and pressure-sensitive materials, etc.) and particularly have been used as an oxidizing agent utilized in the field of silver halide photosensitive material, for example, as a reducing agent for use in reducing processing of a silver halide photosensitive material and a bleaching agent for use in bleaching processing, in a large amount. An example of the iron complex which has be used as a bleaching agent in many times include ferric salt of ethylenediaminetetraacetic acid, but the bleaching ability thereof is not so high and is not enough when a rapid processing is required. On the other hand, red prussiate salt and ferric salt of 1,3-propanediaminetetraacetic acid are disclosed as iron complexes having a high bleaching ability, but due to their high oxidation-reduction electric potential, there is a tendency to accelerate the decomposition of co-existing compounds and, therefore, their applications have been restricted.

In addition, compounds comprising ethylenediamine-N,N'-diacetic acid-N,N'-dipropionic acid similar to the compound of the present invention have been known.

However, this complex has been found to possess the problem that its oxidation-reduction electic potential is changed by varying a pH level, and especially an oxidizing power is decreased at a high pH region.

Generally, a silver halide black-and-white photosensitive material after the exposure is processed through black-and-white development, fixation, water washing and any other processing stages, and a silver halide color photosensitive material (hereinafter referred to as "color photosensitive material") after the exposure is processed through color development, desilvering, water washing, stabilization and any other processing stages. A silver halide color reversal photosensitive material is processed after the exposure through black-and-white development, and after the reversal processing processed through processing stages such as color development, desilvering, water washing and stabilization.

In the color development, photosensitized silver halide grains are reduced to silver by a color developing agent and, at the same time, the formed oxidized product of the color developing agent is reacted with a coupler to form an image dye in the color developing stage. In the subsequent desilvering stage, the developed silver formed during the developing stage is oxidized (bleached) with a bleaching agent (oxidizing agent) having an oxidizing function to a silver salt, which is then removed from the photosensitive layer together with an unused silver halide, with a fixer which forms a soluble silver (fixation).

Concerning the bleaching and fixation, there are a case where a bleaching stage and a fixation stage are separately carried out and a case where they are carried out at the same time as a bleach-fixing stage. The details of these processing stages and compositions thereof are described in James, "The Theory of Photographic Process", 4th edition, (1977); Research Disclosure (RD) No. 17643, pages 28–29, RD No. 18716, page 651, from left column to right column, and RD No. 307105, pages 880–881, etc.

In addition to these basic processing stage, various supplemental stages are applied for the purpose of maintaining photographic and physical qualities of dye image, for the purpose of maintaining the stability of processing, etc. For example, water washing stage, stabilization stage, hardening stage, stopping stage, etc. can be mentioned.

In order to adjust gradation, etc. of a developed silver halide black-and-white photosensitive material, the material is processed with a reducing solution containing an oxidizing agent.

These processing stages are generally carried out by an automatic developing machine and the photographic processing is carried out at various locations from large scale developing centers which provide a large-size automatic developing machine, to photograph shops which provide in front of the shop a small-size automatic developing machine so-called "small-size laboratory" in recent years. This widens a service for rapid processing. However, ferric salt of ethylenediaminetetraacetic acid has, which has been conventionally used as a bleaching agent in a bleaching or bleach-fixing stage in the processing of a color photosensitive material, the basic problem of weak oxidizing power, in spite of making an improvement such as the use of a bleaching accelerator (e.g., the addition of a mercapto compound as described in U.S. Pat. No. 1,138,842), the object of rapid bleaching has not yet been attained.

As bleaching agents which attain rapid bleaching, red prussiate, iron chloride, bromates, etc. have been known. However, for red prussiate in terms of the problems associated with environmental safeguard, iron chloride in terms of inconvenience associated with handling such as metal corrosion, and bromates in terms of the problem associated with the instability of the solution, they cannot be widely used.

Consequently, it has been desired to provide a bleaching agent having good handing ability, free from the problems associated with the discharge of wasted liquid and attaining rapid bleaching. In recent years, ferric complex of 1,3-diaminopropanetetraacetic acid is disclosed as one which satisfies such requirements.

However, ferric complex of 1,3-diaminopropanetetraacetic acid has the problems in terms of ability that bleach fogging occurs accompanying with bleaching. As a process for reducing the bleach fogging, the addition of a buffer to the bleaching solution (e.g., JP-A-1-213657; the term "JP-A" used herein means Japanese unexamined patent publication). However, the level of the improvement is not sufficient and, particularly, in the color development carried out within three minutes, since a highly active developer is used, the generation of large bleach fogging still takes place.

When a processing solution comprising the ferric complex of 1,3-diaminopropanetetraacetic acid is used, there arise the problems that staining is increased during the storage after the processing, or when being continuously processed with the above processing solution there pose the problems that the desilvering properties are decreased in comparison with those at an initial continuous processing stage and that fogging takes place at an unexposed portion due to the mixing of the bleaching solution with the color developer.

Moreover, for carrying out the bleaching processing rapidly, a process using one bath (bleach-fixing bath) as a bleaching bath and a fixing bath has been known, but when the processing solution having a bleaching ability comprising ferric complex of 1,3-diaminopropanetetraacetic acid, ammonium thiophosphate, which is a fixer, is decomposed, thereby forming a precipitate to stain the surface of the photosensitive material and to cause the blockage of filter and poor desilvering.

On the hand, in accordance with the fact that the photographic processing is carried out at various locations from a large-scale developing centers which provide a large-size automatic developing machine to photograph shops which provide in front of the shop a small-size automatic developing machine so-called "small-size laboratory" in recent years, there is the problem that the processing ability of the processing solution in the above processing stage is decreased.

As one serious cause, mixing of the processing solution with metal ions can be mentioned. Various metal ions are mixed with the processing solution via various routes. For example, calcium, magnesium, and in some cases, iron ions are mixed with the processing solution through water for preparing the processing solution, and calcium contained in gelatine of the photosensitive material is mixed with the processing solution. Moreover, an iron chelate used in the processing solution is mixed with the developing solution, which is the pre-bath, by splashing the solution into the pre-bath, a solution having been impregnated in the film is carried over to carry over the ions contained in the pre-bath in some cases.

The influences of the mixed ions are different depending upon the types of ions and processing solutions.

Calcium and magnesium ions mixed with the developing solution are reacted with a carbonate generally used as a buffer to form a precipitate or sludge, causing the problems of blocking the circular filter of the automatic developing machine and staining of the film. The mixing of a transition metal ion such as iron ion with the developing solution causes the decomposition of parapheylanediamine type color developing agents and black developing agents such as hydroquinone and monolole and of preservatives such as hydroxylamines and sulfites, and the photographic properties are drastically deteriorated.

When a transition metal ion such as iron ion is mixed with a bleaching solution using hydrogen peroxide or a persulfate, also the stability of the solution is decreased, causing the problems associated with lacking in bleaching.

Also in the fixing solution, in the case of a fixing solution using a usual thiosulfate as a fixer, the mixing of a transition metal salt causes a drastic decrease in the stability, generating the muddiness in the solution and a sludge. As a result, due to the blockage of the filter of the automatic developing machine, an amount of flow circulated is decreased, the stability becomes lacking and processing staining is brought about on the film. Such phenomena in a fixing solution also take place in the washing water subsequent to the fixing solution, and particularly when an amount of washing water is decreased, an efficiency for exchanging the solution in the tank is decreased, which tends to cause the problems of the decomposition of a thiosulfate called sulfidation, and of the formation of a precipitate of the silver sulfide. These states often cause fatal staining on the surface of the film.

In a stabilizing solution prepared using hard water containing large amounts of calcium and magnesium, bacteria are generated taking these metals as nutrition resource, generating muddiness in the solution and causing film staining. In the case of mixing transition metal ions represented by iron ion, these ions remaining on the film change the storage ability for the worse.

As described above, the mixing of metal ions with processing solution causes various harmful effects and, thus, it has been strongly desired to provide an effective ion masking agent.

As means for solving these problems, a chelating agent which masks metal ions has been used. Examples include aminopolycarboxylic acids (e.g. ethylenediaminetetraacetic acid and diethylenetriaminepentaacetic acid) as described in JP-B-48-30496 (the term "JP-B" used herein means Japanese examined patent publication) and JP-B-44-30232, organic phosphonic acids as described in JP-A-56-97347, JP-B-56-39359 and West German Patent 2,227,639, phosphonocarboxylic acids as described in JP-A-52-102726, JP-A-53-42730, JP-A-54-121127, JP-A-55-126241, and JP-A-55-65956, as well as compounds described in JP-A-58-195845, JP-A-58-203440 and JP-B-53-40900.

As a compound having a skeleton similar to that of the compound of the present invention, ethylenediaminediacetic acid dipropionic acid as described in "Journal of American Chemical Society", Vol. 74, page 6288 (1952) or Vol.75, page 4814, can be mentioned.

Although some of these compounds have been put into a practical use, their abilities are not sufficient. For example, ethylenediaminetetraacetic acid has a large masking power, against calcium ion but when being added to a developer, it accelerates the decomposition of a developing agent or a preservative for developing agent in the presence of iron ion, and causes deterioration in photographic properties such as decreased image density, and increased fogging. For example, although an alkylidenediphosphonic acid has no such an adverse influence even in the presence of iron ion, it causes the trouble that solid substances (tar) occur in a processing solution prepared from hard water containing a large amount of calcium, and causes a trouble of a developing machine. As compounds which solve the problems seen in these two compounds at the some time, chelating agents are described in JP-5-66527. However, these compounds are difficult to maintain their abilities under severe conditions such as heightening a processing temperature and extending a residence time in a processing solution.

Ethylenediaminediacetic acid dipropionic acid having a skeleton similar to that of the compound of the present invention have a large variation in masking ability according to a change in pH, and in the case of changing the conditions for a processing solution, their abilities are sometimes not in a sufficient level. Particularity, in an alkaline developing bath, since its iron ion masking power is originally low, an excess amount of this compound is required to be added, which is not preferable in terms of photographic properties. In particular, according to increased social requirements for environmental safeguard, an amount of replenishing a photographic processing solution tends to be decreased and, thus, a residence time of a developer in a processing machine becomes longer. From the viewpoint of a requirement for rapid processing, concentrations of developing agent, bleaching agent, and fixer become high and, thus, a temperature for processing tends to be high, the deterioration in storage ability increasingly becomes a serious problem.

As a concentration of a processing solution becomes high for the purpose of rapid processing, since a concentration of solution carried over to the next bath is high, the variations in conditions (chiefly pH) are increased. For this reason, the effect of a metal masking agent is disadvantageously thinned. Consequently, in particular it has been desired to develop an-excellent novel chelating agent which effectively masks deposited metal ions over a prolonged period without any trouble and with a little affection with variation in conditions.

Consequently, the first object of the present invention is to provide an iron complex having an appropriate oxidizing power and a little influence upon co-existing compounds.

The second object of the present invention is to provide an iron complex having a small change in the oxidizing power by the variation in pH.

The third object of the present invention is to provide a novel additive for photography which hardly affects photographic properties (especially, sensitivity and fogging).

The fourth object of the present invention is to provide a photographic processing composition without generation of any precipitate and sludge even when mixing a metal ion.

The fifth object of the present invention is to provide a stable processing composition without any decrease in effective components, without forming ineffective components and without forming any component having a photographically adverse effect even when mixing a metal ion.

The sixth object of the present invention is to provide a processing composition which can sufficiently maintain abilities even under severe conditions due to heightening a temperature of the processing composition and extending a residence period of a processing solution, and to provide a processing process using the same.

The seventh object of the present invention is to provide a processing composition which effectively masks deposited metal ions over a prolong period without any trouble and with a little affection with variation in conditions, even in a processing solution having high concentration, and to provide a processing process using the same.

The eighth object of the present invention is to provide a composition for processing a silver halide photosensitive material excelling in a desilvering property, particularity a processing composition having a bleaching ability, and to provide a processing method using the same.

The ninth object of the present invention is to provide a composition for processing a silver halide photosensitive material having a little bleach fogging, particularity a processing composition having a bleaching ability, and to provide a processing method using the same.

The tenth object of the present invention is to provide a composition for processing a silver halide photosensitive material having a little staining with the time elapse, particularity a processing composition having a bleaching ability, and to provide a processing method using the same.

The eleventh object of the present invention is to provide a composition for processing a silver halide photosensitive material which can stably maintain the abilities described above even when being continuously processed, particularity a processing composition having a bleaching ability, and to provide a processing method using the same.

The twelfth object of the present invention is to provide a bleach-fixing composition which is difficult to decompose a fixer and can maintain stable processing abilities when being used as a bleach-fixing, and to provide a processing process using the same.

The thirteenth object of the present invention is to provide a bleach-fixing composition which exhibits rapid desilvering property on running processing, which forms only a small amount of precipitate, and which is free of staining on the surface of a photosensitive material and of blockage of a filter, and to provide a processing process using the same.

SUMMARY OF THE INVENTION

These and other objects can be solved by:

1. An iron complex of a compound represented by formula (I):

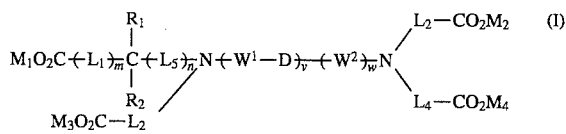

wherein $R_1$ is an aliphatic hydrocarbon group, an aryl group, or a heterocyclic ring group;

$R_2$ is hydrogen, an aliphatic hydrocarbon group, an aryl group, or a heterocyclic ring group;

$L_1$, $L_2$, $L_3$, $L_4$ and $L_5$ are independently an alkylene group;

m and n are independently 0 or 1;

$W^1$ and $W^2$ are independently an alkylene group, an arylene group, aralkylene group or a divalent nitrogen-containing heterocyclic ring group;

D is a single bond, —O—, —S— or —N($R_w$)— where $R_w$ is hydrogen, an aliphatic hydrocarbon group or an aryl group;

v is 0 or an integer of from 1 to 3;

w is an integer of from 1 to 3; and $M_1$, $M_2$, $M_3$ and $M_4$ are independently hydrogen or a cation.

2. A process for producing an iron complex by reacting a compound represented by formula (I) with an iron salt, which comprises isolating the iron complex at a pH level of from 1 to 7.

3. An additive for photography represented by formula (I).

4. An additive for photography represented by the following formula (II)

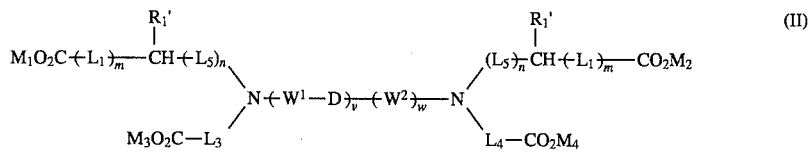

wherein $R_1'$ is an aliphatic hydrocarbon group, and $L_1$, $L_3$, $L_4$, $L_5$, m, n, $W^1$, $W^2$, D, v, w, $M_1$, $M_2$, $M_3$, $M_4$, and have the same meaning as those defined in formula (I) of the above item 1.

5. An additive for photography represented by the following formula (III)

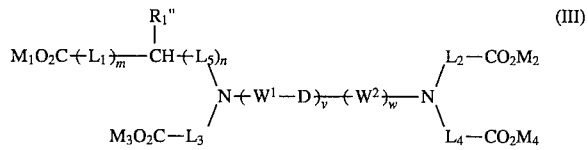

wherein $R_1''$ is an aryl group, $L_1$, $L_2$, $L_3$, $L_4$, $L_5$, m, n, $W^1$, $W^2$, D, v, w, $M_1$, $M_2$, $M_3$, and $M_4$, have the same meaning as those defined in formula (I) of the above item 1.

6. A metal chelate compound for photography of a compound represented by formula (I) of the above item 3.

7. A metal chelate compound for photography of a compound represented by formula (II) of the above item 4.

8. A metal chelate compound for photography of a compound represented by formula (III) of the above item 5.

9. A processing composition for bleach-fixing of a silver halide photosensitive material comprising at least one metal chelate compound of a compound represented by formula (I) of the above item 3 and at least one member of sulfinic acid and salts thereof.

10. A process for processing a silver halide photosensitive material which comprises processing an imagewise exposed silver halide photosensitive material in the presence of at least one of compounds represented by formula (I) shown above and metal chelate compounds thereof.

DETAILED DESCRIPTION OF THE INVENTION

The constructional feature of formula (I) is the fact that a branched alkylene group is introduced between the carboxy group and the N in the aminopolycarboxylic acid. Up to date, a compound in which an alkylene group between N and N' is branched has been described (JP-A-3-192254), but this compound has not yet solved the problems associated with a bleaching agent. When this compound is used as a chelating agent (only using a portion of a chelate containing no metal), the problems associated with a metal masking agent cannot be solved.

It is difficult to be expect that the introduction of a branched alkylene group between the carboxy group and the N solve the problems described above.

First, the compounds represented by formula (I) will now be described.

The aliphatic hydrocarbon group represented by $R_1$ and $R_2$ is a straight or branched chain or cyclic alkyl group (an alkyl group preferably having 1 to 12 carbon atoms, more preferably having 1 to 7 carbon atoms, particularly having 1 to 4 carbon atoms, such as methyl, ethyl, n-propyl, isopropyl, n-butyl, isobutyl, tert-butyl, n-heptyl, n-hexyl, or cyclohexyl), an alkenyl group (an alkenyl group preferably having 2 to 12 carbon atoms, more preferably having 2 to 6 carbon atoms, particularly having 2 to 4 carbon atoms, such as vinyl or allyl), an alkynyl group (an alkynyl group preferably having 2 to 12 carbon atoms, more preferably having 2 to 6 carbon atoms, particularly having 2 to 4 carbon atoms, such as propargyl group), and the like.

The aliphatic hydrocarbon groups represented by $R_1$ and $R_2$ may have a substituent. Examples of the substituents include aryl groups (aryl groups preferably having 6 to 12 carbon atoms, more preferably having 6 to 10 carbon atoms, and particularly having 6 to 8 carbon atoms, such as phenyl, and p-methylphenyl), amino groups (amino groups preferably having 0 to 20 carbon atoms, more preferably having 0 to 10 carbon atoms, and particularly having 0 to 6 carbon atoms, such as amino, methylamino, dimethylamino, and diethylamino), alkoxy groups (alkoxy groups preferably having 1 to 8 carbon atoms, more preferably having 1 to 6 carbon atoms, and particularly having 1 to 4 carbon atoms, such as methoxy and ethoxy), aryloxy groups (aryloxy groups preferably having 6 to 12 carbon atoms, more preferably having 6 to 10 carbon atoms, and particularly having 6 to 8 carbon atoms, such as phenyloxy), acyl groups (acyl groups preferably having 1 to 12 carbon atoms, more preferably having 2 to 10 carbon atoms, and particularly having 2 to 8 carbon atoms, such as acetyl), alkoxycarbonyl groups (alkoxycarbonyl groups preferably having 2 to 12 carbon atoms, more preferably having 2 to 10 carbon atoms, and particularly having 2 to 8 carbon atoms, such as methoxycarbonyl), aryloxycarbonyl groups (aryloxycarbonyl groups preferably having 7 to 20 carbon atoms, more preferably having 7 to 15 carbon atoms, and particularly having 7 to 10 carbon atoms, such as phenyloxycarbonyl), acyloxy groups (acyloxycarbonyl groups preferably having 2 to 12 carbon atoms, more preferably having 2 to 10 carbon atoms, and particularly having 2 to 8 carbon atoms, such as acetoxy), acylamino groups (acylamino groups preferably having 1 to 10 carbon atoms, more preferably having 2 to 6 carbon atoms, and particularly having 2 to 4 carbon atoms, such as acetylamino), alkoxycarbonylamino groups (alkoxycarbonylamino groups preferably having 2 to 12 carbon atoms, more preferably having 2 to 10 carbon atoms, and particularly having 2 to 8 carbon atoms, such as methoxycarbonylamino), aryloxycarbonylamino groups (aryloxycarbonylamino groups preferably having 7 to 20 carbon atoms, more preferably having 7 to 12 carbon atoms, and particularly having 7 to 10 carbon atoms, such as phenyloxycarbonylamino), sulfonylamino groups (sulfonylamino groups preferably having 1 to 10 carbon atoms, more preferably having 1 to 6 carbon atoms, and particularly having 1 to 4 carbon atoms, such as methanesulfonylamino), sulfamoyl groups (sulfamoyl groups preferably having 0 to 10 carbon atoms, more preferably having 0 to 6 carbon atoms, and particularly having 0 to 4 carbon atoms, such as sulfamoyl and methylsulfamoyl), carbamoyl groups (carbamoyl groups preferably having 1 to 10 carbon atoms, more preferably having 1 to 6 carbon atoms, and particularly having i to 4 carbon atoms, such as carbamoyl and methylcarbamoyl), alkylthio groups (alkylthio groups preferably having 1 to 8 carbon atoms, more preferably having 1 to 6 carbon atoms, and particularly having 1 to 4 carbon atoms, such as methylthio, ethylthio, and carboxymethylthio), arylthio groups (arylthio groups preferably having 6 to 20 carbon atoms, more preferably having 6 to 10 carbon atoms, and particularly having 6 to 8 carbon atoms, such as phenylthio), sulfonyl groups (sulfonyl groups preferably having 1 to 8 carbon atoms, more preferably having 1 to 6 carbon atoms, and particularly having 1 to 4 carbon atoms, such as methanesulfonyl), sulfinyl groups (sulfinyl groups preferably having 1 to 8 carbon atoms, more preferably having 1 to 6 carbon atoms, and particularly having 1 to 4 carbon atoms, such as methanesulfinyl), ureido groups (ureido groups preferably having 1 to 8 carbon atoms, more preferably having 1 to 6 carbon atoms, and particularly having 1 to 4 carbon atoms, such as ureido and methylureido), hydroxy group, mercapto group, halogen atoms (e.g., fluorine atom, chlorine atom, bromine atom, and iodine atom), cyano group, sulfo group, carboxy group, nitro group, hydroxamic acid group, heterocyclic ring group (e.g., imidazolyl and pyridyl), and the like. These substituents may be further substituted. In the case where two or more substituents exist, they may be the same or different. Preferred substituents are amino groups, alkoxy groups, carboxy group, hydroxy group, halogen atoms, cyano group and nitro group, more preferably alkoxy groups, carboxy group, hydroxy group, and halogen atoms, further more preferably amino groups, carboxy group and hydroxy group, and particularly hydroxy group and carboxy group.

The aliphatic hydrocarbon group represented by $R_1$ and $R_2$ is an alkyl group having 1 to 12 carbon atoms, more preferably 1 to 7 carbon atoms, and particularly 1 to 4 carbon atoms, except the carbon of a substituent.

Specifically, preferable are methyl, ethyl, n-propyl, isopropyl, n-butyl, benzyl, hydroxymethyl, carboxymethyl, and 5-imidazolyl, with methyl, ethyl, n-propyl, isopropyl, and n-butyl being particularly preferable.

The aryl group represented by $R_1$ and $R_2$ may be a single ring or form a condensed ring together with any other ring, and preferably is an aryl group having 6 to 20 carbon atoms, more preferably 6 to 16 carbon atoms, and particularly 6 to 12 carbon atoms.

The aryl group represented by $R_1$ and $R_2$ is preferably a single or bicyclic ring such as phenyl or naphthyl, and more preferably phenyl.

The aryl group represented by $R_1$ and $R_2$ may have a substituent. Examples of the substituents are alkyl groups, alkenyl groups, alkynyl groups, etc. in addition to the substituents mentioned under the examples of the substituents for the aliphatic hydrocarbon group represented by $R_1$ and $R_2$.

The heterocyclic ring group represented by $R_1$ and $R_2$ is a 3- to 10-member, saturated or unsaturated heterocyclic ring containing at least one of N, O and S atoms, and the ring may be a single ring or form a condensed ring together with any other ring.

Preferable heterocyclic rings are 5- or 6-member aromatic heterocyclic rings, more preferable are 5- or 6-member aromatic heterocyclic rings containing nitrogen atom, and particularly preferable are 5- or 6-member aromatic heterocyclic rings containing 1 or 2 nitrogen atoms.

Typical examples of the heterocyclic rings include pyrolidine, piperidine, piperazine, morpholine, thiophene, fran, pyrrole, imidazole, pyrazole, pyridine, pyrazine, pyridazine, triazole, triazine, indole, indazole, purine, thiadiazole, oxadiazole, quinoline, phthalazine, naphthyridine, quinoxaline, quinazoline, cinnoline, pteridine, acridine, phenanthroline, phenazine, tetrazole, thiazole, oxazole, etc. Preferred heterocyclic rings are pyrrole, imidazole, pyrazole, pyridine, pyrazine, pyridazine, triazole, triazine, indole, indazole, thiadiazole, oxadiazole, quinoline, phthalazine, quinoxaline, quinazoline, cinnoline, tetrazole, thiazole, and oxazole, more preferably imidazole, pyrazole, pyridine, pyrazine, indole, indazole, thiadiazole, oxadiazole, quinoline, thiazole, and oxazole, still more preferably imidazole, pyridine, and quinoline, and particularly imidazole and pyridine.

The heterocyclic ring group represented by $R_1$ and $R_2$ may possess a substituent, and examples of the substituents include alkyl groups, alkenyl groups, alkynyl groups, in addition to the substituents mentioned as the examples of the substituents for the aliphatic hydrocarbon groups represented by $R_1$ and $R_2$.

As $R_1$, an alkyl group having 1 to 7 carbon atoms or phenyl group is preferable, with an alkyl group having 1 to 4 carbon atoms or phenyl group being more preferable.

As $R_2$, hydrogen or an alkyl group having 1 to 4 carbon atoms is preferable, with hydrogen being more preferable.

The alkylene group represented by $L_1$ to $L_5$ may be a straight or branched, or cyclic, and more preferably is a straight or branched chain alkylene group. The carbon number constructing the alkylene group is from 1 to 10, more preferably from 1 to 6, and particularly from 1 to 4.

As $L_1$ and $L_5$, methylene is preferable and unsubstituted methylene is more preferable. As $L_2$, $L_3$, and $L_4$, methylene and ethylene are preferable.

The alkylene group represented by $L_1$ to $L_5$ may possess a substituent, and examples of the substituents include alkenyl groups and alkynyl groups, in addition to the substituents mentioned as the examples of the substituents for the aliphatic hydrocarbon groups represented by $R_1$ and $R_2$.

m and n are independently 0 or 1, and preferable combinations are (m,n)=(1,0), (m,n)=(0,1), and (m,n)=(0,0), with the combinations of (m,n)=(1,0) and (m,n)=(0,0) being more preferable.

The alkylene group represented by $W^1$ and $W^2$ may be a straight or branched, or cyclic, and more preferably is a straight or branched chain alkylene group. The carbon number constructing the alkylene group is from 2 to 8, more preferably from 2 to 6, and particularly from 2 to 4. Examples of the alkylene groups represented by $W^1$ and $W^2$ are ethylene, propylene, trimethylene, 1,2-cyclohexylene, preferably ethylene, propylene, trimethylene, and tetramethylene, and more preferably ethylene and trimethylene.

The arylene group represented by $W^1$ and $W^2$ may be a single ring or may form a condensed ring together with any other ring, and the arylene group preferably possesses 6 to 20 carbon atoms, more preferably 6 to 16 carbon atoms, and more preferably 6 to 12 carbon atoms.

The arylene group represented by $W^1$ and $W^2$ is preferably a single or bicyclic ring, such as phenylene and naphtylene, with phenylene being preferred.

The aralkylene group represented by $W^1$ and $W^2$ is an aralkylene group preferably having 7 to 21 carbon atoms, more preferably having 7 to 17 carbon atoms, and particularly having 7 to 13 carbon atoms, such as o-xylenyl.

As the divalent nitrogen-containing heterocyclic ring group represented by $W^1$ and $W^2$, 5- or 6-member groups whose hetero atom is nitrogen such as imidazolyl are preferred.

$W^1$ and $W^2$ may possess a substituent, and examples of the substituents include alkenyl groups and alkynyl groups, in addition to the substituents mentioned as the examples of the substituents for the aliphatic hydrocarbon groups represented by $R_1$ and $R_2$.

D is a single bond, —O—, —S—, or —N($R_w$)—.

The aliphatic hydrocarbon groups and aryl groups represented by $R_w$ have the same meaning as those of the aliphatic hydrocarbon groups and aryl groups represented by $R_1$ and $R_2$. The aliphatic hydrocarbon groups and aryl groups represented by $R_w$ may possess a substituent, and examples of the substituents include alkenyl groups and alkynyl groups, in addition to the substituents mentioned as the examples of the substituents for the aliphatic hydrocarbon groups represented by $R_1$ and $R_2$.

Preferred substituents of $R_w$ are carboxy group, phosphono group, hydroxy group, and sulfo group, and more preferable is carboxy group.

Preferred $R_w$ is an alkyl group which may be substituted having 1 to 8 carbon atoms (e.g., methyl or carboxymethyl) or an aryl group having 6 to 10 carbon atoms (e.g., phenyl).

v is 0 or an integer of from 1 to 3. When v is 2 or more, $W^1$-D may be the same or different. v is preferably from 0 to 2, more preferably 0 or 1, and particularly 0. w is an integer of from 1 to 3. When w is 2 or 3, $W_2$ may be the same or different. w is preferably 1 or 2.

Examples of $(W^1-D)_v-(W^2)_w-$ include:

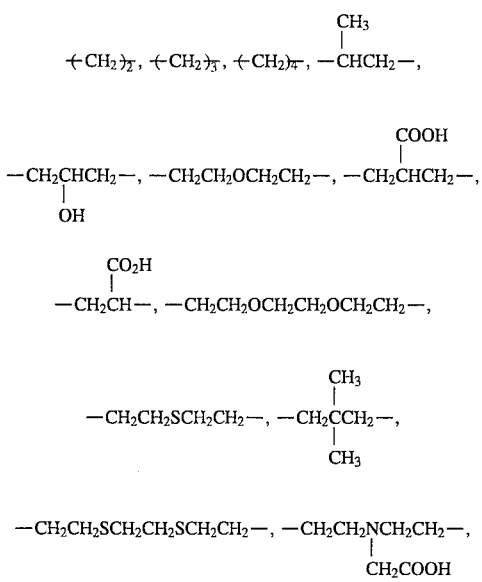

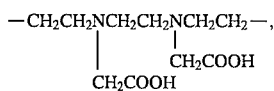

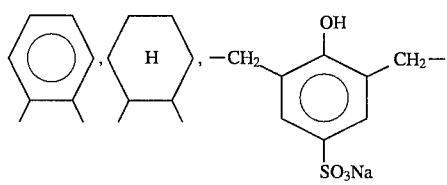

-continued

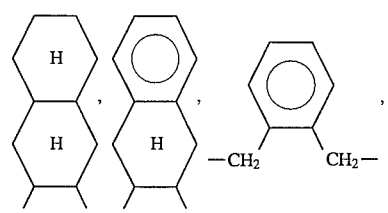

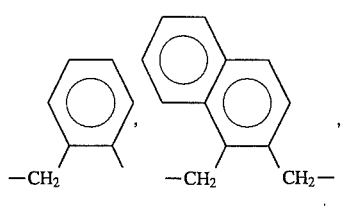

-continued

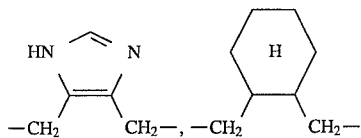

$(W^1-D)_v-(W^2)_w-$ is more preferably ethylene, propylene, trimethylene or 2,2-dimethyltrimethylene, still more preferably ethylene or trimethylene, and particularly ethylene.

The cations represented by $M_1$, $M_2$, $M_3$ and $M_4$ may be organic or inorganic cations. When two or more cations present in the same molecule, they may be different cations. Examples of cations include alkali metals (e.g., $Li^+$, $Na^+$, $K^+$, $Cs^+$, etc.), alkaline earth metals (e.g., $Ca^{2+}$, $Mg^{2+}$, etc.), ammonium (e.g., ammonium, tetraethylammonium, etc.), piridinium, phosphonium, (e.g., tetrabutylphosphonium, tetraphenylphosphonium, etc.), etc. Preferably, it is an inorganic cation, and more preferably an alkali metal ion.

Of the compounds represented by formula (I), preferred are compounds represented by formula (II) or (III):

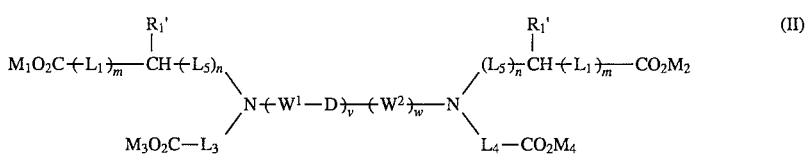

wherein $R_1'$ is an aliphatic hydrocarbon group, the aliphatic hydrocarbon group represented by $R_1'$ having the same meaning as that of the aliphatic hydrocarbon group represented by $R_1$ in formula (I), the same being applicable to the preferred range, $L_1$, $L_3$, $L_4$, $L_5$, m, n, $W^1$, $W^2$, D, v, w, $M_1$, $M_2$, $M_3$, and $M_4$ have the same meanings as those in formula (I), the same being applicable to the preferred ranges.

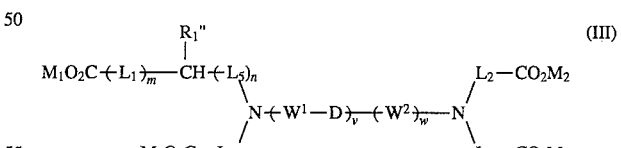

wherein $R_1''$ is an aryl group, the aryl group represented by $R_1''$ having the same meaning as that of the aryl group represented by $R_1$ in formula (I), the same being applicable to the preferred range, $L_1$, $L_2$, $L_3$, $L_4$, $L_5$, m, n, $W^1$, $W^2$, D, v, w, $M_1$, $M_2$, $M_3$, and $M_4$ have the same meanings as those in formula (I), the same being applicable to the preferred ranges.

Of the compounds represented by formula (II), more preferable are compounds represented by formula (IV):

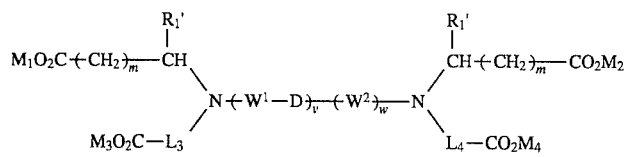

wherein $R_1'$ has the same meaning as that of $R_1'$ in formula (II), the same being applicable to the preferred range, $L_3$, $L_4$, m, $W^1$, $W^2$, D, v, w, $M_1$, $M_2$, $M_3$, and $M_4$ have the same meanings as those in formula (I), the same being applicable to the preferred ranges.

Of the compounds represented by formula (III), more preferable are compounds represented by formula (V):

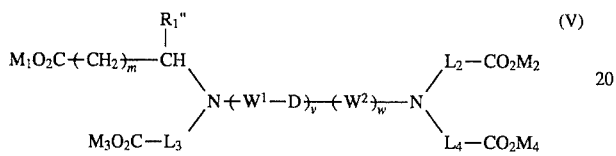

wherein $R_1''$ has the same meaning as that of $R_1''$ in formula (III), the same being applicable to the preferred range, $L_2$, $L_3$, $L_4$, m, $W^1$, $W^2$, D, v, w, $M_1$, $M_2$, $M_3$, and $M_4$ have the same meanings as those in formula (I), the same being applicable to the preferred ranges.

Of the compounds represented by formula (IV), still more preferable are compound represented by formula (VI):

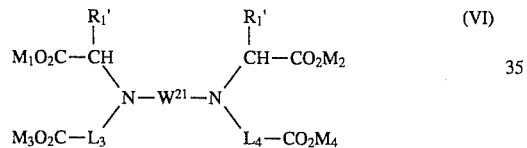

wherein $R_1'$ has the same meaning as that of $R_1'$ in formula (II), the same being applicable to the preferred range, $W^{21}$ is the alkylene group having 2 to 8 carbon atoms of $W^2$ in formula (I), the same being applicable to the preferred range, $L_3$, $L_4$, $M_1$, $M_2$, $M_3$, and $M_4$ have the same meanings as those same being applicable to the preferred ranges.

Of the compounds represented by formula (V), still more preferable are compound represented by formula (VII):

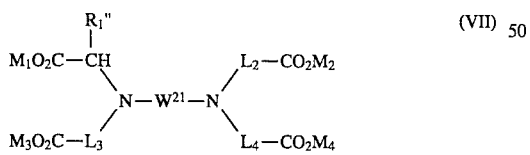

wherein $R_1''$ has the same meaning as that of $R_1''$ in formula (III), the same being applicable to the preferred range, $W^{21}$ is the alkylene group having 2 to 8 carbon atoms of $W^2$ in formula (I), the same being applicable to the preferred range, $L_2$, $L_3$, $L_4$, $M_1$, $M_2$, $M_3$, and $M_4$ have the same meanings as those in formula (I), the same being applicable to the preferred ranges.

In the compounds represented by formula (I), those having a total carbon number of not more than 22 are preferable in terms of the solubility in water.

Typical examples of the compounds represented by formula (I) include, but are not restricted to:

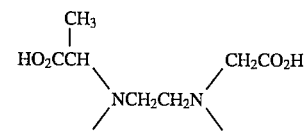
1

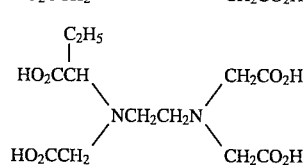
2

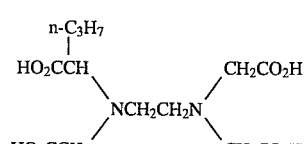
3

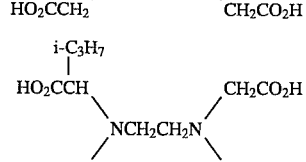
4

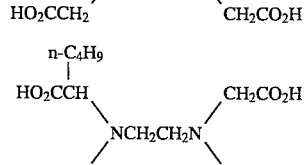
5

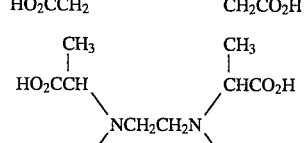
6

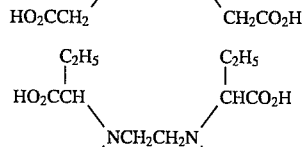
7

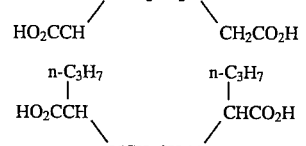
8

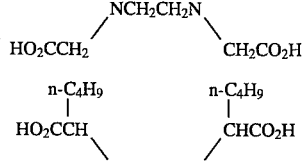
9

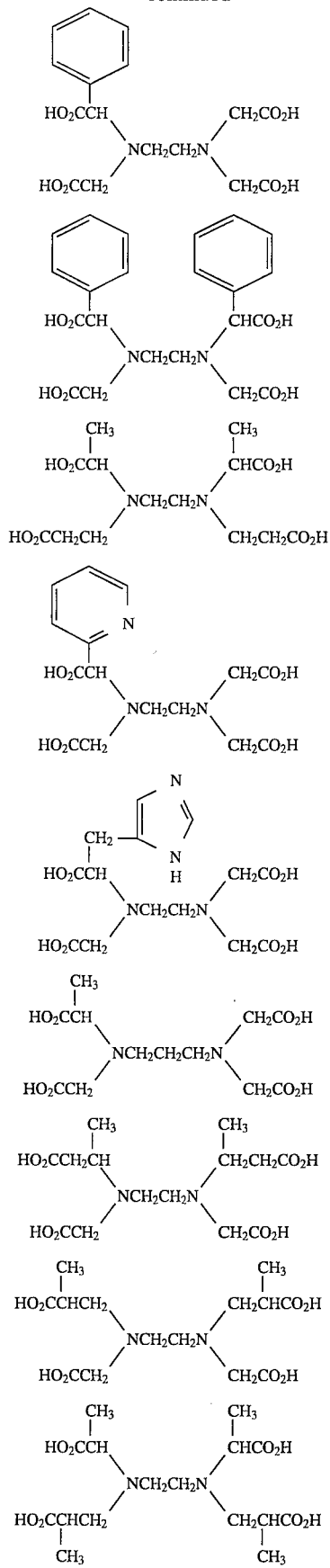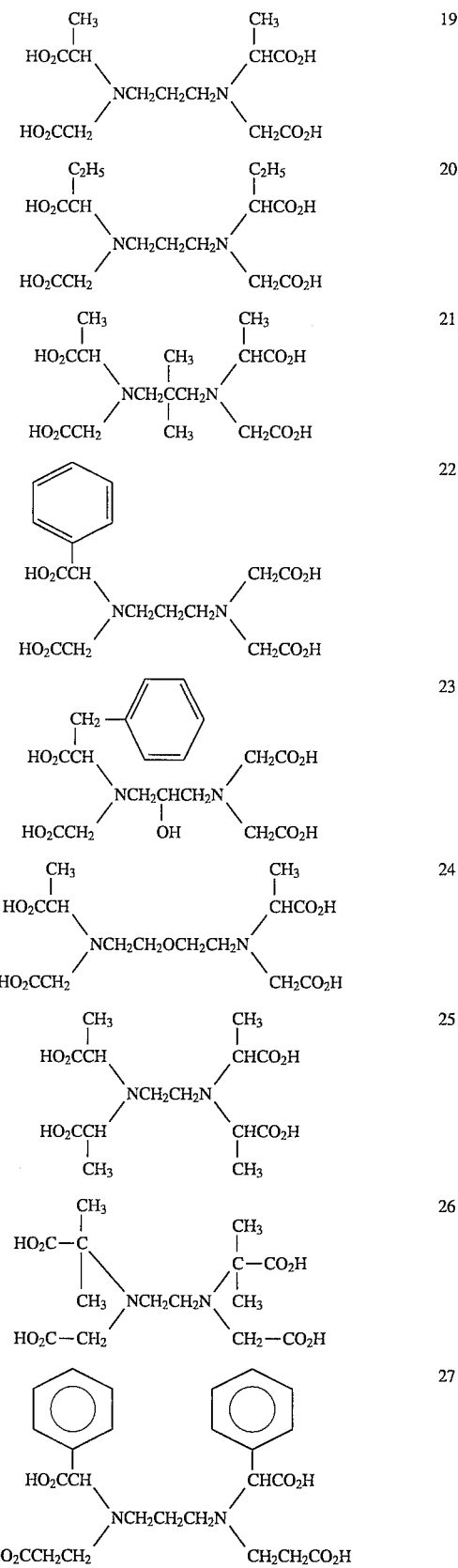

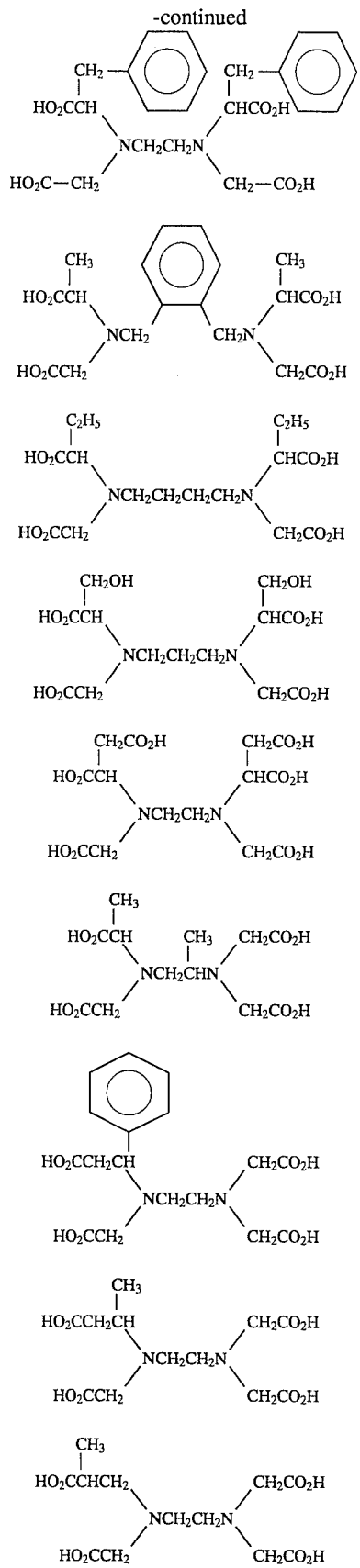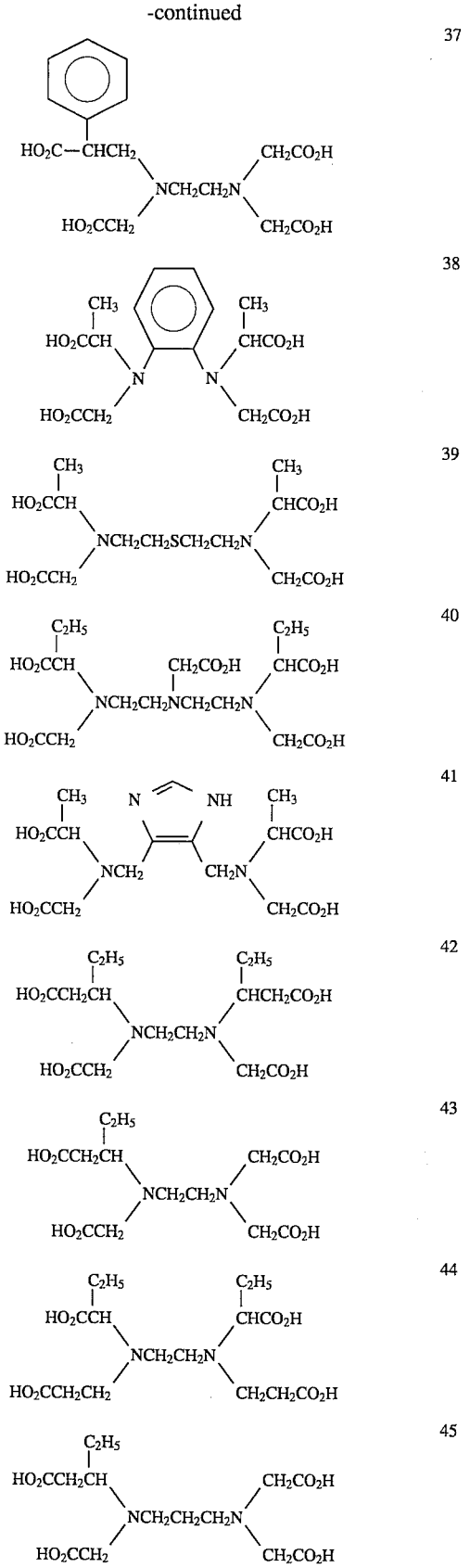

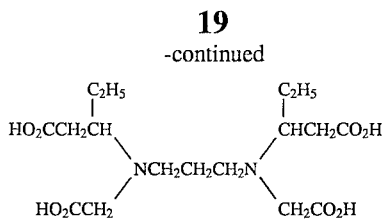

46

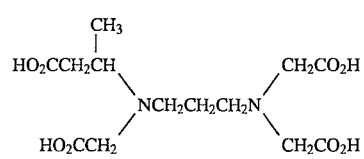

47

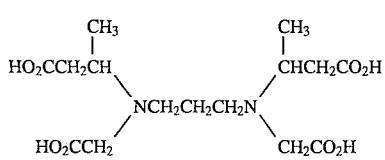

48

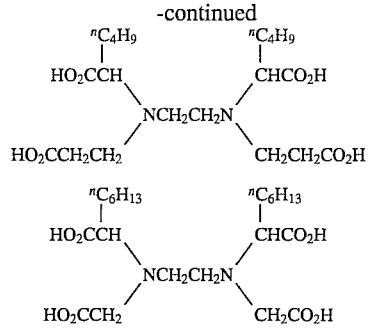

50

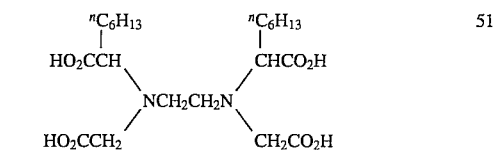

51

These compounds may be used in a salt form.

The compound represented by formula (I) of the present invention can be synthesized according to a process described, for example, in Inorganic Chemistry, 8, (6), p. 1374 (1969), and can be synthesized, for example, as shown in Scheme 1, by reacting compound (A) with amine compound (B), followed by reacting with compounds (E), (F), and (G).

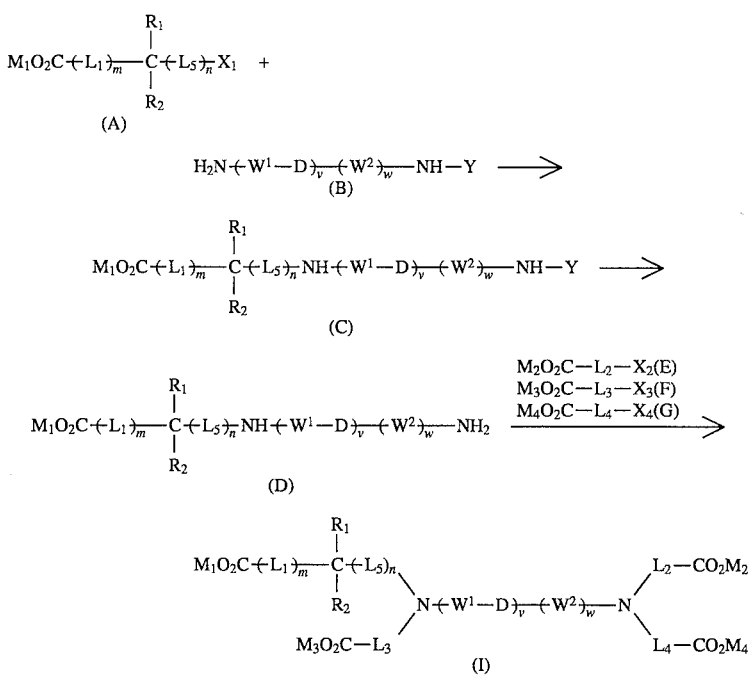

Scheme 1 wherein $R_1$, $R_2$, $L_1$, $L_2$, $L_3$, $L_4$, $L_5$, m, n, $w^1$, $w^2$, D, v, w, $M_1$, $M_2$, $M_3$, and $M_4$ have the same meanings as those in formula (I), Y is hydrogen or a protective group (e.g., an acyl group, benzyl group, etc.), and $X_1$, $X_2$, $X_3$, and $X_4$ are independently an elimination group (e.g., a halogen atom such as chlorine atom, bromine atom, or iodine atom, a sulfonate group such as methylsulfonate or p-toluenesulfonate, etc).

When $X_1$, $X_2$, $X_3$, and $X_4$ are halogens, commercially available compounds can be used as compounds (A), (E), (F), and (G), which are the raw materials, and the raw material compounds can be synthesized by halogenating carboxylic acid derivatives. The halogenation can be carried out according to a process described in Shin Jikken Kagaku -continued

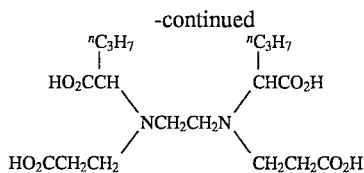

49

Koza (New Experimental Chemical Lecture), Vol 14, p. 351–354, Maruzen Press. When $X_1$, $X_2$, $X_3$, and $X_4$ are sulfonato groups, hydroxy derivatives are used as raw materials and sulfonate esterification of the hydroxy group can be applied. For example, the compounds can be synthesized according to a process described in Shin Jikken Kagaku Koza (New Experimental Chemical Lecture), Vol 14, p. 1793–1798, Maruzen Press.

When Y is hydrogen, a commercially available compound can be used as amine compound (B). When Y is a protective group, a usual process for introducing a protective group into an amine can be applied, and, for example, compound (B) can be synthesized according to a process described in Shin Jikken Kagaku Koza (New Experimental Chemical Lecture), Vol 14, p. 2555–2568, Maruzen Press.

The synthesis of compound (C) may utilize a solvent, and although the solvent is not restricted as long as it does not participate in the reaction, for example, water, alcohols (e.g., methanol, ethanol, 2-propanol, etc.), acetonitrile, dimethylformamide, dimethylacetamide, etc. can be mentioned. Compound (A) is used in an amount of from 0.01 to 10 times mol, preferably from 0.01 to 6 times mol, and more preferably from 0.01 to 2 times mol, of compound (B). This reaction is preferably carried out in the presence of a base, and examples of the bases include alkali (sodium hydroxide, potassium hydroxide, sodium carbonate, potassium carbonate, etc.), and tertiary amines (e.g., trimethylamine). An amount of the base is usually from 1 to 10 times mol, preferably from 1 to 6 times mol, and more preferably from 1 to 2 times mol, of compound (A). When a catalytic amount (preferably from 0.001 to 0.5 time mol, more preferably from 0.01 to 0.5 time mol, and particularly from 0.01 to 0.3 time mol, of compound (B)) of an iodide such as sodium iodide or potassium iodide is added, the reaction advantageously proceeds. The reaction is carried out usually at 0° to 100° C., preferably 10° to 80° C., and more preferably 20° to 70° C..

In the synthesis of compound (D) (when Y is hydrogen, compound (C) becomes the same compound as compound (D)), conditions for detaching protective group suitable for the protective group used can be utilized and, for example, a process described in Shin Jikken Kagaku Koza (New Experimental Chemical Lecture), Vol 14, p. 2555–2568, Maruzen Press is applicable.

Of the compounds included in the above-mentioned synthetic intermediates (C) and (D), compounds represented by (C)' and (D)' shown in Scheme 2 can also be produced with reference to a process described in Journal of the American Society, Vol. 72, p. 5357–5361 (1950). To be specific, as shown in Scheme 2, diamine derivatives can be caused to be reacted with acrylonitrile derivatives to obtain intermediates (J) and (K). After the isolation and purification by distillation in vacuo, the nitrile portion is hydrolyzed with an acid, and the aqueous solution becomes alkaline with a base, and ammonia formed during the hydrolysis is removed whereby compounds (C)' and (D)' can be obtained.

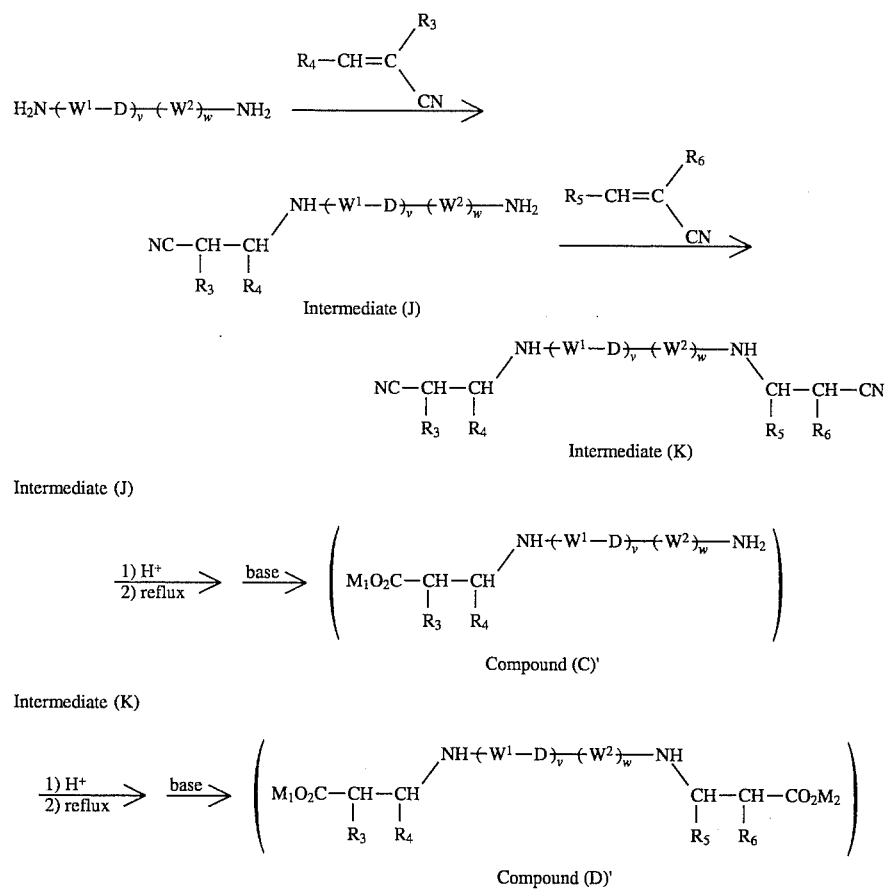

Scheme 2 wherein $W^1$, $W^2$, D, v, w, $M_1$ and $M_2$ in synthetic Scheme 2 have the same meanings as those of formula (I), $R_3$, $R_4$, $R_5$, and $R_6$ are independently hydrogen, an aliphatic hydrocarbon group, an aryl group or a heterocyclic ring group.

As the raw material diamine derivatives and acrylonitrile derivatives, commercially available products can be used.

With regard to the addition reaction between the diamine derivative and the acrylonitrile derivative, thermal reflux is carried out in the absence of any solvent, and the purification can be carried out by distillation. At this time, by adjusting an amount of the acrylonitrile derivative to be added, the proportion of intermediate (J) to intermediate (K) formed can be varied. These two intermediates can be separated by distillation. The reaction proceeds if a solvent is or is not present. If a solvent is used, although the solvent is not specifically restricted as long as it does not participate in the reaction, examples of the solvents include alcohols (e.g., methanol, ethanol, 2-propanol, butanol, etc.), ethers (e.g., dioxane, tetrahydrofuran, etc.), dimethylformamide, dimethylacetamide, etc. Instead of the acrylonitrile derivative, an acrylic acid derivative may be used. In this case, the subsequent hydrolysis is not required to be carried out. However, in this case, since the purification by distillation cannot be carried out, the reaction is preferably carried out with the acrylonitrile derivative.

The subsequent hydrolysis can also be carried out with reference to the above literature. As the acid, inorganic or organic acid can be used. For example, hydrochloric acid, nitric acid, sulfuric acid, p-tolunenesulfonic acid, etc. can be mentioned. As the base, inorganic or organic bases can be used. For example, sodium hydroxide, potassium hydroxide, sodium carbonate, triethylamine, etc. can be mentioned. As a process for removing ammonia, ammonia may be removed by heating or in vacuo. In this case, the pH is preferably alkaline.

In the synthesis of compound (I) according to Scheme 1, the conditions for synthesizing compound (C) are applicable. When $L_2$, $L_3$, and $L_4$ are ethylene derivatives, Michael reaction using acrylic acid derivatives or salts thereof can be utilized instead of compounds (E), (F), and (G).

Moreover, aldehyde or ketone derivatives are used instead of compounds (A), (E), (F), and (G), and compound (I) can be synthesized by reducing the imine or immonium formed from the reaction with compounds (B) and (D). In this case, the raw material aldehyde or ketone derivatives which can be used are commercially available products. The conditions for the reduction are not specifically restricted, and, for example, a process described in Shin Jikken Kagaku Koza (New Experimental Chemical Lecture), Vol 14, p. 1339–1341, Maruzen Press, is applicable, and particularly a process by catalytic hydrogenation reduction is preferred. Alternatively, an amino acid synthesizing process by a Strecker process due to the reaction between a carbonyl compound and hydrogen cyanide or a cyanide ion is applicable. In this case, as the conditions, a process described in Shin Jikken Kagaku Koza (New Experimental Chemical Lecture), Vol 14, p. 1673–1674, Maruzen Press, or Journal of Organic Chemistry, Vol. 15, p. 46 (1950) may be applied.

The order of the introduction of $M_1O_2C$—$(L_1)_m$—$CR_1(R_2)$—$(L_5)_n$—, $M_2O_2C$—$L_3$—, $M_3O_2C$—$L_3$—, and $M_4O_2C$—$L_4$— may not be the order described in Scheme 1. Moreover, the reactions may be continuously carried out without isolating the synthetic intermediates.

Typical synthetic examples of compounds represented by formula (I) will now be described.

SYNTHETIC EXAMPLE 1

SYNTHESIS OF COMPOUND 6

Into a three-neck flask were incorporated 17.6 g (0.100 mol) of ethylenediamine-N,N'-diacetic acid (produced by Tokyo Kasei) and 40 ml of water, and the content was cooled on an ice bath. With thoroughly stirring, 16.0 g (0.200 mol) of an aqueous 50% sodium hydroxide solution was added dropwise. Into a beaker 61.2 g (0.400 mol) of 2-bromopropionic acid was weighed, 50 ml of water was added, and the content was thoroughly stirred on an ice bath. While maintaining the inner temperature at 10° C. or less, 64.0 g (0.80 mol) of an aqueous 50% sodium hydroxide solution was added dropwise. The solution was poured in the above-mentioned three-neck flask, and the mixture was stirred at room temperature for 6 hours. After left standing overnight, the reaction liquid was filtered, the pH value was adjusted to approximately 1.5 with concentrated hydrochloric acid, and the salt was removed by electrodialysis. The reaction liquid was concentrated by approximately ½, left standing overnight, and the separated crystal was filtered off. Washing with water and drying in vacuo gave 24.6 g (0.074 mol) of an intended Compound 6 as ⅔ hydrate.

Yield: 74%

Melting point: 196°–199° C. (decomposed)

SYNTHETIC EXAMPLE 2

SYNTHESIS OF COMPOUND 7

A reactor in which 92.1 g (0.511 mol) of 2-bromo-n-butanoic acid and 300 ml of water were placed was cooled on an ice bath, and 100 ml of a solution of 12.7 g (0.211 mol) of ethylenediamine and 44.1 g (1.10 mol) of sodium hydroxide dissolved in water was slowly added dropwise with stirring so that the inner temperature did not exceed 10° C. After stirring at room temperature for 3 hours, the mixture was left standing overnight, and the pH was adjusted to approximately 4 with concentrated hydrochloric acid. After the reaction liquid was concentrated in vacuo by approximately ⅓, the separated crystal was filtered off. Washing with water and drying in vacuo gave 38.0 g (0.164 mol) of ethylenediamine-N,N'-di(2-butanoic acid). (Yield: 78%).

Into a three-neck flask were incorporated 38.0 g (0.164 mol) of ethylenediamine-N,N'-di(2-butanoic acid) and 100 ml of water, and the content was cooled on an ice bath. With thoroughly stirring, 26.2 g (0.328 mol) of an aqueous 50% sodium hydroxide solution was added dropwise. Into a beaker 63.4 g (0.456 mol) of bromoacetic acid was weighed, 150 ml of water was added, and the content was thoroughly stirred on an ice bath. While maintaining the inner temperature at 10° C. or less, 73.0 g (0.913 mol) of an aqueous 50% sodium hydroxide solution was added dropwise. The solution was poured in the above-mentioned three-neck flask, and the mixture was stirred at room temperature for 6 hours. After left standing overnight, the reaction liquid was filtered, the pH value was adjusted to approximately 1.5 with concentrated hydrochloric acid, and the salt was removed by electrodialysis. The reaction liquid was concentrated by approximately ½, left standing overnight, and the separated crystal was filtered off. Washing with water and drying in vacuo gave 31.2 g (0.0852 mol) of an intended Compound 7 as ⅓ hydrate.

Yield: 52%

Melting point: 180°–181° C. (decomposed)

SYNTHETIC EXAMPLE 3

SYNTHESIS OF COMPOUND 8

A reactor in which 90.5 g (0.500 mol) of 2-bromo-n-pentanoic acid and 300 ml of water were placed was cooled on an ice bath, and 100 ml of a solution of 12.0 g (0.200 mol) of ethylenediamine and 40.0 g (1.00 mol) of sodium hydroxide dissolved in water was slowly added dropwise with stirring so that the inner temperature did not exceed 10° C. After stirring at room temperature for 3 hours, the mixture was left standing overnight, the pH was adjusted to approximately 4 with concentrated hydrochloric acid, and stirred for several period of time, after which the separated crystal was filtered off. Washing with water and drying in vacuo gave 30.7 g (0.118 mol) of ethylenediamine-N,N'-di(2-pentanoic acid). (Yield: 59%).

Into a three-neck flask were incorporated 30.7 g (0.118 mol) of ethylenediamine-N,N'-di(2-pentanoic acid) and 100 ml of water, and the content was cooled on an ice bath. With thoroughly stirring, 18.9 g (0.236 mol) of an aqueous 50% sodium hydroxide solution was added dropwise. Into a beaker 49.2 g (0.354 mol) of bromoacetic acid was weighed, 150 ml of water was added, and the content was thoroughly stirred on an ice bath while maintaining the inner temperature at 10° C. or less, 56.6 g (0.708 mol) of an aqueous 50% sodium hydroxide solution was added dropwise. The solution was poured in the above-mentioned three-neck flask, and the mixture was stirred at room temperature for 6 hours. After left standing overnight, the reaction liquid was filtered, the pH value was adjusted to approximately 1.5 with concentrated hydrochloric acid, and the salt was removed by electrodialysis. The reaction liquid was concentrated by approximately ½, left standing overnight, and the separated crystal was filtered off. Washing with water and drying in vacuo gave 23.5 g (0.059 mol) of an intended Compound 8 as monohydrate.

Yield: 54%

Melting point: 160°–162° C. (decomposed)

SYNTHETIC EXAMPLE 4

SYNTHESIS OF COMPOUND 9

A reactor in which 57.8 g (0.296 mol) of 2-bromo-n-hexanoic acid and 150 ml of water were placed was cooled on an ice bath, and 100 ml of a solution of 5.93 g (0.099 mol) of ethylenediamine and 23.7 g (0.593 mol) of sodium hydroxide dissolved in water was slowly added dropwise with stirring so that the inner temperature did not exceed 10° C. After stirring at room temperature for 6 hours, the mixture was left standing overnight, and the pH was adjusted to approximately 4 with concentrated hydrochloric acid. After the reaction liquid was stirred for a several period of time, the separated crystal was filtered off. Washing with water and drying in vacuo gave 17.4 g (0.060 mol) of ethylenediamine-N,N'-di(2-hexanoic acid). (Yield: 61%).

Into a three-neck flask were incorporated 17.4 g (0.060 mol) of ethylenediamine-N,N'-di(2-hexanoic acid) and 50 ml of water, and the content was cooled on an ice bath. With thoroughly stirring, 9.60 g (0.180 mol) of an aqueous 50% sodium hydroxide solution was added dropwise. Into a beaker 25.0 g (0.180 mol) of bromoacetic acid was weighed, 100 ml of water was added, and the content was thoroughly stirred on an ice bath. While maintaining the inner temperature at 10° C. or less, 28.8 g (0.360 mol) of an aqueous 50% sodium hydroxide solution was added dropwise. The solution was poured in the above-mentioned three-neck flask, and the mixture was stirred at room temperature for 6 hours. After left standing overnight, the reaction liquid was filtered, the pH value was adjusted to approximately 2 with concentrated hydrochloric acid, the reaction liquid was concentrated by approximately ⅓, left standing overnight, and the separated white solid was filtered off. Recrystallization of the resulting solid from water/acetonitrile, washing with water and drying in vacuo gave 16.5 g (0.040 mol) of an intended Compound 9 as ⅔ hydrate.

Yield: 67%

Melting point: 162°–164° C. (decomposed)

SYNTHETIC EXAMPLE 5

SYNTHESIS OF COMPOUND 10

Into a reactor in which 11.46 g (0.067 mol) of sodium benzoylformate (produced by Aldrich) and 60 ml of methanol was placed was added 5.67 g of N-acetylethylenediamine (0.056 mol, produced by Tokyo Kasei) with stirring, and the content was refluxed for 2 hours. After the temperature of the reaction liquid was cooled down to room temperature, the liquid was catalytically hydrogenated with a hydrogen gas (hydrogen pressure: 30 kg/cm$^2$) using 10% palladium carbon as a catalyst. After the reaction liquid was filtered to remove the catalyst, the filtrate was concentrated to obtain a candy-like precipitate. To this was added 60 ml of an aqueous 5N sodium hydroxide solution, and thermally refluxed for 2 hours. The reaction liquid was cooled with an ice-water, 27.76 g (0.20 mol) of bromoacetic acid was slowly added with stirring so that the inner temperature did not exceed 10° C. After the pH of the reaction liquid was adjusted to 10 to 11 with 36% hydrochloric acid, the liquid was heated to 40° C., and the reaction was carried out for 6 hours while adding an aqueous 5N sodium hydroxide solution so as to maintain the pH value at 9–11. The reaction liquid was cooled down to room temperature, the pH was adjusted to approximately 2 with 36% hydrochloric acid, the reaction liquid was concentrated in vacuo by approximately ⅓, methanol was added, and the separated salt was filtered off. The operations where the filtrate was concentrated in vacuo by ⅓, methanol was added, and the separated salt was filtered off were conducted three times, and the candy-like substance obtained by concentration in vacuo was then thoroughly washed with acetone. Recrystallization of the remaining white precipitate from water gave 10.7 g (0.029 mol) of an intended compound 10. Yield: 52.3%, Melting point 190–191 (decomposed).

SYNTHETIC EXAMPLE 6

SYNTHESIS OF COMPOUND 12

Into a three-neck flask were incorporated 25.0 g (0.090 mol) of ethylenediamine-N,N'-dipropionic acid dihydrochloride (produced by Tokyo Kasei) and 50 ml of water, and the content was cooled on an ice bath. With thoroughly stirring, 29.0 g (0.36 mol) of an aqueous 50% sodium hydroxide solution was added dropwise. Into a beaker 55.0 g (0.360 mol) of 2-bromopropionic acid was weighed, 50 ml of water was added, and the content was thoroughly stirred on an ice bath. While maintaining the inner temperature at 10° C. or less, 57.6 g (0.72 mol) of aqueous 50% sodium hydroxide solution was added dropwise. The solution was poured in the above-mentioned three-neck flask, and the mixture was stirred at room temperature for 5 hours. After left standing overnight, the reaction liquid was filtered, the pH value was adjusted to approximately 1.5 with concentrated hydrochloric acid. After being concentrated in vacuo until the reaction liquid was approximately 200 ml, the reaction liquid was left standing overnight, and the separated white crystal was filtered off. After washing with water, the crystal was poured into a beaker, 50 ml of water was added thereto, and the crystal was dissolved by the addition of an aqueous 50% sodium hydroxide solution with thoroughly stirring. After the pH was adjusted to approximately 1.5 with concentrated hydrochloric acid and it was left standing overnight, the separated solid was filtered off. Washing with a small amount of water and with acetone and thermal drying gave 6.76 g (0.018 mol) of an intended compound 12 as 3/2 hydrate.

Yield: 20%

Melting point: gradually decomposed from 110° C.

SYNTHETIC EXAMPLE 7

SYNTHESIS OF COMPOUND 19

A reactor in which 254 g (1.66 mol) of 2-bromopropionic acid and 400 ml of water were placed was cooled on an ice-bath, and 150 ml of a solution of 51.3 g (0.692 mol) of 1,3-propanediamine and 66.4 g (1.66 mol) of sodium hydroxide dissolved in water was slowly added dropwise with stirring so that the inner temperature did not exceed 20° C. The mixture was heated to 60° C., and 150 ml of a solution of 66.4 g (1.66 mol) of sodium hydroxide dissolved in water was added dropwise so as to maintain the pH value at 10–11, after which 91.8 g (0.60 mol) of 2-bromopropionic acid was added. The reaction was carried out for another 6 hours, the mixture was cooled down to room temperature, and concentrated hydrochloric acid was added to adjust the pH value to approximately 3. The reaction liquid was concentrated in vacuo by approximately ⅓, methanol was added, and the separated salt was filtered off. The operations where the filtrate was concentrated in vacuo by ⅓, methanol was added, and the separated salt was filtered off were conducted three times. Recrystallization from water/ethanol gave 120 g (0.550 mol) of 1,3-propanediamine-N,N'-di (2-propionic acid). (Yield: 79.5%).

In 300 ml of water were dissolved 50.0 g (0.229 mol) of 1,3-propanediamine-N,N'-di(2-propionic acid) and 127 g (0.914 mol) of bromoacetic acid, and 100 ml of a solution of 54.9 g (1.37 mol) of sodium hydroxide dissolved in water was slowly added dropwise under ice-cooling so as to the inner temperature did not exceed 20° C. The mixture was heated to 60° C., and 80 ml of a solution of 36.6 g (0.195 mol) of sodium hydroxide dissolved in water was added dropwise so as to adjust the pH to 10–11, and then left standing at room temperature overnight. At room temperature, concentrated hydrochloric acid was added to adjust the pH to approximately 2, the reaction liquid was concentrated in vacuo by approximately ⅓, methanol was added, and the separated salt was filtered off. The operations where the filtrate was concentrated in vacuo by ⅓, methanol was added, and the separated salt was filtered off were conducted three times. Recrystallization from water/acetone gave 43.2 g (0.127 mol) of an intended compound 19 as ⅓ hydrate.

Yield: 55%

Melting point: 124°–126° C. (decomposed).

SYNTHETIC EXAMPLE 8

SYNTHESIS OF COMPOUND 20

A reactor in which 40.0 g (0.24 mol) of 2-bromo-n-butanoic acid and 80 ml of water were placed was cooled on an ice bath, and 15 ml of a solution of 7.41 g (0.10 mol) of 1,3-propanediamine and 9.60 g (0.24 mol) of sodium hydroxide dissolved in water was slowly added dropwise with stirring so that the inner temperature did not exceed 20° C. The mixture was heated to 60° C., and 15 ml of a solution of 9.60 g (0.24 mol) of sodium hydroxide dissolved in water was added dropwise so as to maintain the pH value at 10–11, after which 20.4 g (0.12 mol) of 2-bromo-n-butanoic acid was added and 10 mol of a solution of 2.44 g (0.06 mol) of sodium hydroxide dissolved in water was added. The reaction was carried out at 60° C. for 6 hours, the mixture was cooled down to room temperature, and concentrated hydrochloric acid was added to adjust the pH value to approximately 2.5. The reaction liquid was concentrated in vacuo by approximately ⅓ using a rotary evaporation, methanol was added, and the separated salt was filtered off. The operations where the filtrate was concentrated in vacuo by ⅓, methanol was added, and the separated salt was filtered off were conducted three times. Recrystallization from water/ethanol gave 16.0 g (0.065 mol) of 1,3-propanediamine-N,N'-di (2-butanoic acid). (Yield: 65.0%).

Into 100 ml of water were dissolved 12.3 g (0.050 mol) of 1,3-propanediamine-N,N'-di(2-butanoic acid) and 23.3 g (0.20 mol) of sodium chloroacetate, and 30 ml of a solution of 12.0 g (0.30 mol) of sodium hydroxide dissolved in water was slowly added so that the inner temperature did not exceed 20° C. After the reaction was carried out at approximately 30° C. for 8 hours, concentrated hydrochloric acid was added at room temperature so that pH was adjusted to approximately 1, and the salt was removed by electrodialysis. After left standing for 2 days, filtration of the separated solid and washing with water gave 12.9 g (0.034 mol) of compound 20 as monohydrate.

Yield: 68.0%

Melting point: 171°–173° C. (decomposed).

SYNTHETIC EXAMPLE 9

SYNTHESIS OF COMPOUND 16

Scheme 3

$$H_2N-CH_2CH_2-NH_2 \xrightarrow[20h]{CH_3-CH=CH, CN, reflux}$$

$$NCCH_2CH(CH_3)-NH-CH_2CH_2-NH-CHCH_2CN(CH_3) \xrightarrow[2) reflux\ 3h]{1)\ Conc.\ HCl\ 15\ min} \xrightarrow{1)\ 50\%NaOHaq}$$

Intermediate 16B $$\left( NaO_2CCH_2CH(CH_3)-NH-CH_2CH_2-NH-CHCH_2CO_2Na(CH_3) \right) \xrightarrow[2) HCl]{1)\ BrCH_2CO_2H\ 50\%NaOHaq}$$

Compound 16A

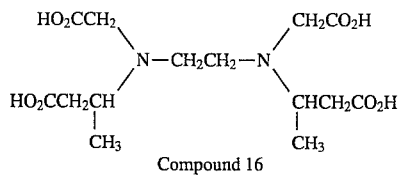

Compound 16

(SYNTHESIS OF COMPOUND 16A)

In a three-neck flask were incorporated 50.0 g (0.832 mol) of ethylenediamine and 223 g (3.328 mol) of crotononitrile, and the mixture was thermally refluxed for 20 hours. Vacuum distillation was carried out with an aspirator (20 mmHg, 130°–150° C.) to remove the substance having a boiling point lower than that of the intended substance. Subsequently, vacuum distillation through a vacuum pump (2 mmHg, 150°–170° C.) was carried out to obtain an intermediate (16B). Into a round bottom flask was incorporated 50 g (0.257 mol) of intermediate (16B), the content was thoroughly stirred with cooling on an ice bath, and 150 ml of concentrated hydrochloric acid was added dropwise through an isotactic dropping funnel over a period of 15 minutes. After the addition, the mixture was thermally refluxed on an oil bath for 3 hours. The solvent was removed in vacuo, an aqueous 50% sodium hydroxide solution was added to be a strong alkali. The formed ammonia was removed in vacuo to obtain compound 16A.

(SYNTHESIS OF COMPOUND 16)

All of the resulting compound 16A and an aqueous solution of 107.3 g (0.772 mol) of bromoacetic acid which had been neutralized with 50% sodium hydroxide were added, thoroughly stirred, and left standing at room temperature overnight. An activated carbon was added to the reaction liquid to carry out a Celite filtration, and the pH was adjusted to 1.5 with concentrated hydrochloric acid. After the salt was removed by electrodialysis, the reaction liquid was concentrated in vacuo and then left standing overnight. The separated crystal was filtered off, and washed with water and with acetone. Thermal dying (45° C.) gave 37 g of an intended compound as ½ hydrate (yield: 41%).

Melting point: 185°–6° C. (decomposed).

Elemental Analysis: as $C_{14}H_{24}N_2O_8 \cdot 1/2\ H_2O$

|  | H (%) | C (%) | N (%) |
|---|---|---|---|
| Calculated | 7.05 | 47.05 | 7.85 |
| Determined | 6.81 | 46.98 | 7.88 |

SYNTHETIC EXAMPLE 10

SYNTHESIS OF COMPOUND 42

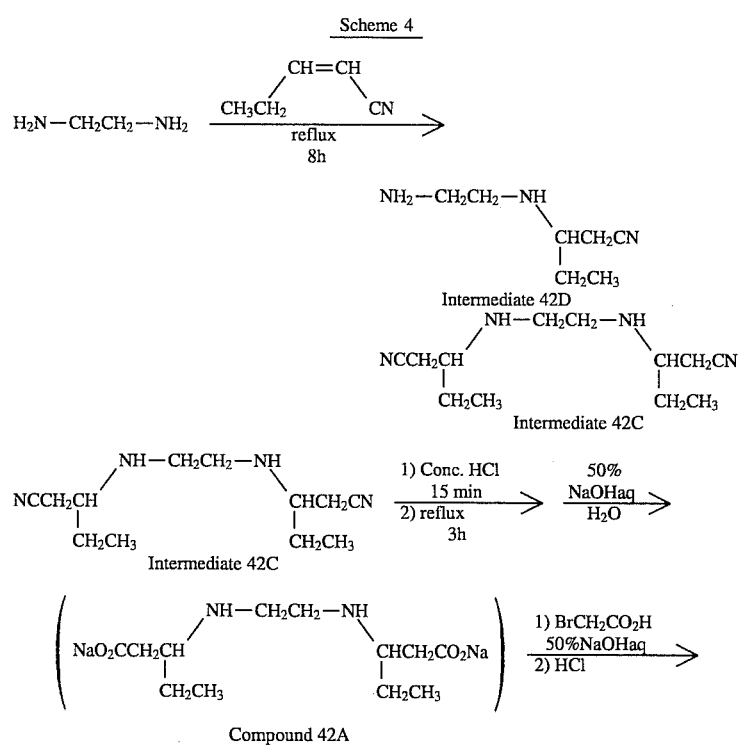

-continued
Scheme 4

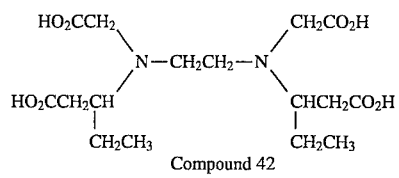

Compound 42

(SYNTHESIS OF COMPOUND 42A)

In a three-neck flask were incorporated 170 g (2.83 mol) of ethylenediamine and 328 g (2.83 mol) of 70% cis-2-pentenenitrile, and the mixture was thermally reflux for 8 hours. Vacuum distillation (20 mmHg, 140°–160° C.) gave intermediate 42 D. Vacuum distillation (2 mmHg, 150°–180° C.) through a vacuum pump gave intermediate 42C. Into a round bottom flask was incorporated 30 g (0.135 mol) of intermediate 42C, the content was thoroughly stirred with cooling on an ice bath, and 150 ml of concentrated hydrochloric acid was added dropwise through an isotactic dropping funnel over a period of 15 minutes. After the addition, the mixture was thermally refluxed on an oil bath for 3 hours. The solvent was removed in vacuo, a small amount of water and an aqueous 50% sodium hydroxide solution were added to the content to be a strong alkali (pH: 13 or more). The formed free ammonia was removed in vacuo to obtain compound 42A.

(SYNTHESIS OF COMPOUND 42)

All of the resulting compound 42A and an aqueous solution of 75 g (0.54 mol) of bromoacetic acid which had been neutralized with 50% sodium hydroxide were added, thoroughly stirred, and left standing at room temperature overnight. An activated carbon was added to the reaction liquid to carry out a Celite filtration, and the pH was adjusted to 1.5 with concentrated hydrochloric acid. After the salt was removed by electrodialysis, the reaction liquid was concentrated in vacuo and then left standing overnight. The separated crystal was filtered off, and washed with water and with acetone. Thermal dying (45° C.) gave 34 g of an intended compound (yield: 66%).

Melting point: 175°–6° C. (decomposed).

Elemental Analysis: as $C_{16}H_{28}N_2O_8$–376.41

|  | H (%) | C (%) | N (%) |
|---|---|---|---|
| Calculated | 7.50 | 51.06 | 7.44 |
| Determined | 7.39 | 50.89 | 7.37 |

SYNTHETIC EXAMPLE 11

SYNTHESIS OF COMPOUND 35

Scheme 5

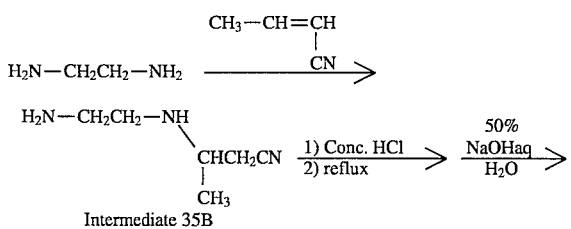

Intermediate 35B

-continued
Scheme 5

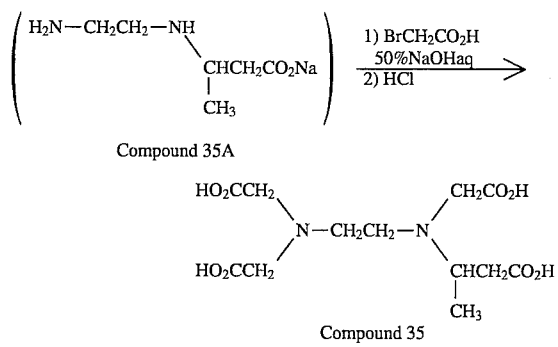

Compound 35

(SYNTHESIS OF COMPOUND 35A)

In a three-neck flask were incorporated 50.0 g (0.832 mol) of ethylenediamine and 55.8 g (0.832 mol) of crotononitrile, and the mixture was thermally refluxed for 20 hours. Vacuum distillation (20 mmHg, 140°–170° C.) gave intermediate 35B. Into a round bottom flask was incorporated 50 g (0.393 mol) of intermediate 35B, the content was thoroughly stirred with cooling on an ice bath, and 150 ml of concentrated hydrochloric acid was added dropwise through an isotactic dropping funnel over a period of 15 minutes. After the addition, the mixture was thermally refluxed on an oil bath for 3 hours. The solvent was removed in vacuo, an aqueous 50% sodium hydroxide solution was added to be a strong alkali. The formed ammonia was removed in vacuo to obtain compound 35A.

(SYNTHESIS OF COMPOUND 35)

All of the resulting compound 35A and an aqueous solution of 107.3 g (0.772 mol) of bromoacetic acid which had been neutralized with 50% sodium hydroxide were added, thoroughly stirred, and left standing at room temperature overnight. An activated carbon was added to the reaction liquid to carry out a Celite filtration, and the pH was adjusted to 1.5 with concentrated hydrochloric acid. After the salt was removed by electrodialysis, the reaction liquid was concentrated in vacuo and then left standing overnight. The separated crystal was filtered off, and washed with water and with acetone. Thermal dying (45° C.) gave 88.7 g of an intended compound as ½ hydrate (yield: 32%).

Melting point: 191°–192° C. (decomposed).

Elemental Analysis: as $C_{12}H_{20}N_2O_8 \cdot \frac{1}{2} H_2O$

|  | H (%) | C (%) | N (%) |
|---|---|---|---|
| Calculated | 6.43 | 43.77 | 8.51 |
| Determined | 6.22 | 43.79 | 8.68 |

SYNTHETIC EXAMPLE 12

SYNTHESIS OF COMPOUND 43

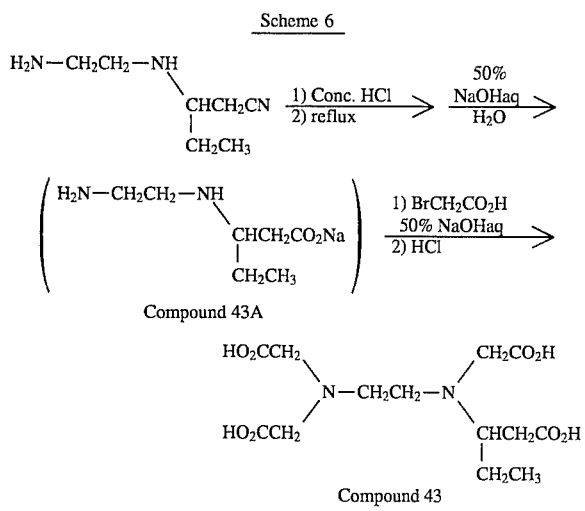

Compound 43

(SYNTHESIS OF COMPOUND 43A)

Into a round bottom flask was incorporated 100 g (0.708 mol) of intermediate 42D obtained in Synthetic Example 10, the content was thoroughly stirred with cooling on an ice bath, and 300 ml of concentrated hydrochloric acid was added dropwise through an isotactic dropping funnel over a period of 15 minutes. After the addition, the mixture was thermally refluxed on an oil bath for 3 hours. The solvent was removed in vacuo, a small amount of water and an aqueous 50% sodium hydroxide solution were added to the content to be a strong alkali (pH: 13 or more). The formed free ammonia was removed in vacuo to obtain compound 43A.

(SYNTHESIS OF COMPOUND 43)

All of the resulting compound 43A and an aqueous solution of 590 g (4.25 mol) of bromoacetic acid which had been neutralized with 50% sodium hydroxide were added, thoroughly stirred, and left standing at room temperature overnight. An activated carbon was added to the reaction liquid to carry out a Celite filtration, and the pH was adjusted to 1.5 with concentrated hydrochloric acid. After the salt was removed by electrodialysis, the reaction liquid was concentrated in vacuo and then left standing overnight. The separated crystal was filtered off, and washed with water and with acetone. Thermal dying (45° C.) gave 130 g of an intended compound (yield: 55%).

Melting point: 174°–175° C. (decomposed).

Elemental Analysis: as $C_{13}H_{22}N_2O_8=334.33$

|  | H (%) | C (%) | N (%) |
|---|---|---|---|
| Calculated | 6.63 | 46.70 | 8.38 |
| Determined | 6.49 | 46.37 | 8.41 |

SYNTHETIC EXAMPLE 13

SYNTHESIS OF COMPOUND 36

Scheme 7

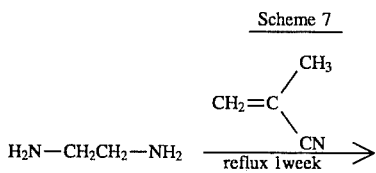

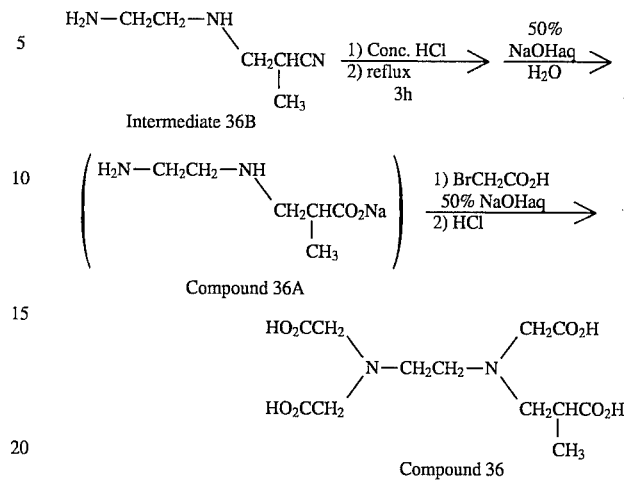

Compound 36

(SYNTHESIS OF COMPOUND 36A)

In a three-neck flask were incorporated 50.0 g (0.831 mol) of ethylenediamine and 223 g (3.324 mol) of methacrylonitrile, and the mixture was thermally refluxed for 1 week. Vacuum distillation (20 mmHg, 140°–160° C.) gave intermediate 36B. Into a round bottom flask was incorporated 50 g (0.393 mol) of intermediate 36B, the content was thoroughly stirred with cooling on an ice bath, and 200 ml of concentrated hydrochloric acid was added dropwise through an isotactic dropping funnel over a period of 15 minutes. After the addition, the mixture was thermally refluxed on an oil bath for 3 hours. The solvent was removed in vacuo, a small amount of water and an aqueous 50% sodium hydroxide solution were added to the content to be a strong alkali (pH: 13 or more). The formed free ammonia was removed in vacuo to obtain compound 36A.

(SYNTHESIS OF COMPOUND 36)

All of the resulting compound 36A and an aqueous solution of 273 g (1.97 mol) of bromoacetic acid which had been neutralized with 50% sodium hydroxide were added, thoroughly stirred, and left standing at room temperature overnight. An activated carbon was added to the reaction liquid to carry out a Celite filtration, and the pH was adjusted to 1.5 with concentrated hydrochloric acid. After the salt was removed by electrodialysis, the reaction liquid was concentrated in vacuo and then left standing overnight. The separated crystal was filtered off, and washed with water and with acetone. Thermal dying (45° C.) gave 35 g of an intended compound (yield: 28%).

Melting point: 193°–195° C. (decomposed).

Elemental Analysis: as $C_{12}H_{20}N_2O_8=320.30$

|  | H (%) | C (%) | N (%) |
|---|---|---|---|
| Calculated | 6.29 | 45.00 | 8.75 |
| Determined | 6.07 | 44.78 | 8.73 |

SYNTHETIC EXAMPLE 14

SYNTHESIS OF COMPOUND 34

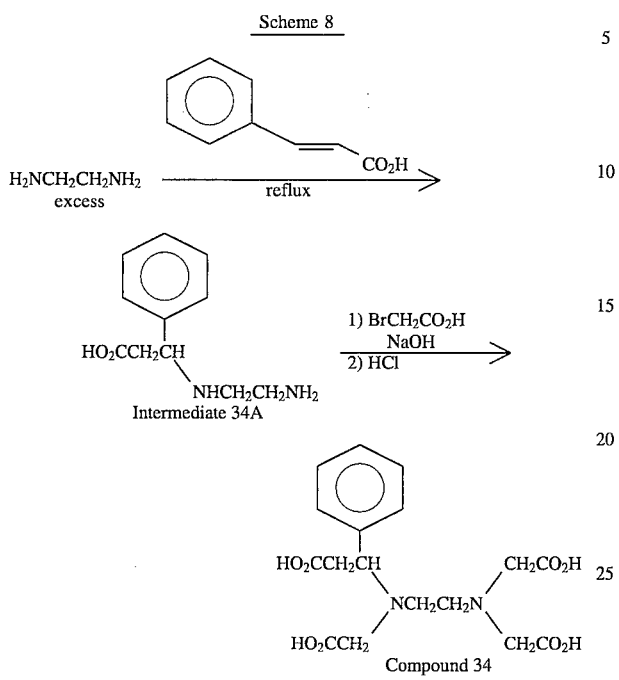

Compound 34

In a three-neck flask were incorporated 100 g (0.679 mol) of cinnamic acid and 811 g (13.5 mol) of ethylenediamine, and the mixture was thermally refluxed for 5 hours. Ethylenediamine was distilled off in vacuo, 200 ml of dichloromethane was added and the mixture was thoroughly stirred. The separated crystal was filtered off, washed with dichloromethane and with methanol, and then thermally dried (45° C.).

In a three-neck flask were incorporated 57 g (0.274 mol) of the resulting intermediate 34A and 100 ml of water, and 190 g (1.37 mol) of an aqueous bromoacetic acid solution which had been previously neutralized was added. An aqueous 49% sodium hydroxide solution was added, and the reaction liquid was stirred for 12 hours while maintaining the pH at 9–11. An activated carbon was added to the reaction liquid in an amount of 2 g to carry out a Celite filtration, and the pH was adjusted to 1.5 with concentrated hydrochloric acid. After the salt was removed by electrodialysis, the solvent was concentrated in vacuo, and left standing in a refrigerator for 1 week. The separated crystal was filtered off, washed with a small amount of water and with acetone, and then dried in vacuo. This gave 64 g of the captioned compound (yield: 61%).

SYNTHETIC EXAMPLE 15

SYNTHESIS OF COMPOUND 45

Scheme 9

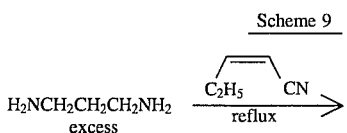

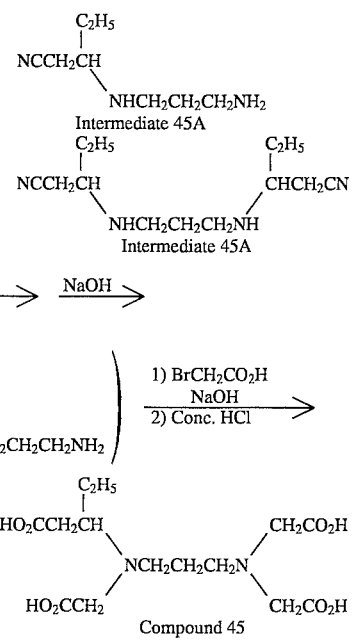

Compound 45

In a three-neck flask were incorporated 200 g (2.70 mol) of 1,3-propanediamine and 438 g (5.40 mol) of cis-2-pentenenitrile, and the mixture was thermally refluxed. After an excessive amount of the raw material was distilled off under a reduced pressure with an aspirator, pressure was reduced with a vacuum pump to obtain 157 g (1.01 mol) of intermediate 45A at 2 mmHg and at 124°–140° C. and 59 g (0.250 mol) of intermediate 46A at 2 mmHg and at 160°–190° C.

Into a three-neck flask was incorporated 100 g (0.644 mol) of intermediate 45A, and the content was thoroughly stirred with cooling on an ice bath, and 300 g (2.96 mol) of 36% hydrochloric acid was added dropwise over a period of 30 minutes. After thermally refluxing on an oil bath for 3 hours, the solvent was distilled off in vacuo. After 200 ml of water was added and thoroughly stirred, the pH was adjusted to a strong alkali (pH: 12 or more) with an aqueous 50% sodium hydroxide solution. Ammonia was removed in vacuo, 447 g (3.22 mol) of an aqueous bromoacetic acid solution which had been previously neutralized was added, and stirred at room temperature for 12 hours while maintaining the pH at 9–10 with an aqueous 50% sodium hydroxide solution. To the reaction liquid was added 4 g of an activated carbon to carry out Celite filtration, and the pH was adjusted to 1.5 with hydrochloric acid. After the salt was removed by electrodialysis, the solvent was concentrated in vacuo, and left standing in a refrigerator for 1 week. The separated crystal was filtered off, washed with a small amount of water and with acetone, and then dried in vacuo. This gave 144 g of the captioned compound (yield: 64%).

Melting point: Gradually decomposed from 140° C.

SYNTHETIC EXAMPLE 16

SYNTHESIS OF COMPOUND 46

Scheme 10

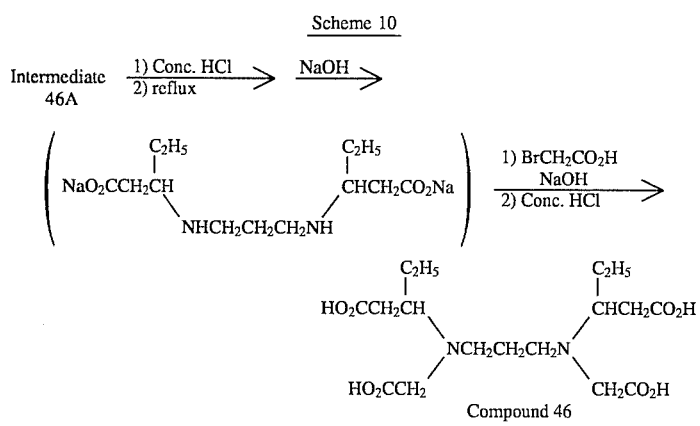

Into a three-neck flask was incorporated 50 g (0.212 mol) of intermediate 46A obtained in Synthetic Example 15, the content was thoroughly stirred with cooling on an ice bath, and 200 g (1.97 mol) of hydrochloric acid was added dropwise over a period of 30 minutes. After thermally refluxing on an oil bath for 3 hours, the solvent was distilled off in vacuo. After 200 ml of water was added and thoroughly stirred, the pH was adjusted to a strong alkali (pH: 12 or more) with an aqueous 50% sodium hydroxide solution. Ammonia was removed in vacuo, 118 g (0.848 mol) of an aqueous bromoacetic acid solution which had been previously neutralized was added, and stirred at room temperature for 12 hours while maintaining the pH at 9–10 with an aqueous 50% sodium hydroxide solution. To the reaction liquid was added 3 g of an activated carbon to carry out Celite filtration, and the pH was adjusted to 1.5 with hydrochloric acid. After the salt was removed by electrodialysis, the solvent was concentrated in vacuo, and left standing in a refrigerator for 1 week. The separated crystal was filtered off, washed with a small amount of water and with acetone, and then dried in vacuo. This gave 70 g of the captioned compound (yield: 85%).

Melting point: Gradually decomposed from 110° C.

SYNTHETIC EXAMPLE 17

SYNTHESIS OF COMPOUND 11

In 300 ml of methanol was dissolved 19 g (0.316 mol) of ethylenediamine, then 100 g (0.666 mol) of benzoylformic acid and 46 g (0.344 mol) of calcium carbonate were added, and the mixture was thermally refluxed for 2 days. After cooling, 2 g of 10% palladium carbon-carbon catalyst was added to carry out hydrogenation in an autoclave (hydrogen pressure: 110 kg/cm$^2$). After a prescribed amount of hydrogen was consumed, 300 ml of water was added to the reaction liquid, and Celite filtration was carried out. After the solvent was completely distilled off in vacuo, the residue was dissolved in 500 ml of water, and the pH was adjusted to 6 with concentrated hydrochloric acid. The separated crystal was filtered off, and washed with water. All of the resulting crystal, 176 g (1.26 mol) of an aqueous bromoacetic acid solution which had been previously neutralized with an aqueous 50% sodium hydroxide solution and 500 ml of water were incorporated in a three-neck flask, and thoroughly stirred. While maintaining the pH at 8–10 with an aqueous 50% sodium hydroxide solution, stirring was carried out for 12 hours. To the reaction liquid was added 3 g of an activated carbon to carry out Celite filtration, the pH was adjusted to 6 with concentrated hydrochloric acid, and the separated crystal was filtered off. The resulting crystal was suspended in 300 ml of water, then dissolved therein by the addition of an aqueous 50% sodium hydroxide solution, and the pH was adjusted to 6 with concentrated hydrochloric acid. The separated crystal was filtered off, and washed with water and with acetone to obtain 28 g an intended compound 11 as monosodium salt (yield 20%).

Melting Point: 196°–198° C.

SYNTHETIC EXAMPLE 18

SYNTHESIS OF COMPOUND 44

Into a three-neck flask were incorporated 25.0 g (0.090 mol) of ethylenediamine-N,N'-dipropionic acid dihydrochloride (produced by Tokyo Kasei) and 50 ml of water, and the content was cooled on an ice bath. With thoroughly stirring, 29.0 g (0.36 mol) of an aqueous 50% sodium hydroxide solution was added dropwise. Into a beaker 60.1 g (0.360 mol) of 2-bromobutanoic acid was weighed, 50 ml of water was added, and the content was thoroughly stirred on an ice bath. While maintaining the inner temperature at 10° C. or less, 57.6 g (0.72 mol) of aqueous 50% sodium hydroxide solution was added dropwise. The solution was poured in the above-mentioned three-neck flask, and the mixture was stirred at room temperature for 5 hours. After left standing overnight, the reaction liquid was filtered, the pH value was adjusted to approximately 1.5 with concentrated hydrochloric acid. After being concentrated in vacuo until the reaction liquid was approximately 200 ml, the salt was removed by electrodialysis, and the separated white crystal was filtered off. After washing with water, the crystal was poured into a beaker, 50 ml of water was added thereto, and the crystal was dissolved by the addition of an aqueous 50% sodium hydroxide solution with thoroughly stirring. After the pH was adjusted to approximately 1.5 with concentrated hydrochloric acid and it was left standing overnight, the separated solid was filtered off. Washing with a small amount of water and with acetone and drying in vacuo gave 10.9 g (0.029 mol) of an intended compound 44.

Yield: 32%

Melting point: 190°–191° C.

SYNTHETIC EXAMPLE 19

SYNTHESIS OF COMPOUND 49

Into a three-neck flask were incorporated 25.0 g (0.090 mol) of ethylenediamine-N,N'-dipropionic acid dihydrochloride (produced by Tokyo Kasei) and 50 ml of water, and the content was cooled on an ice bath. With thoroughly stirring, 29.0 g (0.36 mol) of an aqueous 50% sodium hydroxide solution was added dropwise. Into a beaker 65.2 g (0.360 mol) of 2-bromopentanoic acid was weighed, 50 ml of water was added, and the content was thoroughly stirred on an ice bath. While maintaining the inner temperature at 10° C. or less, 57.6 g (0.72 mol) of aqueous 50% sodium hydroxide solution was added dropwise. The solution was poured in the above-mentioned three-neck flask, and the mixture was stirred at room temperature for 5 hours. After left standing overnight, the reaction liquid was filtered, the pH value was adjusted to approximately 1.5 with concentrated hydrochloric acid. After being concentrated in vacuo until the reaction liquid was approximately 200 ml, the salt was removed by electrodialysis, and the separated white crystal was filtered off. Washing with water and with acetone, and drying in vacuo gave 17.8 g (0.044 mol) of an intended compound 49.

Yield: 49%

Melting point: 182°–183° C. (decomposition)

Other compounds can be synthesized in a similar manner.

Of the iron complexes of the present invention, preferable compounds are those represented by the following formula (I-a):

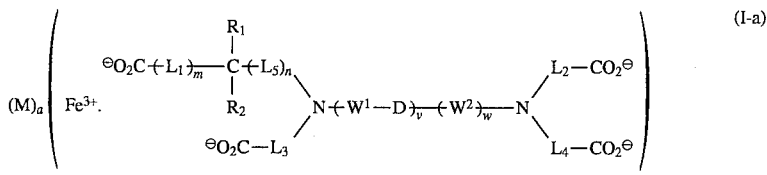

wherein $R_1$, $R_2$, $L_1$, $L_2$, $L_3$, $L_4$, $L_5$, m, n, $W^1$, $W^2$, D, v and w have the same meanings as those in formula (I), and the same being applicable to the preferred ranges, M is hydrogen or a cation, and a is a number defined so that the iron complex becomes neutral.

Of the iron complexes of the present invention, more preferable compounds are those represented by the following formula (I-b):

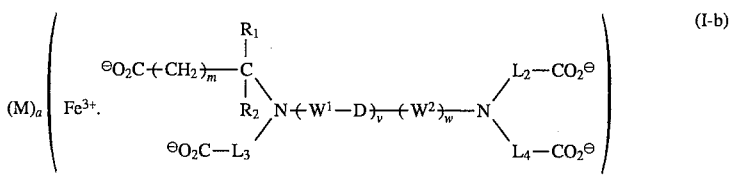

wherein $R_1$, $R_2$, $L_2$, $L_3$, $L_4$, m, $W^1$, $W^2$, D, v, w, M and a have the same meanings as those in formula (I-a), and the same being applicable to the preferred ranges.

Of the iron complexes of the present invention, still more preferable compounds are those represented by the following formula (I-c):

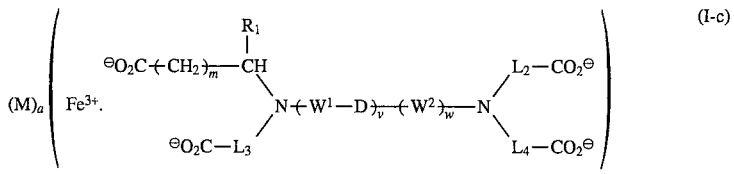

wherein $R_1$, $L_2$, $L_3$, $L_4$, m, $W^1$, $W^2$, D, v, w, M and a have the same meanings as those in formula (I-a), and the same being applicable to the preferred ranges.

Of the iron complexes of the present invention, still more preferable compounds are those represented by the following formula (I-d) or (I-e):

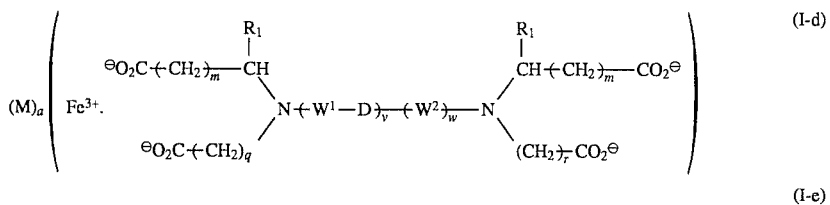

(I-d)

(I-e)

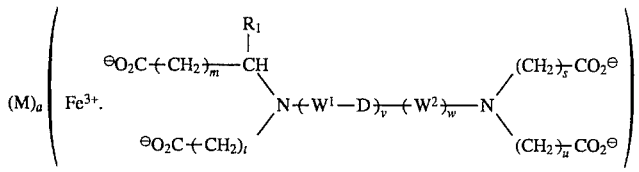

wherein $R_1$, m, $W^1$, $W^2$ D, v, w, N and a have the same meanings as those in formula (I-a), and the same being applicable to the preferred ranges, q, r, s, t, and u are independently 1 or 2, and when m=1, q, r, s, t, and u are preferably 1.

Of the compounds represented by formula (I) of the present invention, particularly preferable compounds are those represented by the following formula (I-f), (I-g), or (I-h):

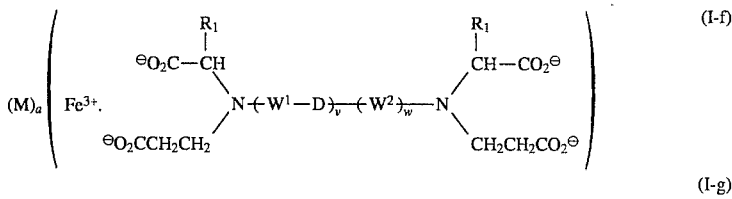

(I-f)

(I-g)

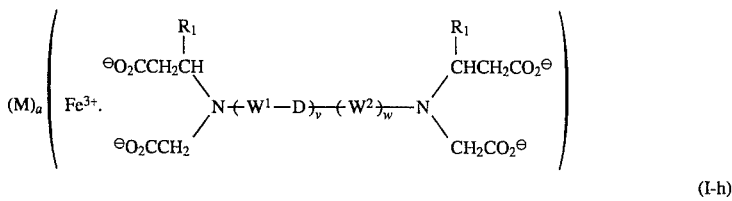

(I-h)

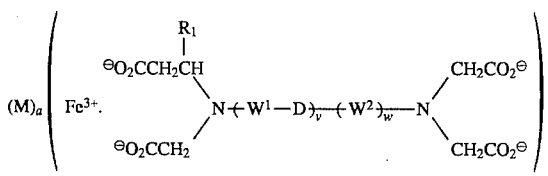

wherein $R_1$, $W^1$, $W^2$, D, v, w, M and a have the same meanings as those in formula (I-a), and the same being applicable to the preferred ranges.

Typical examples of the iron complexes of the present invention include, but are not restricted to:

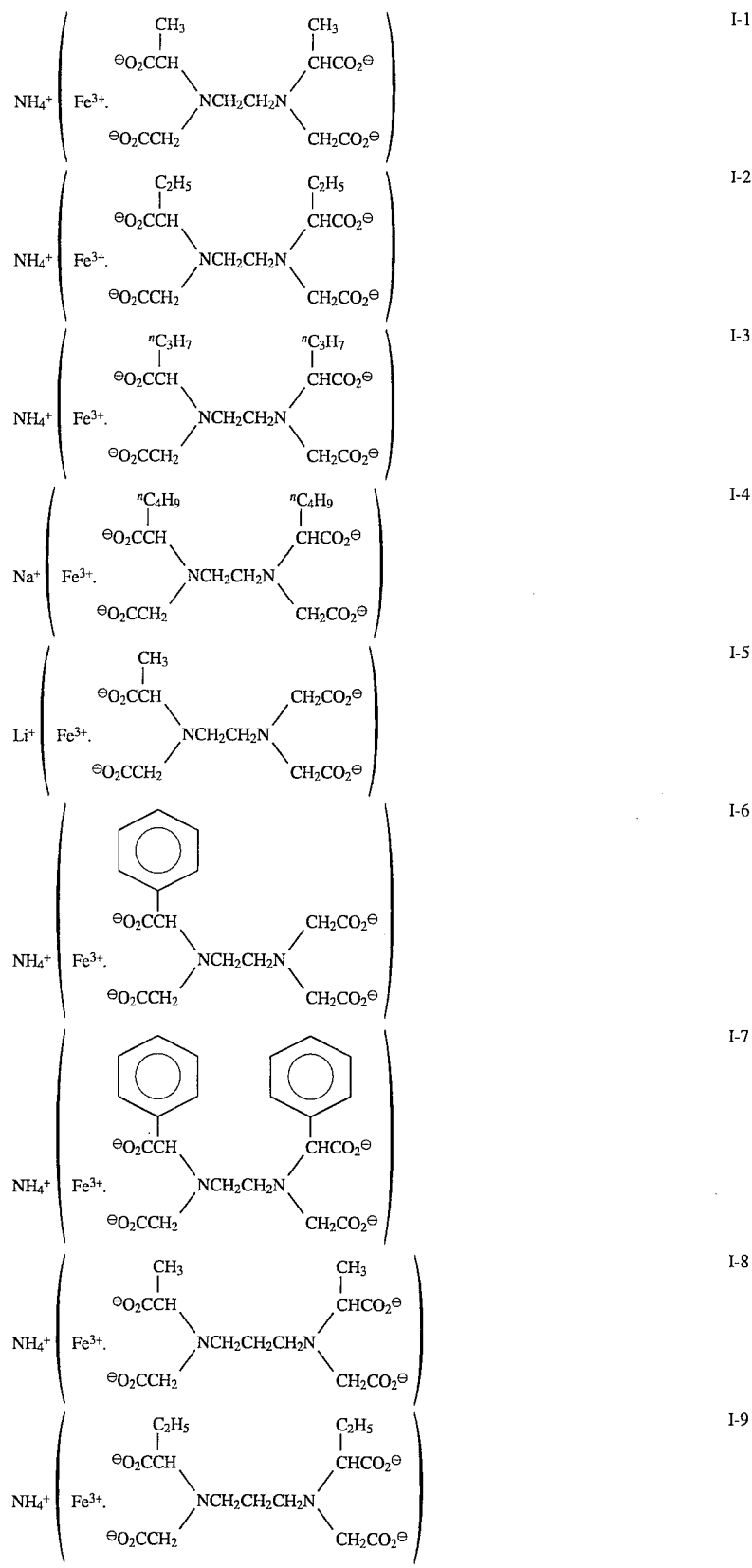

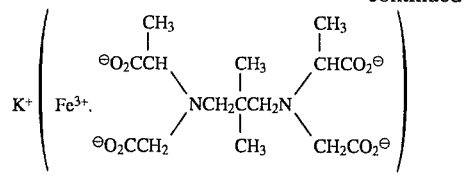 I-10
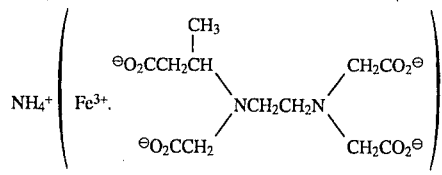 I-11
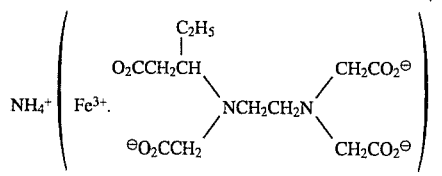 I-12
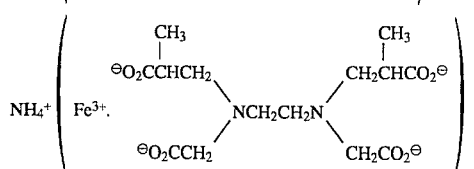 I-13
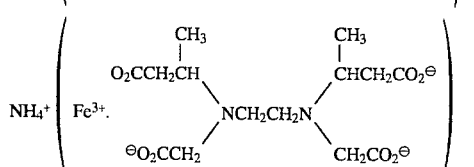 I-14
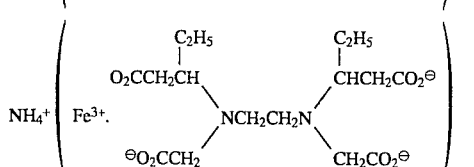 I-15
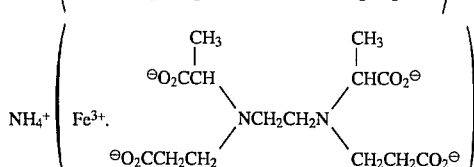 I-16
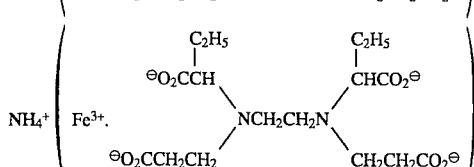 I-17
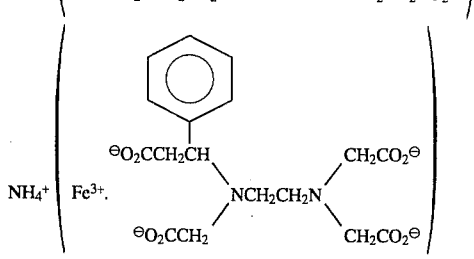 I-18

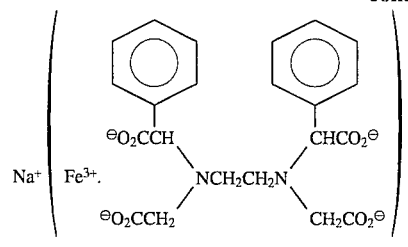
I-19
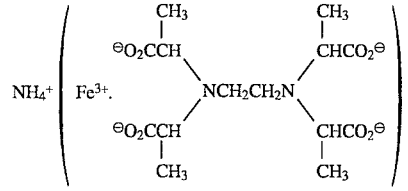
I-20
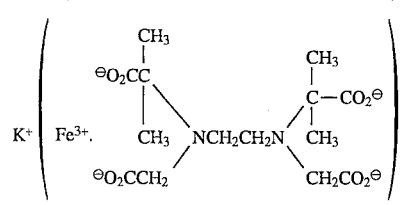
I-21
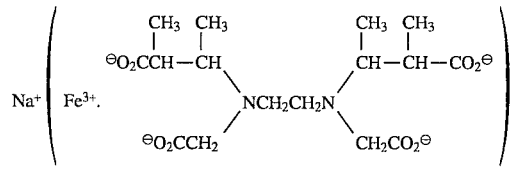
I-22
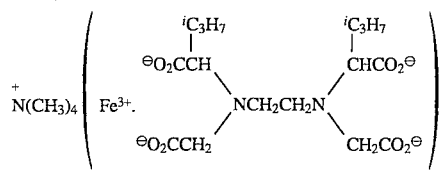
I-23
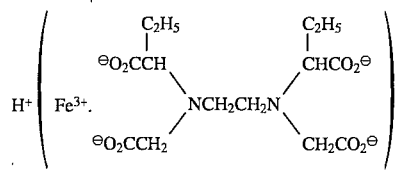
I-24
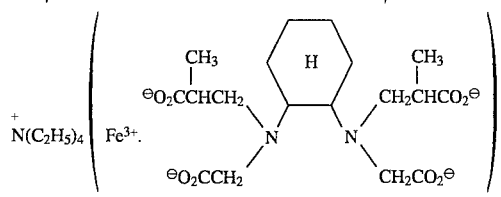
I-25
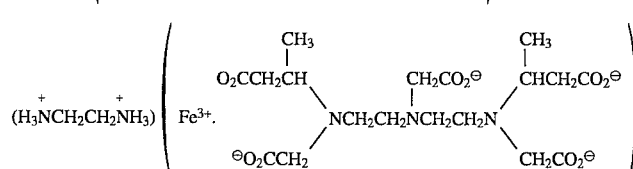
I-26
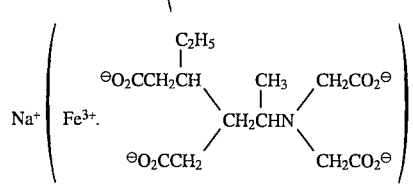
I-27

I-28 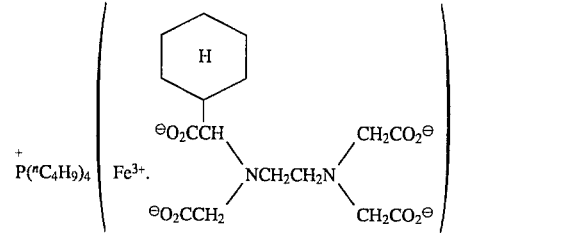
I-29 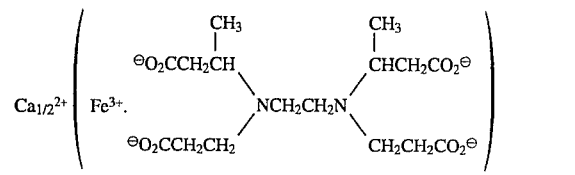
I-30 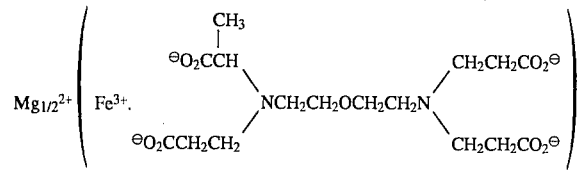
I-31 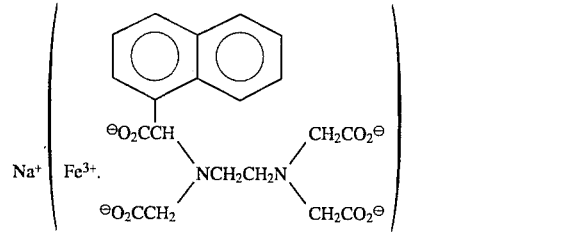
I-32 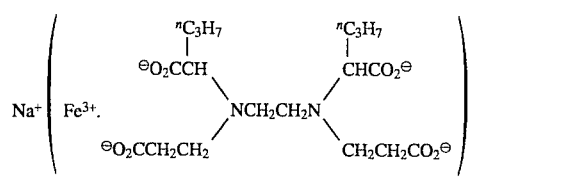
I-33 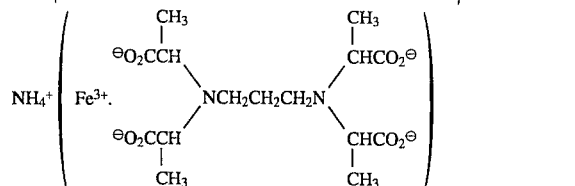
I-34 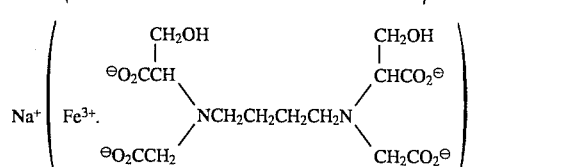
I-35 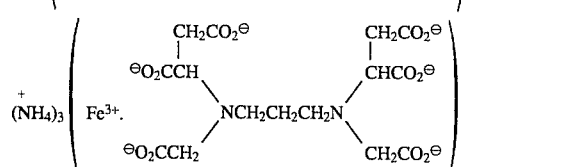
I-36 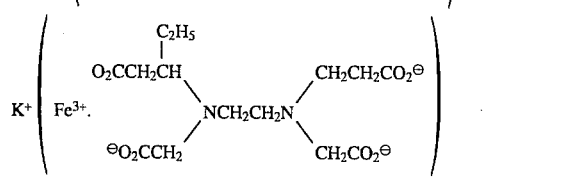

-continued

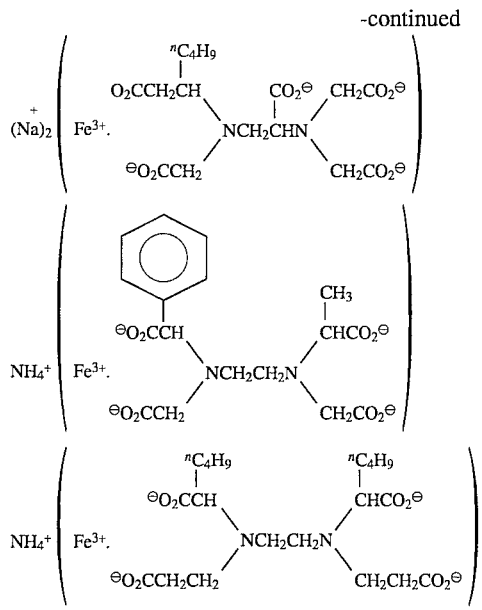

I-37

I-38

I-39

The iron complexes of the present invention may of course form hydrates.

The process for synthesizing the iron complex of the present invention will now be described.

The iron complex of the present invention can be synthesized by reacting a compound represented by formula (I) with an iron salt.

Examples of the iron salts to be reacted with a compound represented by formula (I) include ferric sulfate, ferric chloride, ferric nitrate, ferric ammonium sulfate, ferric phosphate, ferric oxide, triiron tetraoxide, iron hydroxide, etc. Furthermore, a compound may be reacted with a ferrous salt, and then converted into a ferric complex by oxidization to be a ferric complex. In this case, an oxidizing process is not specifically restricted and, for example, air, an oxygen gas, hydrogen peroxide, etc. may be used.

The compound represented by formula (I) is preferably used in an amount of from 0.1 to 5 mol, more preferably from 1 to 2 mol, and particularly from 1 to 1.5 mol, per mol of iron salt.

The amounts of the compound represented by formula (I) and of the iron salts each are from 0.001 to 2 mol/l, and preferably from 0.01 to 1.5 mol/l.

The solvent used here is not specifically restricted as long as it does not participate in the reaction, and examples include water, alcohols (methanol, ethanol, 2-propanol, butanol, pentanol, etc.), dioxane, dimethylformamide, etc. Preferable are water and alcoholic solvents, with water being particularly preferable.

In this reaction, in order to dissolve the compound represented by formula (I), which is a ligand, and the resulting iron complex, a base (e.g., an aqueous ammonia, sodium hydroxide, potassium hydroxide, sodium hydrogen carbonate, potassium hydrogen carbonate, sodium carbonate, potassium carbonate, etc.) is preferably added to adjust the pH value to 3–12, more preferably 3–8, and particularly 4–7. The reaction is usually carried out at a temperature of from 0° to 100° C., preferably from 10° to 80° C.

The reaction is usually carried out for 10 minutes to 24 hours, although the reaction period depends upon the kind of complex to be synthesized.

The isolation of the iron complex of the present invention can be carried out in a usual process, in which case, the adjustment of the pH value is important. If the pH is too low, no stable complex can be formed, and conversely, if it is too high, the isolation of the intended iron complex is difficult due to the formation of hydroxide complex having a high solubility or spearingly soluble iron hydroxide. From such a viewpoint, the synthesis of the iron complex of the present invention can be carried out at a pH level of from 0.5 to 12, but preferably from 1 to 10, and more preferably from 1 to 7.

For the adjustment of the pH value at this time, an acid (e.g. nitric acid, sulfuric acid, hydrochloric acid) or a base (e.g. an aqueous ammonia, sodium hydroxide, potassium hydroxide, sodium hydrogen carbonate, potassium hydrogen carbonate, sodium carbonate, potassium carbonate etc.) may be used.

When the iron complex is isolated, a usual concentrating may be carried out or a solvent such as an alcohol may be used.

The compound of the present invention is isolated as a crystal, which makes it possible to put into various applied field of iron complex.

The meal salt constructing the metal chelate compound of the compound represented by formula (I) of the present invention (hereinafter sometimes referred to as "chelate compound") is Fe (III) (such as ferric sulfate, ferric chloride, ferric nitrate, ferric ammonium sulfate, or ferric phosphate), but may be Mn (III), Co (III), Rh (II), Rh (III), Au (II), Au (III) and Ce (IV) may be mentioned. Of these, preferred are Fe (III) and Co (III), with Fe (III) being more preferred.

As the metal chelate compound of the present invention, one which is isolated as a metal chelate may be used, or a compound represented by formula (I) and the metal salt may be reacted in a solution to be used. Similarly, an ammonium or an alkali metal salt (e.g., lithium salts, sodium salts, potassium salts) of the compound represented by formula (I) may be reacted with the metal salt in a solution to be used.

The compound represented by formula (I) is used in a molar ratio relative to the metal ion of not less than 1.0. This ratio is preferably large if the stability of the metal chelate compound is low, and usually used in the range of from 1 to 30.

The compound represented by formula (I) according to the present invention may be incorporated in a photosensitive material (e.g., a hydrophilic colloidal layer, silver halide emulsion layer) as an additive for photography having no adverse influence upon the photographic characteristics (e.g., sensitivity, fogging), or may incorporated in a processing composition using therefor.

The use of the compound can provide functions of a chelating agent, a bleaching agent, an oxidizing agent, a precipitation proofing agent, a stain inhibitor, a stabilizer, a reducing agent, etc.

The metal chelate compound of the present invention has an effect as an oxidizing agent for a silver halide photosensitive material (e.g., a bleaching agent and a reducing agent, particularly a bleaching agent for a color photosensitive material).

According to a preferred embodiment of a processing composition containing the metal chelate compound of the present invention, when a silver halide photosensitive material having been imagewise exposed is color-developed, which is then processed with a processing solution at least containing the metal chelate compound of the present invention as a bleaching agent, the bleaching of developed silver is carried out very rapidly. Also, these are a little precipitation, staining of the surface of photosensitive material, and blockage of a filter, which can be seen in the conventional bleaching agent capable of rapidly carrying out bleaching.

The present invention is an invention which is characterized by a bleaching agent in a processing composition having a bleaching ability, especially for a color photosensitive material as an oxidizing agent in a processing composition for photography, and other requirements such as for the materials can be appropriately selected from these which are generally applicable.

The processing compositions (processing solutions) containing the metal chelate compounds and chelating agent compounds of the present invention will now be described.

The metal chelate compound of the present invention may be incorporated in any processing solution (such as a bleach-fixing solution, a fixing solution, an intermediate bath between a color developing and a desilvering stages, or a stabilizing solution), and when it is incorporated in an amount of from 0.005 to 1 mol per liter of the processing solution, it is particularity effective as a reducing solution for a black-and-white photosensitive material or a processing solution, (bleaching solution or bleach-fixing solution) for a color photosensitive material having a bleaching power.

Preferred embodiments of the processing solutions having a bleaching power will now be described. As described above, when the metal chelate compounds of the present invention is contained in a processing solution having a bleaching ability in an amount of from 0.005 to 1 mol, preferably from 0.01 to 0.5 mol, and particularly from 0.05 to 0.5 mol, per liter of the processing solution, it is effective as a bleaching agent. The metal chelate compound of the present invention can also exhibit its excellent abilities, even if it is used in a dilute concentration of from 0.005 to 0.2 mol, preferably from 0.001 to 0.2 mol, and more preferably from 0.05 to 0.18 mol, per liter of the processing solution.

In the case of adding the metal chelate compound of the present invention to a processing solution having a bleaching ability, it can be added not only as an oxidized product thereof (e.g., a chelate compound of Fe (III)), but also as a reduced product (e.g., a chelate compound of Fe (II)).

When the metal chelate compound of the present invention is used as a bleaching agent in a processing solution having a bleaching ability, within a range where the effect of the present invention can be exhibited (preferably not less than 0.001 mol and not more than 0.3 mol, and more preferably not less than 0.01 mol and not more than 0.2 mol), any other bleaching agent may be co-used. The bleaching agents which can be used include polyvalent metal compounds such as iron (III), peroxides, quinones, nitro compounds, etc. Typical examples of the bleaching agents used include, but are not restricted to, organic complexes of iron (III), such as complexes with ethylenediaminetetraacetic acid, diethylenetriaminepentaacetic acid, cyclohexanediaminetetraacetic acid, methyliminodiacetic acid, and glycol ether diaminetetraacetic acid, bleaching agents as described on page 4, the lower right column to page 5, the upper left column of JP-A-4-121739, represented by iron complexes of 1,3-propylenediaminetetraacetic acid, carbamoyl type bleaching agents as described in JP-A-4-73647, bleaching agents having a heterocyclic ring as described in JP-A-4-174432, bleaching agents as described in EP-A-520457, represented by ferric complexes of N-(2-carboxyphenyl)iminodiacetic acid, bleaching agents as described in EP-A-530828, represented by ferric complexes of ethylenediamine-N-2-carboxyphenyl-N,N', N'-triacetic acid, bleaching agents as described in EP-A-501479, bleaching agents as described in EP-A- 567126, bleaching agents as described in JP-A-4-127145, ferric complexes of aminopolycarboxylic acids or salts thereof as described on page (11) of JP-A-3-144446, etc.

Preferred bleaching agents which are co-used with the metal chelate compound of the present invention are those which possess an oxidation-reduction electric potential between −150 mV to +50 mV (vs. SCE), and, for example, ferric complex of ethylenediaminetetraacetic acid can be mentioned.

In addition to containing the metal chelate compound as a bleaching agent, it is preferable for the processing solution having a bleaching ability containing the metal chelate compound according to the present invention to add a re-halogenating agent for accelerating the oxidization of silver such as a chloride, bromide, or iodide. Instead of the halide, an organic ligand which forms a sparingly soluble silver salt may be added. The halide is added as an alkali metal salt, an ammonium salt, or a salt of guanidine or amine. Typically, sodium bromide, ammonium bromide, potassium chloride, guanidine hydrochloride, potassium bromide, potassium chloride, etc. can be mentioned. In the processing solution having a bleaching ability of the present invention, an amount of re-halogenating agent is appropriately not more than 2 mol/liter, and in the case of the bleaching solution, it is preferably from 0.01 to 2.0 mol/liter, more preferably from 0.1 to 1.7 mol/liter, and particularly, from 0.1 to 0.6 mol/liter. In the bleach-fixing solution, the amount is preferably from 0.001 to 2.0 mol/liter, more preferably from 0.001 to 1.0 mol/liter, and particularly from 0.001 to 0.5 mol/liter.

To the bleaching solution or the bleach-fixing solution of the present invention, a bleaching accelerator, an anti-corrosive agent for preventing the corrosion of a processing tank, a buffer for maintaining the pH of the solution, a brightening agent, an anti-foaming agent, etc. may optionally be added.

As for the bleaching accelerators, for example, compounds having mercapto group or disulfide group as described in U.S. Pat. No. 3,893,858, German Patent No. 1,290,821, British Patent No. 1,138,842, JP-A-53-95630, and *Research Disclosure* No. 17129 (July, 1978), thiazolidine derivatives as described in JP-A-50-140129, thiourea derivatives as described in U.S. Pat. No. 3,706,561, iodides as described in JP-A-58-16235, polyethylene oxide compounds as described in German Patent No. 2,748,430, polyamine compounds as described in JP-B-45-8836, etc. may be used. Furthermore, compounds as described in U.S.

Pat. No. 4,552,834 are also preferable. These bleaching accelerators may be incorporated in the photosensitive material. In the case of bleach-fixing a color photosensitive material for photographing, these bleaching accelerators are particularly preferable. More preferable are mercapto compounds as described in British Patent No. 1,138,842 and JP-A-2-190856.

The pH value of the bleaching solution or the bleach-fixing solution of the present invention is from 2.0 to 8.0, and preferably from 3.0 to 7.5. When bleaching or bleach-fixing are carried out immediately after color development in a photosensitive material for photographing, it is advisable to use a solution at a pH value of not more than 7.0, and preferably not more than 6.4, in order to suppress the bleach fogging. Particularly, in the case of the bleaching solution, the pH value is preferably from 3.0 to 5.0. If the pH value is less than 2.0, the metal chelate of the present invention tends to become instable and, therefore, the pH value of from 2.0 to 6.4 is preferable. In the material for color print, a preferred pH range is from 3 to 7.

As the pH buffering agent for this purpose, any buffer can be used as long as it is difficult to be oxidized by the bleaching agent, and has a buffering function within the above-mentioned pH range. Examples include organic acids such as acetic acid, glycolic acid, lactic acid, propionic acid, butyric acid, malic acid, chloroacetic acid, levulinic acid, ureidopropionic acid, formic acid, pyruvic acid, isobutyric acid, pivalic acid, aminobutyric acid, valeric acid, isovaleric acid, asparagine, alanine, arginine, ethionine, glycine, glutamine, cysteine, serine, methionine, leucine, histidine, benzoic acid, hydroxybenzoic acid, nicotinic acid, oxalic acid, malonic acid, succinic acid, tartaric acid, maleic acid, fumaric acid, oxaloic acid, glutaric acid, adipic acid, aspartic acid, glutamic acid, cystine, ascorbic acid, phthalic acid, and terephthalic acid, and organic bases such as pyridine, dimethylpyrazole, 2-methyl-o-oxazoline, aminoacetonitrile, and imidazole, etc. These buffers may be used in combination. In the present invention, an organic acid having an acid dissociation constant (pKa) of from 2.0 to 5.5 is preferable, and a dibasic acid is more preferable. Examples of particularly preferable dibasic acids are succinic acid, glutaric acid, maleic acid, fumaric acid, malonic acid, adipic acid, etc. Most preferable are succinic acid, glutaric acid and maleic acid. These organic acids can be used as alkali metal salts (e.g., lithium salts, sodium salts, potassium salts), or ammonium salts thereof. An appropriate amount of the buffer is not more than 3.0 mol, preferably from 0.1 to 2.0 mol, more preferably from 0.2 to 1.8 mol, and particularly from 0.4 to 1.5 mol, per liter of the processing solution having a bleaching ability.

In order to adjust the pH value of the processing solution having a bleaching ability to the above range, the above-mentioned acid and an alkali agent (e.g., aqueous ammonia, KOH, NaOH, potassium carbonate, sodium carbonate, imidazole, monoethanolamine, diethanolamine) may be jointly used. Of these, an aqueous ammonia, KOH, NaOH, potassium carbonate and sodium carbonate are preferable.

As the anti-corrosive agent, a nitrate such as ammonium nitrate, sodium nitrate, or potassium nitrate, is preferably used. An amount to be added is from 0.01 to 2.0 mol/liter, and preferably from 0.05 to 0.5 mol/liter.

From recent increasing understanding of the earth environmental safeguard, an effort has been made to reduce a nitrogen atom discharged into the environment. From such a viewpoint, it is desired that the processing solution of the present invention substantially contains no ammonium ion.

In the present invention, the term "substantially containing no ammonium ion" means the state where the concentration of ammonium ion is not more than 0.1 mol/liter, preferably not more than 0.08 mol/liter, more preferably not more than 0.01 mol/liter, and particularly no ammonium ion is contained at all.

In order to reduce the ammonium ion to the range of the present invention, an alkali metal ion, an alkaline earth metal ion is preferably used as a cation species instead. Of these lithium ion, sodium ion, and potassium ion are preferable, and typically, a sodium salt or a potassium salt of ferric complex of organic acid as a bleaching agent, potassium bromide or sodium bromide as a re-halogenating agent in the solution having a bleaching ability, as well as potassium nitrate, sodium nitrate, etc. can be mentioned.

As the alkali agent for adjusting a pH, potassium hydroxide, sodium hydroxide, potassium carbonate, sodium carbonate, etc. are preferable.

It is preferable for the processing solution having a bleaching ability of the present invention to carry out aeration in the processing, in terms of maintaining the photographic characteristics at a very stable level. In the aeration, means known in the art can be used and, for example, air-blowing or absorption of air utilizing an ejector can be carried out.

For air-blowing, air is preferably discharged into a solution through an air diffusing tube having fine pores. Such an air diffusing tube is widely used in an air-exposure tank in a processing of an active sludge, etc. With regard to the aeration, the content of Z-121, "Using Process", C-41, the third edition, published from Eastman Kodak (1982), page, BL-1-BL-2 can be utilized. In the processing using the processing solution having a bleaching ability of the present invention, stirring is preferably strengthened, and in order to carry out, the content of JP-A-3-33847, page 8, the upper right column, line 6 to the lower left column, line 2, can be utilized as is.

The bleaching stage or the bleach-fixing stage can be carried out at a temperature range of from 30° to 60° C., and preferably from 35° to 50° C.

The period of the bleaching stage and/or the bleach-fixing stage is in the range of from 10 seconds to 7 minutes, preferably from 10 seconds to 4 minutes in the photosensitive material for photographing. In the photosensitive material for print, the period is in the range of from 5 to 70 seconds, preferably from 5 to 60 seconds, and more preferably from 10 to 45 seconds. Under these preferable processing conditions, good results which are rapid and free of staining are obtained.

The photosensitive material having been processed with the processing solution having a bleaching ability is subjected to a fixing processing or a bleach-fixing processing. When the processing solution having a bleaching ability is a bleach-fixing solution, the subsequent fixing or bleach-fixing may or may not be carried out. For such a fixing solution or a bleach-fixing solution, that described in JP-A-3-33847, page 6, the lower right column, line 16 to page 8, the upper left column, line 15 is preferable.

As a fixer in the desilvering stage, ammonium thiosulfate has been generally used, but it may be substituted by the known other fixer such as a meso-ion compound, a thioether compound, a thiourea, a large amount of an iodide or hypo. These compounds are described in JP-A-60-61749, JP-A-60-147735, JP-A-64-21444, JP-A-1-201659, JP-A-1-210951, JP-A-2-44355, U.S. Pat. No. 4,378,424, etc. Examples include ammonium thiosulfate, sodium thiosulfate, potassium thiosulfate, guanidine thiosulfate, ammonium thiocyanate, sodium thiocyanate, potassium thiocyanate, dihydroxyethyl-thioether, 3,6-dithia-1,8-octane diol, imidazole, etc. Amongst them, thiosulfates and meso-ions are preferable. From the viewpoint of rapid fixing, ammonium thiosulfate is preferable, but from the viewpoint of substantially containing no ammonium ion associated with the environmental problem described above, sodium thiosulfate and meso-ions are more preferable. Furthermore, the combination of two or more fixers makes it possible to carry out rapid fixing. For example, together with ammonium thiosulfate or sodium thiosulfate, the above-mentioned ammonium thiocyanate, imidazole, thiourea, thioether, etc. may be preferably used. In this case, the second fixer may be preferably added in an amount of from 0.01 to 100 mol% based on ammonium thiosulfate or sodium thiosulfate.

An amount of the fixer is from 0.1 to 3.0 mol, and preferably from 0.5 to 2.0 mol, per liter of the bleach-fixing solution or the fixing solution. The pH value of the fixing solution which depends upon the kind of the fixer is generally from 3.0 to 9.0, and particularly when using a thiosulfate, it is preferably from 5.8 to 8.0 in terms of obtaining a stable fixing ability.

A preservative may be added to the bleach-fixing solution or the fixing solution to enhance the stability of the solution with the elapse of time. In the case of the bleach-fixing solution or the fixing solution containing a thiosulfate, sulfites, hydroxylamines, hydrazines and/or bisulfite-adducts of aldehyde (e.g., bisulfite-adduct of acetaldehyde, and particularly bisulfite-adducts of aromatic aldehyde described in JP-A-1-298935) are effective as the humectants.

It is preferable to contain at least one sulfinic acid or a salt thereof in the bleach-fixing solutions containing the metal chelate compound of the present invention. Preferred examples of the sulfinic acids and salts thereof include compounds as described in JP-A-1-230039, JP-A-1-224762, JP-A-1-231051, JP-A-1-271748, JP-A-2-91643, JP-A-2-251954, JP-A-2-251955, JP-A-3-55542, JP-A-3-158848, JP-A-4-51237, JP-A-4-329539, U.S. Pat. No. 5,108,876 and 4,939,072, EP-A-255722 and EP-A-463639, etc., more preferably are arylsulfinic acids which may be substituted, or salts thereof, and particularly phenylsulfinic acids which may be substituted, or salts thereof. Examples of the substituents include alkyl groups having 1 to 4 carbon atoms, aryl groups having 6 to 10 carbon atoms, carbamoyl groups having 1 to 5 carbon atoms, alkoxycarbonyl groups having 1 to 5 carbon atoms, alkoxy groups having 1 to 4 carbon atoms, sulfinic acid groups, sulfonic acid group, carboxylic acid group, hydroxy group, halogen atoms, etc.

Preferred examples of sulfinic acids and salts thereof include, but are not restricted to:

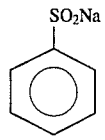
S-1

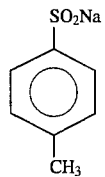
S-2

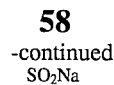
S-3

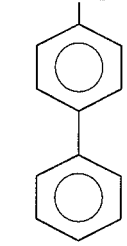
S-4

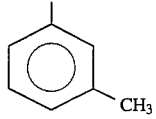
S-5

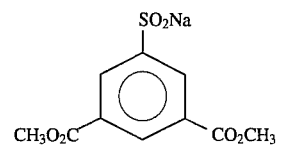
S-6

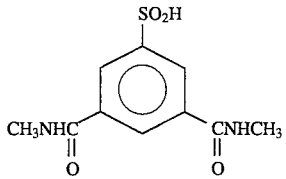
S-7

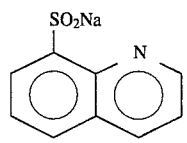
S-8

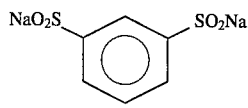
S-9

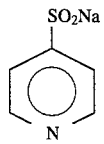
S-10

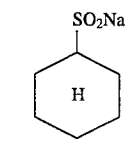
S-11

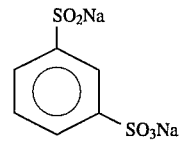
S-12

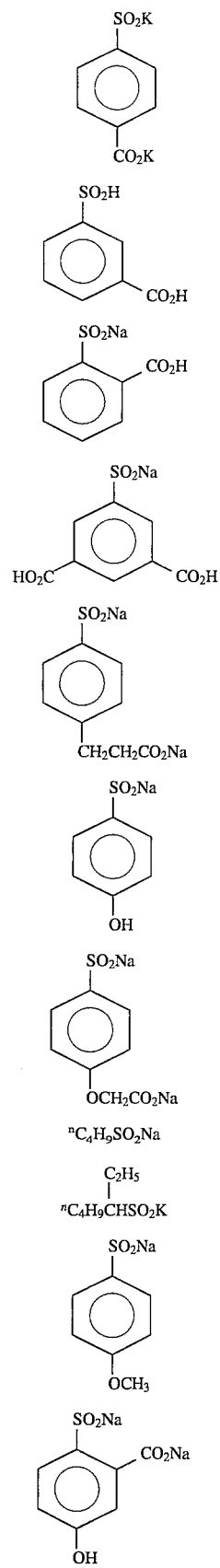

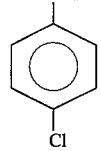

An amount of the sulfinic acids or salts thereof added to the bleach-fixing solution or the fixing solution is from $1\times10^{-4}$ to 1 mol, preferably from $1\times10^{-3}$ to 0.5 mol, and more preferably from $1\times10^{-2}$ to 0.1 mol, per liter of the processing solution.

In order to keep the pH value of the bleach-fixing solution or the fixing solution at constant, a buffer is preferably added. Examples include phosphates, imidazoles such as imidazole, 1-methyl-imidazole, 2-methyl-imidazole, and 1-ethyl-imidazole, triethanolamine, N-allylmorpholine, N-benzoylpiperazine, and the like.

Furthermore, in the fixing solution, the iron ion carried over from the bleaching solution can be masked by the addition of various chelating agents so as to enhance the stability of the solution. Examples of such chelating agents, apart from the compounds of the present invention, include 1-hydroxyethylidene-1,1-diphosphonic acid, nitrilotrimethylenephosphonic acid, 2-hydroxy-1,3-diaminopropanetetraacetic acid, ethylenediaminetetraacetic acid, diethylenetriaminepentaacetic acid, ethylenediamine-N-(β-hydroxyethyl)-N,N',N''-triacetic acid, 1,2-diaminopropanetetraacetic acid, 1,3-diaminopropanetetraacetic acid, nitrilotriacetic acid, cyclohexanediaminetetraacetic acid, iminodiacetic acid, dihydroxyethylene glycine, ethyl ether diaminetetrapropionic acid, glycol ether diaminetetraacetic acid, ethylenediaminetetrapropionic acid, phenylenediaminetetraacetic acid, 1,3-diamino-2-propanol-N,N,N', N'-tetramethylenephosphonic acid, ethylenediamine-N,N,N', N'-tetramethylenephosphonic acid, 1,3-propanediamine-N,N,N', N'-tetramethylenephosphonic acid, serine-N,N-diacetic acid, 2-methylserine-N,N-diacetic acid, 2-hydroxymethylserine-N,N-diacetic acid, hydroxyethyliminodiacetic acid, methyliminodiacetic acid, N-(2-acetamido)iminodiacetic acid, nitritotripropionic acid, ethylenediaminediacetic acid, ethylenediaminedipropionic acid, 1,4-diaminobutanetetraacetic acid, 2-methyl-1,3-diaminopropanetetraacetic acid, 2,2-dimethyl-1,3-diaminopropanetetraacetic acid, alanine, tartaric acid, hydrazidediacetic acid, N-hydroxy-iminodipropionic acid, and alkali metal salts thereof (e.g., lithium salts, sodium salts, potassium salts) and ammonium salts thereof.

The fixing stage can be carried out at a temperature of from 30° to 60° C., and preferably from 35° to 50° C..

The period of the fixing processing stage is from 15 seconds to 2 minuets, and preferably from 25 seconds to 1 minute and 40 seconds in a photosensitive material for photographing, and from 8 to 80 seconds, and preferably from 10 to 45 seconds, in a photosensitive material for print.

The desilvering stage is generally carried out in combination with the bleaching stage, the bleach-fixing stage and fixing stage. Typical examples are as follows:

(1) Bleaching→Fixing
(2) Bleaching→Bleach-fixing
(3) Bleaching→Bleach-fixing→Fixing
(4) Bleaching→Water Washing→Fixing
(5) Bleach-fixing
(6) Fixing→Bleach-fixing In a photosensitive material for photographing, (1), (2), (3), (4), and (5) are preferable, and in the present invention, significant effects are exhibited in the stages containing the bleach-fixing solution as in (2), (3), and (5), with (5) being particularly preferred.

The present invention is also applicable to the desilvering stage after color development via a regulating bath, a stopping bath, a water washing bath, etc.

The processing solution having a bleaching ability of the present invention can be reused after the overflow solution used in the processing is recovered, and the composition is adjusted by adding required components. Such a using method is usually called regeneration, and in the present invention, such regeneration can be preferably carried out. For the detail of the regeneration, the content of Fuji Film Processing Manual, Fuji Color Negative Film, CN-16 Processing (revised on August, 1990), pages 39–40, published from Fuji Film Co., Ltd. is applicable.

A kit for preparing the processing solution having a bleaching ability of the present invention may be a solution or a solid, but in the case of excluding an ammonium salt, almost all of the raw materials are supplied as powder, and because of low hygroscopicity, the preparation of powder becomes easy.

From the viewpoints of reducing the amount of the waste liquid, the kit for the regeneration is preferably powder because no excessive water is used and it can be directly added.

With regard to the regeneration of the processing solution having a bleaching ability, in addition to the above-mentioned aeration, a process described in "Syashin Kogaku No Kiso, -Gin-en Syashin Hen- (Foundation of Photographic Engineering, -Silver Salt Photograph-", (Nippon Photograph Meeting, Ed., Corona Publishing Co. Ltd, 1979), etc. can be utilized. Specifically, in addition to electrolysis regeneration, processes for regenerating a bleaching solution using bromic acid or chlorous acid, bromine, bromine precursor, a persulfate, hydrogen peroxide, hydrogen peroxide with a catalyst, bromous acid, ozone, etc. can be mentioned.

In the regeneration by electrolysis, a cathode and an anode are incorporated in the same bath or a cathode tank and an anode tank are separated by a diaphragm to be regenerated, or alternatively, a bleaching solution and a developer and/or a fixing solution can be simultaneously regenerated using a diaphragm.

The regeneration of a fixing solution and bleach-fixing solution is carried out by electrolytically reducing the deposited silver ion. Otherwise, it is also preferable to remove the deposited halogen ion by an anion exchange resin in terms of maintaining a fixing ability.

In order to reduce the amount of washing water used, ion-exchanging or ultrafiltration is used, and particular preference is given to the use of ultrafiltration.

The present invention is also applicable as a reducing solution which adjusts a silver image comprising a dot and/or line work obtained by exposing and developing a silver halide photosensitive material for photomechanical process.

The chelating agent compound represented by formula (I) can be applied to all of the processing compositions for processing a silver halide black-and-white photosensitive material and a silver halide color photosensitive material. As the silver halide black-and-white photosensitive material, examples include, but are not restricted to, a general-purpose black-and-white developer, an infectious developer for lithographic film, a fixing solution, washing water, etc., and as the silver halide color photosensitive material, examples include, but are not restricted to, a color developer, a bleaching solution, a fixing solution, a bleach-fixing solution, an adjusting solution, a stopping solution, a hardening solution, washing water, a stabilizing solution, a rinsing solution, a fogging solution, and toning solution, etc. The present invention is particularly effective in a black-and-white developer, a color developer, a fixing solution, and a stabilizing solution, and is of an excellent ability in a black-and-white developer and a color developer. The composition may be a solution or a solid such as a powder, a granule, or a tablet.

An amount of the compound represented by formula (I), which depends upon the processing composition to be added, is usually utilized in the range of from 10 mg to 50 g per liter of the processing composition.

More specifically, for example, in the case of adding to a black-and-white developer or a color developer, a preferable amount is from 0.5 to 10 g per liter of the processing solution, in the case of adding to a bleaching solution (e.g., comprising hydrogen peroxide, a persulfuric acid, bromic acid, etc.), it is from 0.1 to 20 g per liter of the processing solution, in the case of adding to a fixing solution or a bleach-fixing solution, it is from 1 to 40 g per liter of the processing solution, and in the case of adding to a stabilizing bath, it is from 50 mg to 1 g per liter of the processing solution.

The compound represented by formula (I) may be used singly or in combination of two or more thereof.

In a black-and-white developer or a color developer, the addition of the compound of the present invention intends to prevent a precipitate and to enhance the stability of the processing solution.

Examples of the color developers used in the present invention include those described in JP-A-3-33847, page 9, the upper left column, line 6 to page 11, the lower right column, line 6 and those described in JP-A-5-197107.

As the color developing agent in the color developing stage, known aromatic primary amine color developing agent is applicable, and a p-phenylenediamine compound is preferably used. Typical examples are 3-methyl-4-amino-N,N-diethylaniline, 3-methyl-4-amino-N-ethyl-N-β-hydroxyethylaniline, 3-methyl-4-amino-N-ethyl-N-β-methanesulfonamidoethylaniline, 3-methyl-4-amino-N-ethyl-N-β-methoxyethylaniline, 4-amino-3-methyl-N-methyl-N-(3-hydroxypropyl)aniline, 4-amino-3-methyl-N-ethyl-N-(3-hydroxypropyl)aniline, 4-amino-3-methyl-N-ethyl-N-(2-hydroxypropyl)aniline, 4-amino-3-ethyl-N-ethyl-N-(3-hydroxypropyl)aniline, 4-amino-3-methyl-N-propyl-N-(3-hydroxypropyl) aniline, 4-amino-3-propyl-N-methyl-N-(3-hydroxypropyl) aniline, 4-amino-3-methyl-N-methyl-N-(4-hydroxypropyl) aniline, 4-amino-3-methyl-N-ethyl-N-(4-hydroxybutyl) aniline, 4-amino-3-methyl-N-propyl-N-(4-hydroxybutyl) aniline, 4-amino-3-ethyl-N-ethyl-N-(3-hydroxy-2-methylpropyl) aniline, 4-amino-3-methyl-N,N-bis(4-hydroxybutyl)-aniline, 4-amino-3-methyl-N,N-bis(5-hydroxypentyl)aniline, 4-amino-3-methyl-N-(5-hydroxypentyl)-N-(4-hydroxybutyl)aniline, 4-amino-3-methoxy-N-ethyl-N-(4-hydroxybutyl)aniline, 4-amino-3-ethoxy-N,N-bis (5-hydroxypentyl)aniline,4-amino-3-propyl-N-(4-hydroxybutyl)aniline, and sulfates, hydrochlorides, and p-toluenesulfates thereof. Of these, 3-methyl-4-amino-N-ethyl-N-β-hydroxyethylaniline, 4-amino-3-methyl-N-ethyl-N-(3-hydroxypropyl)aniline, 4-amino-3-methyl-N-ethyl-N-(4-hydroxypropyl)aniline, and sulfates, hydrochlorides, and p-toluenesulfates thereof are preferable. Two or more these compounds can be jointly used according to an object.

Also, those described in EP-A-410450, JP-A-4-11255, etc. can be preferably utilized.

Also, salts such as sulfates, hydrochloride, sulfite, naphthalenedisulfonates, p-toluenesulfonates of these p-phenylenediamine derivatives may be used. An amount of the aromatic primary amine developing agent is preferably from 0.0002 to 0.2 mol, and more preferably from 0.001 to 0.1 mol, per liter of the color developer.

The processing temperature in the color developer of the present invention is from 20° to 55° C., and preferably from 30° to 55° C. The processing period is from 20 seconds to 5 minutes, preferably from 30 seconds to 3 minutes and 20 seconds, and more preferably from 1 minute to 2 minutes and 30 seconds, in a photosensitive material for photographing, and it is from 10 seconds to 1 minute and 20 seconds, preferably from 10 to 60 seconds, and more preferably from 10 to 40 seconds, in a photosensitive material for print.

To the color developer may optionally be added sulfites such as sodium sulfite, potassium sulfite, sodium bisulfite, potassium bisulfite, sodium metasulfite, and potassium metasulfite, and carbonyl-sulfite adducts as preservatives.

As compounds which directly preserve the aromatic primary amine color developing agent described above, various hydroxylamines (e.g., compounds as described in JP-A-63-5341 and JP-A-63-106655, particularly compounds having a sulfo group or a carboxy group), hydroxamic acids as described in JP-A-63-43138, hydrazines and hydrazides as described in JP-A-63-146041, phenols as described in JP-A-63-44657 and JP-A-63-58443, α-hydroxyketones and α-aminoketones as described in JP-A-63-44656 and/or various saccharides as described in JP-A-63-36244 are preferably added. In combination with these compounds, monoamines as described in JP-A-63-4235, JP-A-63-24254, JP-A-63-21647, JP-A-63-146040, JP-A-63-27841, JP-A-63-25654, etc., diamines as described in JP-A-63-30845, JP-A-63-14640, JP-A-63-43139, etc., polyamines as described in JP-A-63-21647, JP-A-63-26655, and JP-A-63-44655, nitroxy radicals as described in JP-A-63-53551, alcohols as described in JP-A-63-43140 and JP-A-63-53549, oximes as described in JP-A-63-56654, and tertiary amines as described in JP-A-63-23944 are preferably used.

As other preservatives, various metals as described in JP-A-57-44148 and JP-A-57-53749, salicylic acids as described in JP-A-59-180588, alkanolamines as described in JP-A-54-3582, polyethyleneimines as described in JP-A-56-94349, aromatic polyhydroxy compounds as described in U.S. Pat. No. 3,746,544 may optionally be contained. Particular preference is given to the addition of aromatic polyhydroxy compounds. An amount of these preservatives added is from 0.005 to 0.2 mol, and preferably from 0.01 to 0.05 mol, per liter of the color developer.

The color developer which is used in the present invention can be utilized at a pH level ranging from 9 to 12, and preferably from 9.5 to 11.5. In addition, compounds of known developing solution components may be contained in the color developer. In order to maintain the above-mentioned pH level, various buffers are preferably used.

Typical examples of the buffers include, but are not restricted to, sodium carbonate, potassium carbonate, sodium bicarbonate, potassium bicarbonate, trisodium phosphate, tripotassium phosphate, disodium phosphate, dipotassium phosphate, sodium borate, potassium borate, sodium tetraborate (borax), potassium tetraborate, sodium o-hydroxybenzoate (sodium salicylate), potassium o-hydroxybenzoate, sodium 5-sulfo-2-hydroxybenzoate (sodium 5-sulfosalicylate), potassium 5-sulfo-2-hydroxybenzoate (potassium 5-sulfosalicylate), etc. An amount of the buffer added to the color developer is preferably not less than 0.1 mol/liter, and particularly from 0.1 to 0.4 mol/liter.

In the present invention, various chelating agents can be jointly used within a range where the effect of the compound of the present invention is not inhibited.

Organic compounds are preferred as the chelating agents, and examples include aminopolycarboxylic acids, organic phosphonic acids, and phosphonocarboxylic acids. Typical examples include nitrilotriacetic acid, diethylenetriaminepentaacetic acid, ethylenediaminetetraacetic acid, N,N,N-trimethylenephosphonic acid, ethylenediamine-N,N,N',N'-tetramethylenephosphonic acid, transcyclohexanediaminetetraacetic acid, 1,2-diaminopropanetetraacetic acid, hydroxyethyliminodiacetic acid, glycol ether diaminetetraacetic acid, ethylenediaminebisorthohydroxyphenyl acetic acid, 2-phosphonobutane-1,2,4-tricarboxylic acid, 1-hydroxyethylidene-1,1-diphosphonic acid, N,N'-bis-(2-hydroxybenzyl)-ethylenediamine-N,N'-diacetic acid, etc. These chelating agents can be jointly used, for example, in an amount of from 0.0001 to 0.05 mol per liter of the processing solution.

In necessary, an optional developing accelerator can be added to the color developer used in the present invention.

Examples of the developing accelerators are thioether compounds as described in JP-B-37-16088, JP-B-3-5987, JP-B-38-7826, JP-B-44-12380, JP-B-45-9019, and U.S. Pat. No. 3,818,247, etc., p-phenylenediamine compounds as described in JP-A-52-49829, JP-A-50-15554, etc., quaternary ammonium salts as described in JP-A-50-137726, JP-B-44-30074, JP-A-56-156826, JP-A-52-43429, amine compounds as described in U.S. Pat. Nos. 2,494,903, 3,128,182, 4,230,796, and 3,253,919, JP-B-41-11431, U.S. Pat. Nos. 2,482,546, 2,496,926, and 3,582,346, etc., polyalkylene oxides as described in JP-B-37-16088, JP-B-42-25201, U.S. Pat. No. 3,128,183, JP-B-41-11431, JP-B-23883, U.S. Pat. No. 3,532,501, etc., as well as imizoles such as 2-methylimidazole and imidazole, etc.

The addition of a 1-phenyl-3-pyrazolidone as a developing aid is preferable for carrying out rapid developing.

If necessary, an optional anti-fogging agent can be added to the color developer used in the present invention. Examples of the anti-fogging agents include alkali metal halides such as sodium chloride, potassium bromide, and potassium iodide, and organic anti-fogging agents. Typical examples of the organic anti-fogging agents include nitrogen-containing heterocyclic compounds, such as benzotriazole, 6-benzimidazole, 5-nitroisoindazole, 5-methylbenzotriazole, 5-nitrobenzotriazole, 5-chlorobenzotriazole, 2-thiazolylbenzoimidazole, 2-thiazolylmethylbenzoimidazole, indazole, hydroxyazaindazole, and adenine.

A brightening agent may be contained in the color developer. As the brightening agents, 4,4'-diamino-2,2'-disulfostilbene compounds are preferable. An amount to be added is from 0 to 5 g/liter, and preferably from 0.1 to 4 g/liter.

Optionally, various surfactants such as alkylsulfonic acids, arylsulfonic acids, aliphatic carboxylic acids, and aromatic carboxylic acids may be added.

In a first black-and-white developer used in a color reversal processing or a black-and-white developer for a black-and-white silver halide photosensitive material which can use the compound of the present invention, various additives which are generally added and are well-known may be contained.

Typical additives which can be mentioned are developing agents such as 1-phenyl-3-pyrazolidone, methol and hydroquinone, preservatives such as sulfites, accelerators comprising alkalis such as sodium hydroxide, sodium carbonate, and potassium carbonate, inorganic or organic suppressants such as potassium bromide, 2-methylbenzimidazole, and methylbenzthiazole, hard water softeners such as polyphosphates, and developing suppressants comprising a trace amount of iodides or mercapto compounds.

The bleaching solution which can be used in the present invention contains at least one oxidizing agent for oxidizing silver and a re-halogenating agent (or an organic ligand used instead). As the bleaching agents, the known iron (III) complexes of polyaminocarboxylic acids, hydrogen peroxide, persulfates, boromates, etc. are used, and they can be jointly used. An amount of the bleaching agent used is from 0.05 to 2 mol, and preferably from 0.1 to 5 mol, per liter of the bleaching solution. Halides such as chlorides, bromides, and iodides are used as re-halogenating agents, as a rule, but instead, organic ligands which form a sparingly soluble silver salt may be used. Amount thereof is from 0.1 to 2 mol/liter, and preferably from 0.3 to 1.5 mol/liter.

The halides described above are added as alkali metal salts, ammonium salts, or salts of guanidine or amines. Typically, sodium bromide, ammonium bromide, potassium chloride, guanidine hydrochloride, etc. can be mentioned, and ammonium bromide is preferred.

The addition of the compound represented by formula (I) enhances the storage ability of the bleaching solution, and this is significant when hydrogen peroxide, a sulfate, or a bromate is used as the bleaching agent.

In addition to the bleaching agent, a bleach-fixing solution to which the compound of the present invention can be added contains a fixer which will be described bellow and may optionally contain the re-halogenating agent. An amount of the bleaching agent contained in the bleach-fixing solution is the same as that in the bleaching solution. An amount of the re-halogenating agent contained in the bleach-fixing solution is from 0 to 2.0 mol/liter, and preferably from 0.01 to 1.0 mol/liter.

The addition of the compound of the present invention in the bleach-fixing solution enhances the storage ability of the solution.

In addition, if necessary, a bleaching accelerator, an anti-corrosive agent for preventing the corrosion of the processing tank, a buffer for maintaining the pH of the solution, a brightening agent, defoaming agent, etc. may optionally be added to the bleaching solution or the bleach-fixing solution of the present invention. The conditions of the bleaching solution, the bleach-fixing solution and the fixing solution preferred for the present invention are the same as those described in the processing solutions which can contain the metal chelate compound of the present invention.

In the fixing solution according to the present invention, the addition of the compound represented by formula (I) enhances the storage stability of the solution as well as masks iron ion carried over from the bleaching solution, making it possible to enhance the stability of the solution.

When the compound of the present invention is added to washing water and a stabilizing solution, similar effects can be obtained.

Washing water or the stabilizing solution used in the water washing stage may contain various surfactant for preventing unevenness caused by water-droplet during the drying of processed photosensitive material. The surfactants which can be mentioned are polyethylene glycol type nonionic surfactants, polyhydric alcohol type nonionic surfactants, alkylbenzenesulfonic acid type anionic surfactants, higher alcohol sulfuric ester salts type anionic surfactants, alkylnaphthalene sulfonate type anionic surfactants, quaternary ammonium salt type cationic surfactants, amine salt type cationic surfactants, amino acid type amphoteric surfactants, and betaine type amphoteric surfactants, but since ionic surfactants sometimes bond to various ions which are mixed accompanying with a processing to form insolubles, the use of a nonionic surfactant is preferable, and an ethylene oxide adduct of alkylphenol is particularly preferable. Octyl-, nonyl-, dodecyl-, dinonylphenols are particularly preferable as the alkylphenols, and the molar number of ethylene oxide added is particularly from 8 to 14 mol. Moreover, also preference is given to the use of a silicon type surfactant having a high defoaming effect.

Into the washing water or the stabilizing solution, various anti-bacterium agents and mildew-proofing agent can be incorporated in order to prevent the generation of fur and mildew generated on a photosensitive material after the processing. Examples of the anti-bacterium agents and mildew-proofing agents are thiazolylbenzimidazole compounds as described in JP-A-57-157244 and JP-A-58-105145, isothiazolone compounds as described in JP-A-54-27424 and JP-A-57-8542, chlorophenol compounds represented by trichlorophenol, bromophenol compounds, organic tin and organic zinc compounds, thiocyanic acid and isothiocyanic acid compounds, acid amide compounds, diazine and triazine compounds, thiourea compounds, benzotriazole alkylguanidine compounds, quaternary ammonium salts represented by benzalkoniumchloride, antibiotics represented by penicillin, general-purpose antibacterial agents as described in J. Antibact. Antifung. Agents, Vol. 1, No. 5, p. 207–223 (1983). They can be used in combination of two or more thereof, and various bactericides described in JP-A-48-83820 may also be used.

It is preferable to jointly use various chelating agents within the range where the effects of the compound of the present invention are not inhibited. Preferred compounds of the chelating agents which can be mentioned are polyaminocarboxylic acid such as ethylenediaminetetraacetic acid and diethylenetriaminepentaacetic acid, organic phosphonic acids such as 1-hydroxyethylidene-1,1-diphosphonic acid and, ethylenediamine-N,N,N',N'-tetramethylenephosphoric acid, and hydrolyzed products of meleic anhydride polymers as described in EP-A-345172, etc.

It is also preferable to incorporate a preservative, which may be incorporated in the above-mentioned fixing solution and the bleach-fixing solution, in washing water.

Examples of the stabilizing solutions include organic acids, solutions having a buffering property at pH of 3 to 6, solutions containing aldehydes (e.g., formalin, glutaraldehyde), hexamethylenetetramine, hexahydrotriazine, N-methylol compounds (e.g., dimethylolurea, N-methylolpyrazole), etc., and in addition, ammonium compounds such as ammonium chloride and ammonium sulfite, metal compounds such as Bi and Al, brightening agents, hardeners, alkanolamines as described in U.S. Pat. No. 4,786,583 can optionally be used.

The water washing stage and stabilizing stage are preferably multi-stage countercurrent manners, and the number of stages are preferably from 2 to 4. The replenishment amount is from 2 to 30 times, and preferably from 2 to 15 times, the carrying over amount from the pre-bath.

In addition to tap water, the water for use in these water washing and the stabilizing stages which can be preferably used is demineralized water having reduce Ca and Mg concentrations of not more than 5 mg/liter by ion exchange resin, water which has been sterilized by halogen, ultraviolet bactericidal lamp, or the like.

Water for adjusting the distilled portion may be tap water, but it is preferable to use demineralized water or sterilized water which is preferably used in the water washing stage or the stabilizing stage.

In each processing solution, the degree of stirring is preferred as strong as possible. As typical process for strengthening the stirring, a process in which a jet is collided with the emulsion surface of the sensitive material as described in JP-A-62-183460, a process for enhancing a rotation effect by using a rotation means as described in JP-A-62-183461, a process in which a turbulence takes place on the emulsion surface by moving the photosensitive material while bringing a wiper blade or squeezing roller provided in the solution in contact with the emulsion surface, thereby enhancing a stirring effect, and a process for increasing the total circulation amount of the processing solution can be mentioned.

An automatic developing machine is preferably used in the processing process of the present invention. As for means for transporting a photosensitive material in the automatic developing machine, they are described in JP-A-60-191257, JP-A-60-191258, and JP-A-60-191259. In order to carry out a rapid processing using the processing composition of the present invention, in an automatic developing machine, it is preferable to shorten the crossover between the processing tanks. An automatic developing machine whose crossover period is not more than 10 seconds is described in JP-A-1-319038.

When a continuous processing is carried out according to the processing process of the present invention using an automatic developing machine, in order to supplement the consumed processing solution accompanying with the processing of a photosensitive material and to suppress undesirable deposition of the components eluted from the processed photosensitive material into the processing solution, a replenishing solution is desirably added according to the amount of the processed photosensitive material. Also, in each stage, two or more processing tanks may be provided, in which case it is preferable to apply a countercurrent manner in which the replenishing solution is pored from the post-tank to the pre-tank. Particularly, in the water washing stage and stabilizing stage, it is preferable to select 2 to 4 stage cascade.

An amount of the replenishing solution is preferably decreased as long as the change in the composition in each processing solution does not cause any disadvantage in terms of photographic characteristics or of staining any other solution.

An amount of the replenishing solution for color developing is from 100 to 1500 ml, and preferably from 100 to 1000 ml, per $m^2$ of the photosensitive material in the case of the material for color photographing, and from 20 to 220 ml, and preferably 30 to 160 ml, per $m^2$ of the photosensitive material in the case of the material for color print.

An amount of the replenishing solution for bleaching is from 10 to 500 ml, and preferably 10 to 160 ml, per $m^2$ of the photosensitive material in the case of the material for color photographing, and from 20 to 300 ml, and preferably from 50 to 150 ml, per $m^2$ of the photosensitive material in the case of the material for color print.

An amount of the replenishing solution for bleach-fixing is from 100 to 3000 ml, and preferably 200 to 1300 ml, per m of the photosensitive material in the case of the material for color photographing, and from 20 to 300 ml, and preferably from 50 to 200 ml, per $m^2$ of the photosensitive material in the case of the material for color print. As for the replenishment of bleach-fixing solution, it can be replenished as one solution, a bleaching composition and a fixing composition may be separately replenished, or it is replenished by mixing an overflow solution from the bleaching bath and/or the fixing bath as the replenishing solution for bleach-fixing.

An amount of the replenishing solution for fixing is from 300 to 3000 ml, and preferably 300 to 1000 ml, per $m^2$ of the photosensitive material in the case of the material for color photograph, and from 20 to 300 ml, and preferably from 50 to 200 ml, per $m^2$ of the photosensitive material in the case of the material for color print.

An amount of replenishment of washing water or the stabilizing solution is from 1 to 30 times, and preferably 2 to 15 times, the amount carried over from the pre-bath, per unit area.

In order to reduce the amounts of the replenishing solution from the viewpoint of environmental safeguard, combinations of various regeneration processes are preferably used. The regeneration may be carried out while circulating the processing solutions in an automatic developing machine or once the processing solutions are removed from the processing baths, and after appropriate regeneration processings are subjected to them, they can be again returned to the processing tanks as the replenishing solutions.

In the present invention, the replenishing amount can be expressed as the sum of the volume of the solid in the case where the substance to be replenished is a solid plus the volume of the diluted water such as water.

The regeneration of the developer can be carried out by ion-exchanging with an anion-exchange resin, removal of the deposited substance through electrodialysis and/or the addition of a chemical, called regenerating agent. The rate of the regeneration is preferably not less than 50%, and more preferably not less than 70%. A commercially available product can be used as the anion-exchange resin, but preference is also given to the use of a highly selective ion exchanger described in JP-A-63-11005.

As the photosensitive materials which can be processed with the processing composition of the present invention, usual black-and-white silver halide photosensitive materials (e.g., black-and-white photosensitive material for photographing, black-and-white photosensitive material for X ray, black-and-white photosensitive material for printing), usual multi-layered color silver halide photosensitive materials (e.g., color negative film, color reversal film, color positive film, cinematic color negative film, color photographic paper, reversal color photographic paper, direct positive color photographic paper), infrared ray-sensitive material for laser scanner, diffusion transfer photosensitive materials (e.g., silver diffusion transfer photosensitive material, color diffusion transfer photosensitive material) can be mentioned. The photosensitive material according to the present invention may have a magnetically recording layer carried thereon.

The photosensitive material used in the present invention, the following material can be preferably used.

A photosensitive material having a magnetically recording layer; the recording layer comprises magnetic grains (preferably Co-covered strongly magnetic iron oxides, etc.) dispersed in a binder, is optically transparent, and is preferably provided on the whole surface of the photosensitive material. The magnetic grains may be processed with a coupling agent as described in JP-A-6-161032. Polymers described in JP-A-4-219569 can be preferably used as the binder. This recording layer may be provided on any portion, but preferably provided on the side opposite to the emulsion layer relative to the support (back layer). A layer containing a lubricant is preferably provided as an upper layer on the recording layer, and the outermost layer on the side of the photosensitive emulsion layer relative to the support preferably contains a matting agent.

In order to impart antistatic property even after the development, the photosensitive material preferably contains an antistatic agent. As the antistatic agent, an electric conductive metal oxide or an ionic polymer is preferred. The antistatic agent is preferably used so that the electric resistance is not more than $10^{12}$ Ω.cm at 25° C. and at 10% relative humidity.

The photosensitive materials having a magnetically recording layer are described in U.S. Pat. Nos. 5,336,589, 5,250,404, 5,229,259, and 5,215,879, and EP-A-466130.

As the support used in the photosensitive material, a polyester support having an improved curl inhibit and being prepared into a thin film is preferable. The thickness is preferably from 50 to 105 μm, and the raw material for the support is preferably made up of an polyethylene aromatic dicarboxylate polyester (preferably comprising benzenedicarboxylic acid, naphthalenedicarboxylic acid and ethylene glycol as main raw materials). The support preferably possesses a glass transition temperature of from 50° to 200° C.. As the surface treatment of the support, an ultraviolet irradiation treatment, a corona discharge treatment, a glow discharge treatment, and a flame treatment are preferable. Before the coating of a subbing layer or after this coating and before the coating of an emulsion layer, preferably the support is thermally treated at a temperature of from 40° C. to the glass transition temperature for 0.1 to 500 hours. In addition to the support, photosensitive material, development processing, cartridge, etc. are described in Kokai-giho, Kogiho No. 94-6023 (published from Japan Patent Association, 1994).

The photosensitive material according to the present invention may have various layer construction (e.g., silver halide emulsion layers each possessing sensitivity to red, green, and blue, subbing layer, anti-halation layer, filter layer, intermediate layer, surface protective layer), and the arrangement thereof, on one or both sides, depending upon the final object of the photosensitive material.

Various couplers can be used in the photosensitive material of the present invention, and typical examples thereof are disclosed in the patent publications described in the above-mentioned *Research Disclosure* No. 17643, VII-C-G and RD No. 307105, VII-C-G, as well as JP-A-62-215272, JP-A-3-33847, JP-A-2-33144, EP-A-447969 and, EP-A-482552, etc.

Examples of the yellow couplers which can be used as long as they do not inhibit the effect of the present invention are those described in U.S. Pat. Nos. 3,933,501, 4,022,620, 4,326,024, 4,401,752, and 4,248,961, JP-B-58-10739, British Patent Nos. 1,425,020, and 1,476,760, U.S. Pat. Nos. 3,973,968, 4,314,023, 4,511,649, and 5,118,599, EP-A-249473, and EP-A-0447969, JP-A-63-23145, JP-A-63-123047, JP-A-1-250944, JP-A-1-213648, etc.

Particularly preferred yellow couplers which can be mentioned are yellow couplers represented by formula (Y) of JP-A-2-139544, page 18, the upper left column to page 22, the lower left column, acylacetamide yellow couplers having a feature in an acyl group as described in JP-A-5-2248 and EP-A-0447969, and yellow couplers represented by formula (Cp-2) as described in JP-A-5-27389 and EP-A-0446863.

The magenta couplers are preferably 5-pyrazolone or pyrazoloazole compounds and those described in U.S. Pat. Nos. 4,310,619, and 4,351,897, European Patent No. 73636, U.S. Pat. Nos. 3,061,432, and 3,725,067, *Research Disclosure No.* 24220 (June, 1984), JP-A-60-33552, *Research Disclosure No.* 24230 (June, 1984), JP-A-60-43659, JP-A-61-72238, JP-A-60-35730, JP-A- 55-118034, JP-A-60-185951, U.S. Pat. Nos. 4,500,630, 4,540,654, and 4,556,630, WO 88/04795, etc. are particularly preferable.

Particularly preferred magenta couplers are pyrazoloazole magenta couplers of formula (I) of JP-A-2-139544, page 3, the lower right column to page 10, the lower right column and 5-pyrazolone magenta couplers of formula (M-1) of JP-A-2-139544, page 17, the lower left column to page 21, the upper left column. The most preferred are the above-mentioned pyrazoloazole magenta couplers.

The cyan couplers are preferably phenol or naphthol couplers, and those described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011, and 4,327,173, West German Patent Application (OLS) No. 3,329,729, EP-A-121365 and EP-A-0249453, U.S. Pat. Nos. 3,446,622, 4,333,999, 4,775,616, 4,451,559, 4,427,767, 4,690,889, 4,254,212, and 4,296,199, JP-A-61-42658, etc. are particularly preferable. Furthermore, pyrazoloazole couplers as described in JP-A-64-553, JP-A-64-554, JP-A-64-555, and, JP-A-64-556, pyrrolotriazole couplers as described in EP-A-0488248 and EP-A-0491197, pyrroloimdazole couplers as described in EP-A-0456226, pyrazolopyrimizine couplers as described in JP-A-64-46753, imidazole couplers as described in U.S. Pat. No. 4,818,672 and JP-A-2-33144, cyclic activated methylene cyan couplers as described in JP-A-64-32260, couplers as described in JP-A-1- 183658, JP-A-2-262655, JP-A-2-85851, and JP-A-3-48243 may be used.

Typical examples of polymerized dye-forming couplers are described in U.S. Pat. Nos. 3,451,820, 4,080,211, 4,367,282, 4,409,320, and 4,576,910, British Patent No. 2,102,137, EP-A-341188, etc.

As couplers whose coloring dye has an appropriate diffusion property, those described in U.S. Pat. No. 4,366,237, British Patent No. 2,125,570, European Patent No. 96570, and West German Patent Application (OLS) No. 3,234,533 are preferable.

Couplers which release a photographically useful residue with coupling are also preferably used in the present invention. As DIR couplers which release a developing suppressant, those which disclosed in patents described in the above-mentioned *Research Disclosure No.* 17643, column VII-F, JP-A-57-151944, JP-A-57-154234, JP-A-60-184248, JP-A-63-37346, JP-A-63-37350, U.S. Pat. Nos. 4,248,962 and 4,782,012 are preferable.

As couplers which imagewise release a nucleating agent or developing accelerator during the development, those described in British Patent Nos. 2,097,140 and 2,131,188, JP-A-59-157638, and JP-A-59-170840 are preferable.

As the couplers which can be used in the color photograph element of the present invention other than the above-mentioned couplers, competitive coupler as described in U.S. Pat. No. 4,130,427, polyvalent couplers as described in U.S. Pat. Nos. 4,283,472, 4,338,393, and 4,310,618, etc., DIR redox compound-releasing couplers, DIR coupler-releasing coupler, DIR coupler-releasing redox compounds, and DIR redox compound-releasing redox compounds as described in JP-A-60-185950, JP-A-62-24252, etc., couplers which release a dye which is again colored after the elimination as described in EP-A-173302, bleaching accelerator-releasing coupler as described in RD No. 11449 and RD No. 24241, JP-A-61-201247, etc., ligand-releasing couplers as described in U.S. Pat. No. 4,555,477, leuco-dye releasing couplers as described in JP-A-63-75747, fluorescent dye releasing couplers as described in U.S. Pat. No. 4,774,181, etc. can be mentioned.

The supports appropriate for use in the present invention are described in the above-mentioned *Research Disclosure* (RD). No. 17643, page 28 and RD No. 18716, page 647, the right column to page 648, the left column.

Particularly, as the supports for use in the color negative film, those having an electrically conductive layer and a transparent magnetic layer on one face as described in JP-A-4-62543, those having a magnetically recording layer as described on FIG. 1A of WO 90/04206, and those having a stripe magnetically recording layer and a transparent magnetically recording layer near the stripe layer as described in JP-A-4-124628 are preferable. A protective layer described in JP-A-4-73737 is preferably provided on these magnetically recording layer.

The support preferably has a thickness of from 70 to 120 μm, and various plastic films described in JP-A-4-124636, page 5, the upper right column line 1 to page 6, the upper left column, line 5 can be used as the raw material of the support. Preferred examples include cellulose derivatives (e.g., diacetyl-, triacetyl-, propionyl-, butanoyl-, acetylpropionylacetate), and polyesters described in JP-B-48-40414 (e.g., polyethylene terephthalate, poly-1,4-cyclohexanedimethylene terephthalate, polyethylene naphthalate). From viewpoint of obtaining a high solution-draining effect, preference is given to the use of polyester.

A cartridge (patrone) which stores the color negative film of the present invention may be any of the presently used or known cartridges, and particularly those having a shape as depicted on FIG. 1 to FIG. 3 of U.S. Pat. No. 4,836,306 and FIG. 1 to FIG. 3 of U.S. Pat. No. 4,846,418 are preferred.

Furthermore, the color negative film which is used in the present invention preferably possesses the contents as described in JP-A-4-12558, page 14, the upper left column, line 1 to page 18, the lower left column, line 11.

The processing compositions of the present invention exhibit the following excellent effects:

(1) The iron complex of the present invention has excellent characteristics that it has an appropriate oxidizing power and a small adverse function, and a small variation in the oxidizing power by varying the pH value and, thus, is suitable for use in medical application, cosmetic preparations, photograph, image-recording materials, copying materials, etc.

(2) When being used as a metal chelate compound, no blockage of the filter takes place, and it excels in desilvering property, bleach fogging, staining with the elapse of time after the processing, and their running stability.

(3) The oxidization or decomposition of the composition of the processing solution due to metal ions is suppressed and, thus, the ability of the processing solution can be maintained over a prolong period of time.

(4) Even due to the deposition of metal ions, no precipitation occurs in the solution and, thus, there is a little trouble such as staining of the film and the blockage of the filter of automatic developing machine.

(5) Even when the temperature of the processing solution is higher than that of the conventional one, since the ability is not deteriorated, the residence time can be extended.

(6) Since the ability is difficult to be influenced by varying the solution conditions such as pH, even when the balance of the replenishment is somewhat changed or a solution is mixed from another bath, the ability of the processing solution can be maintained.

The present invention will now be described in greater detail by reference to Examples, but it should be noted that the present invention is never restricted thereto.

First, the synthesis of the iron complexes of the present invention will be described with reference to typical Synthetic Examples.

EXAMPLE 1

SYNTHESIS OF COMPOUNDS

SYNTHETIC EXAMPLE 1.

SYNTHESIS OF COMPOUND I-11

Into a beaker were incorporated 100 g (0.304 mol) of Compound 35 and 200 ml of water, the mixture was thoroughly stirred, and an aqueous ammonia was added until Compound 35 was completely dissolved (pH: about 5). Separately, 115 g (0.28 mol) of iron nitrate and 200 ml of water were incorporated in a beaker, and iron nitrate was dissolved by stirring. The former aqueous solution (Compound 35) was gradually added to this aqueous iron solution with stirring. After the pH value was adjusted to 5.5 with an aqueous ammonia, the solution was filtered. After the filtrate was concentrated in vacuo until a crystal was separated, the crystal was dissolved by thermally stirring on a hot water bath. After left standing in a refrigerator overnight, the separated crystal was filtered off. The resulting crystal was dissolved in a minimum amount of water while heating on a hot water bath. After the rapid filtration, the filtrate was left standing at room temperature, transferred to a refrigerator after the liquid temperature was cooled down to room temperature, and left standing overnight. The separated crystal was filtered off, washed with cold water and with acetone, and thermally dried (45° C.). Yield: 59 g (49%).

m.p. Gradually decomposed from 200° C.

IR spectrum (KBr) $v_c=0$ 1642 cm$^{-1}$

Elemental Analysis: as $C_{12}H_{20}FeN_3O_8=390.15$

|  | H (%) | C (%) | N (%) |
| --- | --- | --- | --- |
| Calculated | 5.17 | 36.94 | 10.77 |
| Determined | 5.01 | 36.78 | 10.66 |

SYNTHETIC EXAMPLE 2

SYNTHESIS OF COMPOUND I-12

Into a beaker were incorporated 100 g (0.30 mol) of Compound 43 and 200 ml of water, the mixture was thoroughly stirred, and an aqueous ammonia was added until Compound 43 was completely dissolved (pH: about 5). Separately, 109 g (0.27 mol) of iron nitrate and 200 ml of water were incorporated in a beaker, and iron nitrate was dissolved by stirring. The former aqueous solution (Compound 43) was gradually added to this aqueous iron solution with stirring. After the pH value was adjusted to 5.5 with an aqueous ammonia, the solution was filtered. After the filtrate was concentrated in vacuo until a crystal was separated, the crystal was dissolved by thermally stirring on a hot water bath. After left standing in a refrigerator overnight, the separated crystal was filtered off. The resulting crystal was dissolved in a minimum amount of water while heating on a hot water bath. After the rapid filtration, the filtrate was left standing at room temperature, transferred to a refrigerator after the liquid temperature was cooled down to room temperature, and left standing overnight. The separated crystal was filtered off, washed with cold water and with acetone, and thermally dried (45° C.). Yield: 73 g (60%).

m.p. 250° C. or more

IR spectrum (KBr) $v_c=0$ 1640 cm$^{-1}$

Elemental Analysis: as $C_{13}H_{22}FeN_3O_8=404.18$

|  | H (%) | C (%) | N (%) |
|---|---|---|---|
| Calculated | 5.49 | 38.63 | 10.40 |
| Determined | 5.30 | 38.60 | 10.32 |

SYNTHETIC EXAMPLE 3

SYNTHESIS OF COMPOUND I-15

In 25 ml of water were dissolved 18.9 g (0.050 mol) of Compound 42 and 18.4 g (0.046 mol) of iron (III) nitrate nonahydrate, and the pH was adjusted to 3.9 with an aqueous 29% ammonia, followed by filtering. The filtrate was concentrated to approximately 10 ml, left standing in a refrigerator for 2 days, and the separated crystal was filtered off. Washing with cold water and vacuum drying gave 9.2 g (0.020 mol) of Compound I-15 as monohydrate. (Yield: 20%)

Melting point: 230° C. or more (gradually decomposed)
IR spectrum (KBr) $v_c=0$ 1639 cm$^{-1}$
Elemental Analysis: as $C_{16}H_{28}FeO_8 \cdot H_2O$

|  | H (%) | C (%) | N (%) |
|---|---|---|---|
| Calculated | 6.51 | 41.39 | 9.05 |
| Determined | 6.41 | 41.18 | 9.10 |

SYNTHETIC EXAMPLE 4

SYNTHESIS OF COMPOUND I-18

Scheme 11

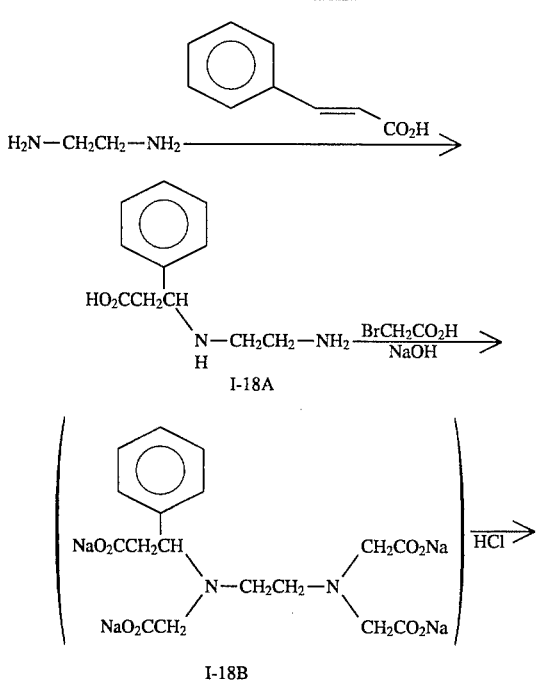

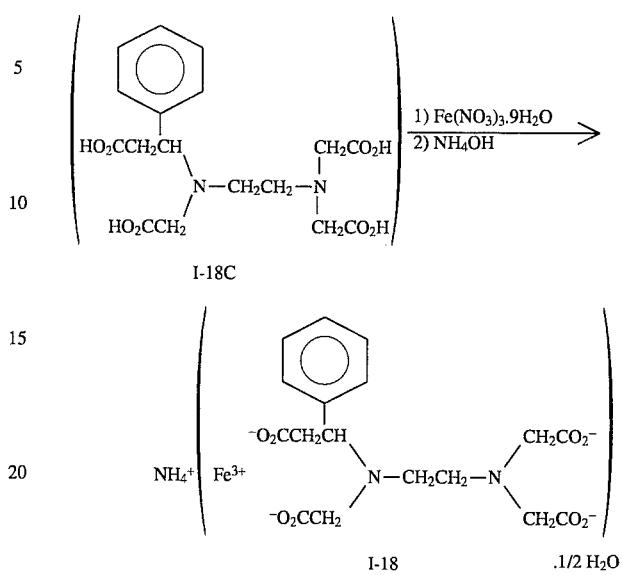

In a three-neck flask were incorporated 100 g (0.679 mol) of cinnamic acid and 811 g (13.5 mol) of ethylenediamine, and the mixture was thermally refluxed for 5 hours. Ethylenediamine was distilled off in vacuo, 200 ml of dichloromethane was added and the mixture was thoroughly stirred. The separated crystal was filtered off, washed with dichloromethane and with methanol, and then thermally dried (45° C.).

In a three-neck flask were incorporated 57 g (0.274 mol) of the resulting intermediate I-18A and 100 ml of water, and 190 g (1.37 mol) of an aqueous bromoacetic acid solution which had been previously neutralized was added. An aqueous 49% sodium hydroxide solution was added, and the reaction liquid was stirred for 12 hours while maintaining the pH at 9–11. An activated carbon was added to the reaction liquid in an amount of 2 g to carry out a Celite filtration, and the pH was adjusted to 1.5 with hydrochloric acid. After the salt was removed by electrodialysis, 100 g (0.248 mol) of iron nitrate was added, and the mixture was thoroughly stirred. The pH was adjusted to 5.5 with an aqueous ammonia, the mixture was filtered, and the filtrate was concentrated in vacuo at 45° C. The filtration of the separated crystal and recrystalization from water gave 40 g (yield: 35%) of Compound I-18.

Melting point: Gradually decomposed from 230° C.
IR spectrum (KBr) $v_c=0$ 1660 cm$^{-1}$
Elemental Analysis: as $C_{17}H_{22}FeN_3O_8 \cdot \frac{1}{2}H_2O=461.23$

|  | H (%) | C (%) | N (%) |
|---|---|---|---|
| Calculated | 5.03 | 44.27 | 9.11 |
| Determined | 4.90 | 44.48 | 9.12 |

SYNTHETIC EXAMPLE 5

SYNTHESIS OF COMPOUND I-2

In 20 ml of water were dissolved 7.80 g (0.022 mol) of Compound 7 and 7.80 g (0.022 mol) of iron (III) nitrate nonahydrate, and the pH was adjusted to 5.2 with an aqueous 29% ammonia, followed by filtering. The filtrate was concentrated to approximately 10 ml, left standing in a refrigerator for 2 days, and the separated crystal was filtered off.

Washing with cold water and vacuum drying gave 3.4 g (0.0078 mol) of Compound I-2 as monohydrate. Yield: 39%.

Melting point: 225° C. or more (gradually decomposed)
IR spectrum (KBr) $v_c=0$ 1625 cm$^{-1}$
Elemental Analysis: as $C_{14}H_{24}N_3FeO_8 \cdot H_2O$

|  | H (%) | C (%) | N (%) |
|---|---|---|---|
| Calculated | 6.01 | 38.55 | 9.63 |
| Determined | 6.23 | 38.74 | 9.64 |

EXAMPLE 2

(DETERMINATION OF OXIDATION-REDUCTION ELECTRIC POTENTIAL)

The oxidation-reduction electric potentials of the iron complexes of the present invention and Comparative compounds were determined with a cyclic voltammetry. The results are shown in Table 1.

TABLE 1

| Sample No. | Iron Complex | pH | Oxidation-reduction electric potential (mV vs SSCE) | Remarks |
|---|---|---|---|---|
| 1 | Comparative a | 5 | −120 | Comparative |
| 2 | Comparative a | 6 | −120 | Comparative |
| 3 | Comparative a | 7 | −150 | Comparative |
| 4 | Comparative a | 8 | −190 | Comparative |
| 5 | Comparative b | 5 | +15 | Comparative |
| 6 | Comparative b | 6 | 0 | Comparative |
| 7 | Comparative b | 7 | −45 | Comparative |
| 8 | Comparative b | 8 | −60 | Comparative |
| 9 | Comparative c | 5 | −145 | Comparative |
| 10 | Comparative c | 6 | −155 | Comparative |
| 11 | Comparative c | 7 | −160 | Comparative |
| 12 | Comparative c | 8 | −180 | Comparative |
| 13 | Compound I-1 | 5 | −170 | Inventive |
| 14 | Compound I-1 | 6 | −170 | Inventive |
| 15 | Compound I-1 | 7 | −170 | Inventive |
| 16 | Compound I-1 | 8 | −175 | Inventive |
| 17 | Compound I-7 | 5 | −115 | Inventive |
| 18 | Compound I-7 | 6 | −115 | Inventive |
| 19 | Compound I-7 | 7 | −115 | Inventive |
| 20 | Compound I-7 | 8 | −120 | Inventive |
| 21 | Compound I-8 | 5 | −20 | Inventive |
| 22 | Compound I-8 | 6 | −20 | Inventive |
| 23 | Compound I-8 | 7 | −20 | Inventive |
| 24 | Compound I-8 | 8 | −25 | Inventive |
| 25 | Compound I-11 | 5 | −120 | Inventive |
| 26 | Compound I-11 | 6 | −120 | Inventive |
| 27 | Compound I-11 | 7 | −125 | Inventive |
| 28 | Compound I-11 | 8 | −135 | Inventive |
| 29 | Compound I-12 | 5 | −120 | Inventive |
| 30 | Compound I-12 | 6 | −120 | Inventive |
| 31 | Compound I-12 | 7 | −124 | Inventive |
| 32 | Compound I-12 | 8 | −130 | Inventive |
| 33 | Compound I-15 | 5 | −160 | Inventive |
| 34 | Compound I-15 | 6 | −160 | Inventive |
| 35 | Compound I-15 | 7 | −160 | Inventive |
| 36 | Compound I-15 | 8 | −165 | Inventive |

Comparative Compound a

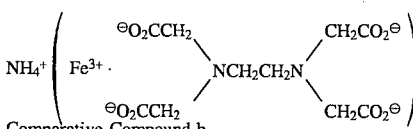

Comparative Compound b

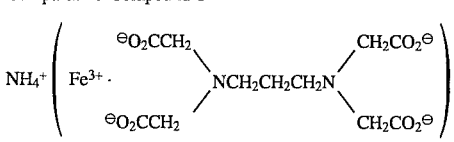

TABLE 1-continued

| Sample No. | Iron Complex | pH | Oxidation-reduction electric potential (mV vs SSCE) | Remarks |
|---|---|---|---|---|

Comparative Compound c $$NH_4^+ \left( Fe^{3+} \cdot \begin{array}{c} ^\ominus O_2CCH_2 \\ \\ ^\ominus O_2CCH_2CH_2 \end{array} NCH_2CH_2N \begin{array}{c} CH_2CO_2^\ominus \\ \\ CH_2CH_2CO_2^\ominus \end{array} \right)$$

*: Supporting electrolyte [NaNO$_3$] = 1.0 M 0.1 M CH$_3$CO$_2$H/CH$_3$CO$_2$NH$_4$ Buffer
Reference electrode: SSCE
Working electrode: Glassy carbon
Control electrode: Platinum electrode
Concentration of iron complex: 10 mM As is clear from Table 1, it could be understood that the compounds of the present invention had appropriate oxidation-reduction electric potential, and a small change due to the difference of pH values in comparison with Comparative compounds, and particularly decrease in the oxidation-reduction electric potential was small at a high pH.

EXAMPLE 3

PRODUCTION OF MULTI-LAYER COLOR PHOTOSENSITIVE MATERIAL

Layers having the following compositions are applied to produce Sample No. 101, which was a multi-layered color photosensitive material.
(Composition of Photosensitive Layer)

The materials used in each layer are classified as follows:

ExC: Cyan coupler,

ExM: Magenta coupler,

ExY: Yellow coupler,

ExS: Sensitizing dye

UV: Ultraviolet absorber

HBS: High boiling point organic solvent

H: Gelatine hardener

The number corresponding to each components shows the coating amount indicated in g/m$^2$ unit, and as for silver halide, the amount converted into silver, provided that the amount of the sensitizing dye applied is shown in molar unit per mol of silver halide applied in the same layer.

| (Sample No. 101) | |
|---|---|
| 1st layer (Anti-halation layer) | |
| Black colloidal silver | silver 0.18 |
| Gelatine | 1.60 |
| ExM-1 | 0.11 |
| ExF-1 | 3.4 × 10$^{-3}$ |
| ExF-2 (Solid dispersing dye) | 0.03 |
| ExF-3 (Solid dispersing dye) | 0.04 |
| HBS-1 | 0.16 |
| 2nd layer (Intermediate layer) | |
| ExC-2 | 0.055 |
| UV-1 | 0.011 |
| UV-2 | 0.030 |
| UV-3 | 0.053 |
| HBS-1 | 0.05 |
| HBS-2 | 0.02 |
| Polyethyl acrylate latex | 8.1 × 10$^{-2}$ |
| Gelatine | 1.75 |

(Sample No. 101)

3rd layer (Low sensitivity red-sensitive emulsion layer)

| | | |
|---|---|---|
| Silver iodobromide emulsion A | silver | 0.46 |
| ExS-1 | | $5.0 \times 10^{-4}$ |
| ExS-2 | | $1.8 \times 10^{-5}$ |
| ExS-3 | | $5.0 \times 10^{-4}$ |
| ExC-1 | | 0.11 |
| ExC-3 | | 0.045 |
| ExC-5 | | 0.0050 |
| ExC-7 | | 0.001 |
| ExC-8 | | 0.010 |
| Cpd-2 | | 0.005 |
| HBS-1 | | 0.090 |
| Gelatine | | 0.87 |

4th layer (Middle sensitivity red-sensitive emulsion layer)

| | | |
|---|---|---|
| Silver iodobromide emulsion D | silver | 0.70 |
| ExS-1 | | $3.0 \times 10^{-4}$ |
| ExS-2 | | $1.2 \times 10^{-5}$ |
| ExS-3 | | $4.0 \times 10^{-4}$ |
| ExC-1 | | 0.22 |
| ExC-2 | | 0.055 |
| ExC-5 | | 0.007 |
| ExC-8 | | 0.009 |
| Cpd-2 | | 0.036 |
| HBS-1 | | 0.11 |
| Gelatine | | 0.70 |

5th layer (High sensitivity red-sensitive emulsion layer)

| | | |
|---|---|---|
| Silver iodobromide emulsion E | silver | 1.62 |
| ExS-1 | | $2.0 \times 10^{-4}$ |
| ExS-2 | | $1.0 \times 10^{-5}$ |
| ExS-3 | | $3.0 \times 10^{-4}$ |
| ExC-1 | | 0.133 |
| ExC-3 | | 0.040 |
| ExC-6 | | 0.040 |
| ExC-8 | | 0.014 |
| Cpd-2 | | 0.050 |
| HBS-1 | | 0.22 |
| HBS-2 | | 0.10 |
| Gelatine | | 0.85 |

6th layer (Intermediate layer)

| | |
|---|---|
| Cpd-1 | 0.07 |
| HBS-1 | 0.04 |
| ExF-4 | 0.03 |
| Polyethyl acrylate latex | 0.19 |
| Gelatine | 2.30 |

7th layer (Low sensitivity green-sensitive emulsion layer)

| | | |
|---|---|---|
| Silver iodobromide emulsion A | silver | 0.24 |
| Silver iodobromide emulsion B | silver | 0.10 |
| Silver iodobromide emulsion C | silver | 0.14 |
| ExS-4 | | $4.0 \times 10^{-5}$ |
| ExS-5 | | $1.8 \times 10^{-4}$ |
| ExS-6 | | $6.5 \times 10^{-4}$ |
| ExM-1 | | 0.005 |
| ExM-2 | | 0.30 |
| ExM-3 | | 0.09 |
| ExY-1 | | 0.015 |
| HBS-1 | | 0.26 |
| HBS-3 | | 0.006 |
| Gelatine | | 0.80 |

8th layer (Middle sensitivity green-sensitive emulsion layer)

| | | |
|---|---|---|
| Silver iodobromide emulsion D | silver | 0.94 |
| ExS-4 | | $2.0 \times 10^{-5}$ |
| ExS-5 | | $1.4 \times 10^{-4}$ |
| ExS-6 | | $5.4 \times 10^{-4}$ |
| ExM-2 | | 0.16 |
| ExM-3 | | 0.045 |
| ExY-1 | | 0.008 |
| ExY-5 | | 0.030 |
| HBS-1 | | 0.14 |
| HBS-3 | | $8.0 \times 10^{-3}$ |
| Gelatine | | 0.90 |

9th layer (High sensitivity green-sensitive emulsion layer)

| | | |
|---|---|---|
| Silver iodobromide emulsion E | silver | 1.29 |
| ExS-4 | | $3.7 \times 10^{-5}$ |
| ExS-5 | | $8.1 \times 10^{-5}$ |
| ExS-6 | | $3.2 \times 10^{-4}$ |
| ExC-4 | | 0.011 |
| ExM-1 | | 0.016 |
| ExM-4 | | 0.046 |
| ExM-5 | | 0.023 |
| Cpd-3 | | 0.050 |
| HBS-1 | | 0.20 |
| HBS-2 | | 0.08 |
| Polyethyl acrylate latex | | 0.26 |
| Gelatine | | 0.82 |

10th layer (Yellow filter layer)

| | | |
|---|---|---|
| Yellow colloidal silver | silver | 0.010 |
| Cpd-1 | | 0.10 |
| ExF-5 (Solid dispersing dye) | | 0.06 |
| ExF-6 (Solid dispersing dye) | | 0.06 |
| ExF-7 (Oil-soluble dye) | | 0.005 |
| HBS-1 | | 0.055 |
| Gelatine | | 0.70 |

11th layer (Low sensitivity blue-sensitive emulsion layer)

| | | |
|---|---|---|
| Silver iodobromide emulsion A | silver | 0.25 |
| Silver iodobromide emulsion C | silver | 0.25 |
| Silver iodobromide emulsion D | silver | 0.10 |
| ExS-7 | | $8.0 \times 10^{-4}$ |
| ExY-1 | | 0.010 |
| ExY-2 | | 0.70 |
| ExY-3 | | 0.055 |
| ExY-4 | | 0.006 |
| ExY-6 | | 0.075 |
| ExC-7 | | 0.040 |
| HBS-1 | | 0.25 |
| Gelatine | | 1.60 |

12th layer (High sensitivity blue-sensitive emulsion layer)

| | | |
|---|---|---|
| Silver iodobromide emulsion F | silver | 1.30 |
| ExS-7 | | $3.0 \times 10^{-4}$ |
| ExY-2 | | 0.15 |
| ExY-3 | | 0.06 |
| HBS-1 | | 0.070 |
| Gelatine | | 1.13 |

13th layer (1st protective layer)

| | |
|---|---|
| UV-2 | 0.08 |
| UV-3 | 0.11 |
| UV-4 | 0.26 |
| HBS-1 | 0.09 |
| Gelatine | 1.20 |

14th layer (2nd protective layer)

| | | |
|---|---|---|
| Silver iodobromide emulsion G | silver | 0.10 |
| H-1 | | 0.30 |
| B-1 (Diameter 1.7 μm) | | $5.0 \times 10^{-2}$ |
| B-2 (Diameter 1.7 μm) | | 0.10 |
| B-3 | | 0.10 |
| S-1 | | 0.20 |
| Gelatine | | 1.75 |

Furthermore, W-1 to W-3, B-4 to B-6, F-1 to F-17, and iron salts, lead salts, gold salts, palladium salts, iridium salts, palladium salts, and rhodium salts were optionally incorporated for enhancing storage property, processing property, resistance to damage by pressure, mildew proofing, antistatic property and applicability.

TABLE 2

| Emulsion | Average AgI content (%) | Average grain size (μm) | Coefficient of variation on grain size (%) | Rate of diameter/thickness ratio of not less than 2 (%) | Construction/Shape |
| --- | --- | --- | --- | --- | --- |
| A | 2.1 | 0.55 | 25 | 81 | Uniform/Tabular form |
| B | 9.1 | 0.63 | 26 | 84 | Triple construction/Tabular form |
| C | 3.1 | 0.60 | 24 | 98 | Triple construction/Tabular form |
| D | 4.2 | 0.80 | 19 | 92 | Triple construction/Tabular form |
| E | 3.2 | 1.10 | 17 | 96 | Triple construction/Tabular form |
| F | 10.8 | 1.75 | 27 | 60 | Double construction/Tabluar form |
| G | 1 | 0.07 | 15 | 0 | Uniform/Cubic form |

In Table 2;

(1) Emulsions A to F were subjected to reduction sensitization with thiourea dioxide and thiosulfinic acid during the preparation of the grains according to Examples of JP-A-2-191938 (corresponding to U.S. Pat. No. 5,061,614).

(2) Emulsion A to F were subjected to a gold-sensitization, a sulfur-sensitization, and a selenium-sensitization in the presence of spectral sensitizing dyes in each photosensitive layer according to Examples of JP-A-3-237450 (corresponding to EP-A-443453).

(3) At the time of preparing the tabular grains, a low molecular weight gelatine was used according to Examples of JP-A-1-158426.

(4) A dislocation line as described in JP-A-3-237450 (corresponding to EP-A-443453) was observed in the tabular grains through a high voltage electron microscope. Preparation of Dispersion of Organic Solid Dispersing Dye The following ExF-2 was dispersed in the following manner: Into a 700 ml volume pot mill were incorporated 21.7 ml of water, 3 ml of an aqueous 5% sodium p-octylphenoxyethoxyethanesulfonate solution, and 0.5 g of an aqueous 5% p-octylphenoxy polyoxyethylene ether (polymerization degree: 10), and then 5.0 g of Dye ExF-2 and 500 ml of zirconium oxide bead (diameter: 1 mm) were added, and the content was dispersed for 2 hours. In this dispersion, BO type vibration ball mill produced by Chuo Koki was used. After the dispersion, the content was taken out, added to 8 g of an aqueous 12.5% gelatine solution, and the bead was filtered off to obtain a gelatine dispersion of the dye. The average grain size of the fine dye grains was 0.44 μm.

Similarly, the solid dispersions of ExF-3, ExF-4 and ExF-6 were obtained. The average grain sizes of the fine dye grains were 0.24 μm, 0.45 μm, and 0.52 μm, respectively. ExF-5 was dispersed according to a microprecipitation dispersing process described in Example 1 of EP-A-549489. The average grain size was 0.06 μm.

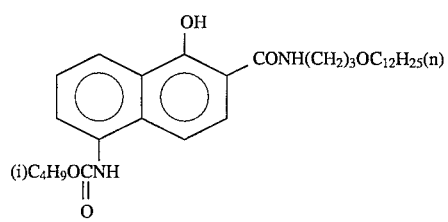

ExC-1

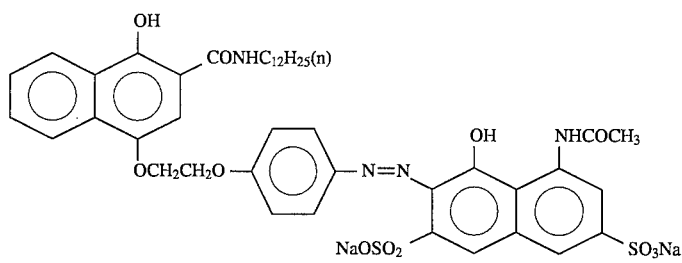

ExC-2

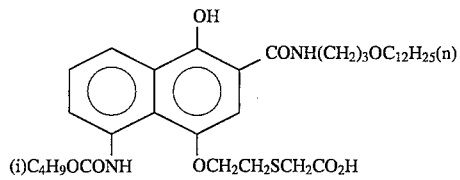

ExC-3

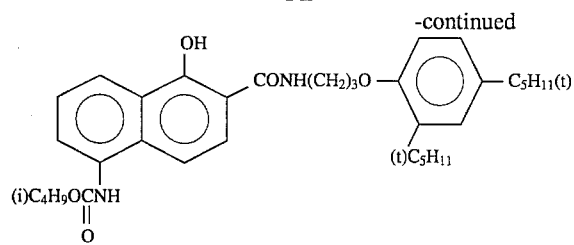
ExC-4
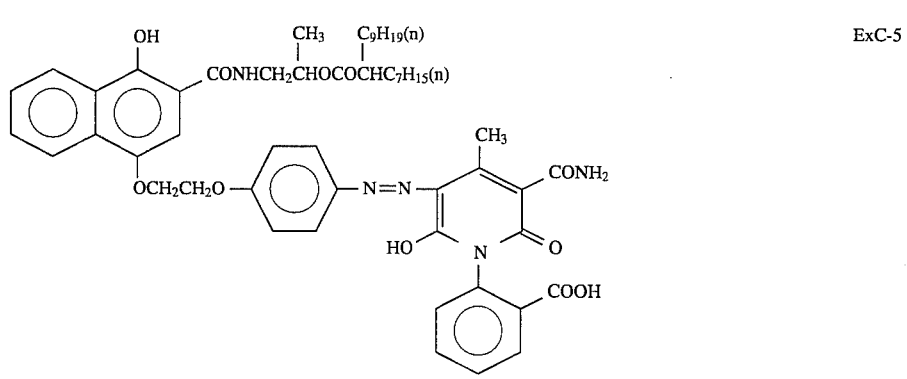
ExC-5
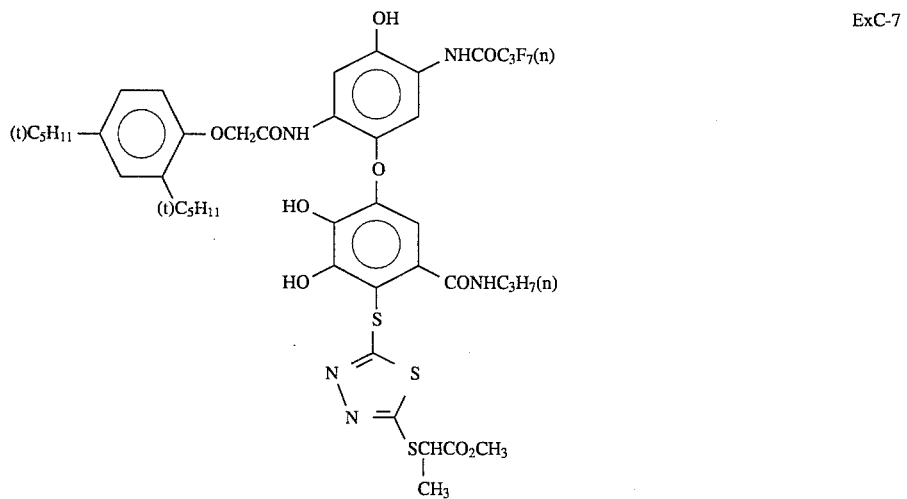
ExC-7
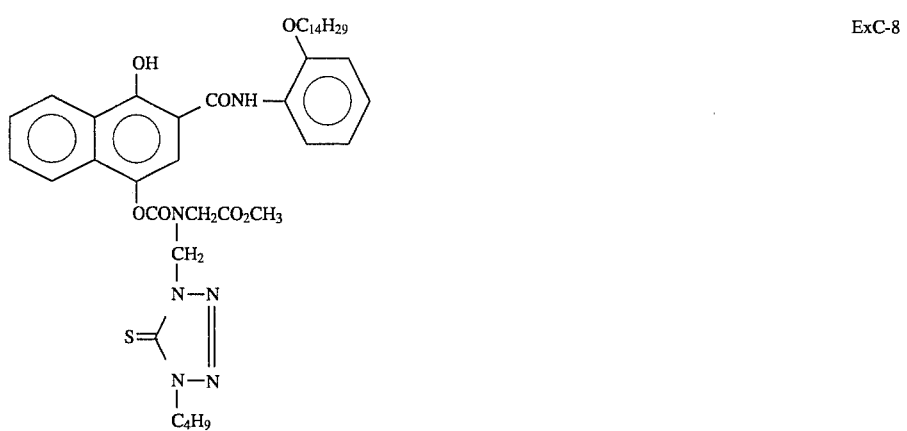
ExC-8

-continued
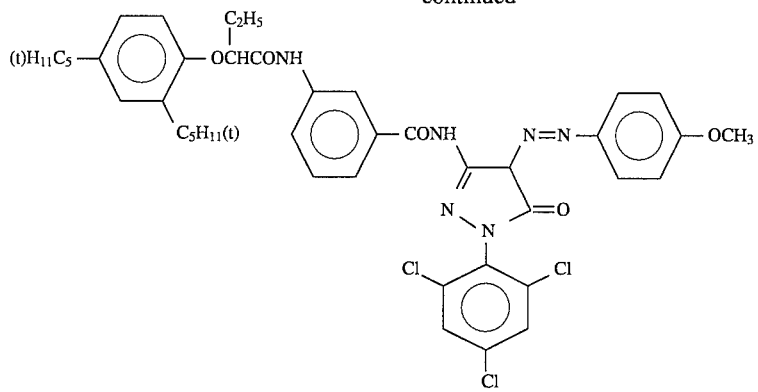
ExM-1
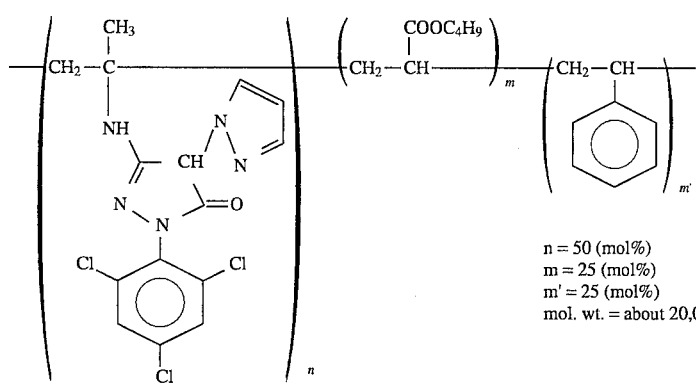
ExM-2
n = 50 (mol%)
m = 25 (mol%)
m' = 25 (mol%)
mol. wt. = about 20,000
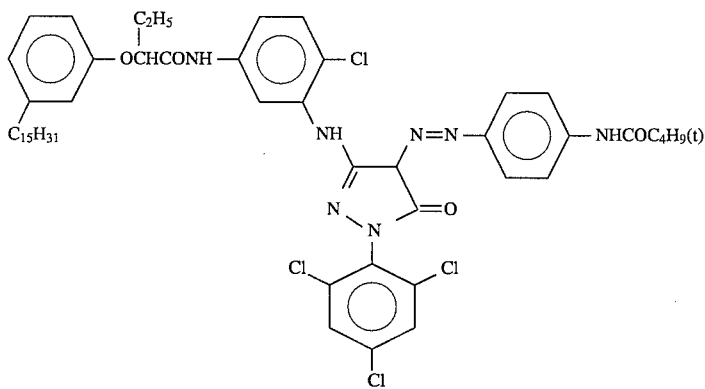
ExM-3
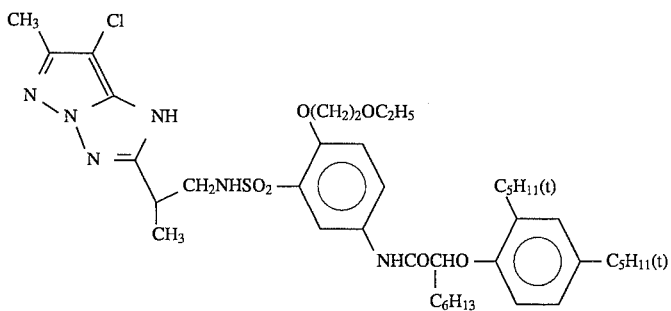
ExM-4

-continued
ExM-5
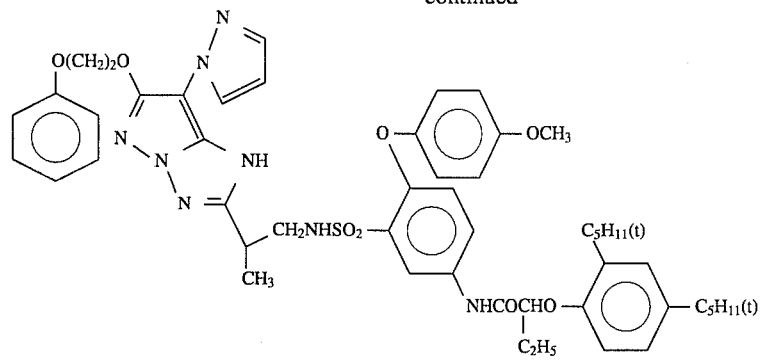
ExY-1
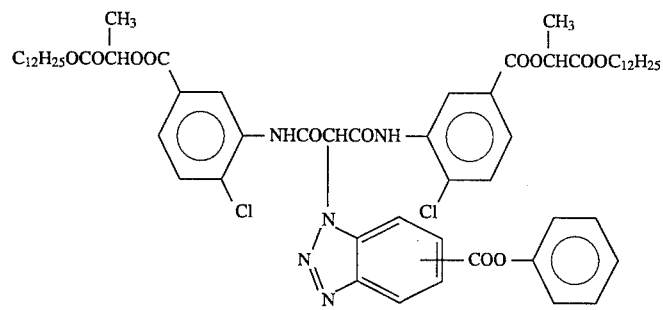
ExY-2
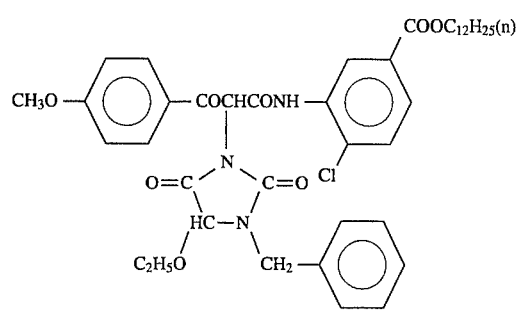
ExY-3
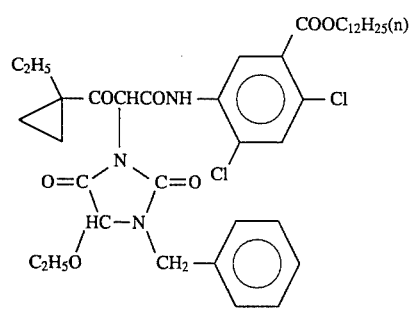
ExY-4
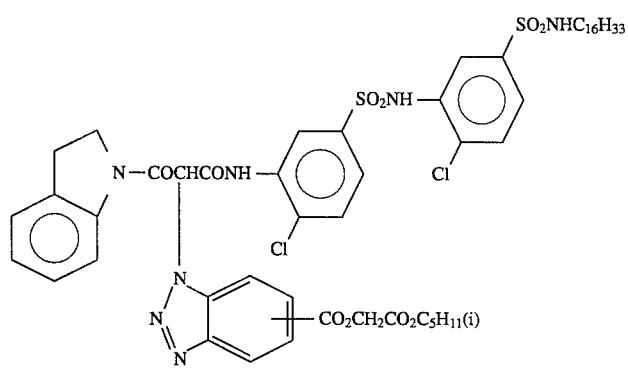

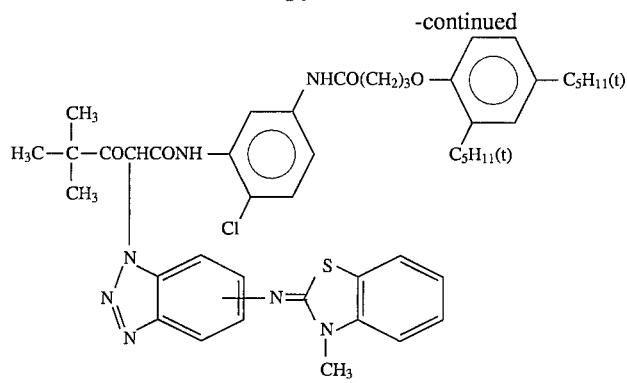
ExY-5
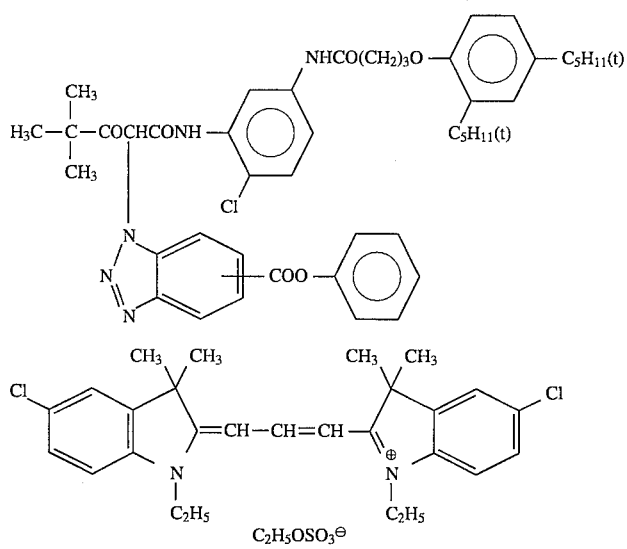
ExY-6
ExF-1
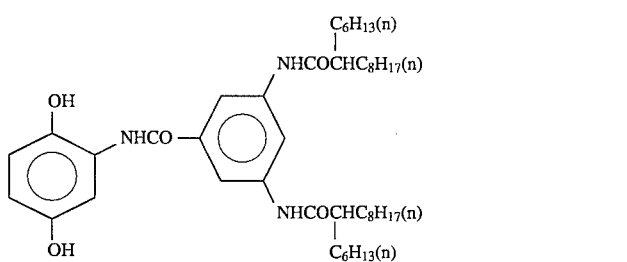
Cpd-1
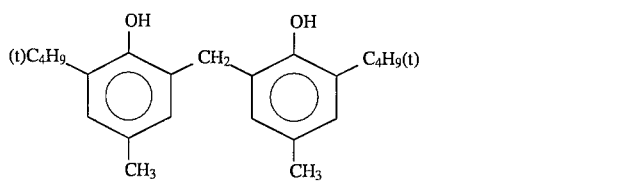
Cpd-2
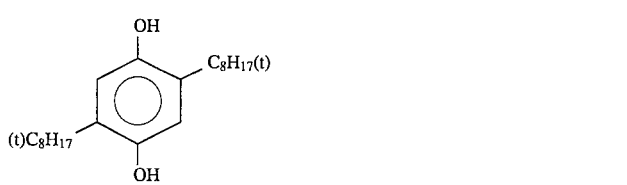
Cpd-3
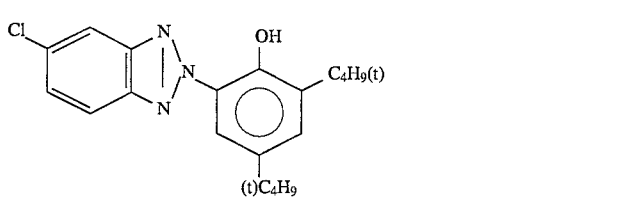
UV-1

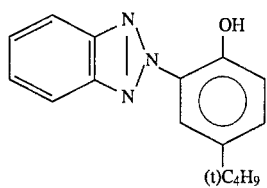 UV-2
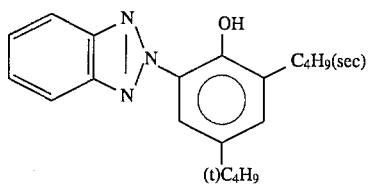 UV-3
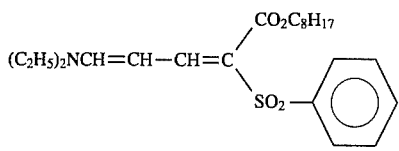 UV-4
Tricresyl phosphate — HBS-1
Di-n-butylphthalate — HBS-2
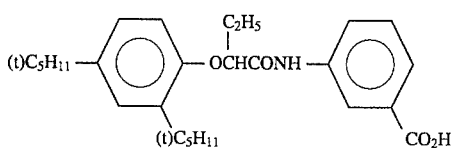 HBS-3
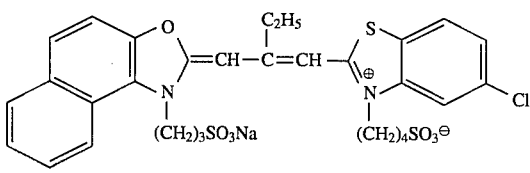 ExS-1
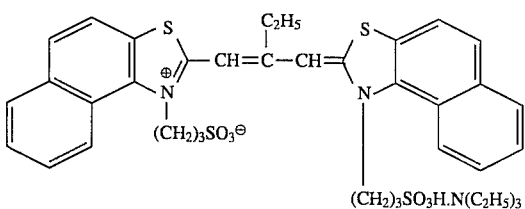 ExS-2
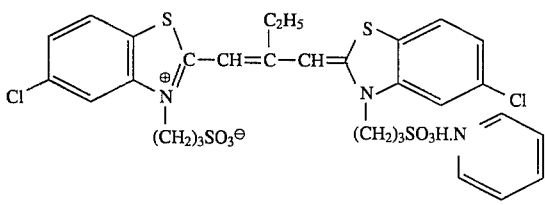 ExS-3
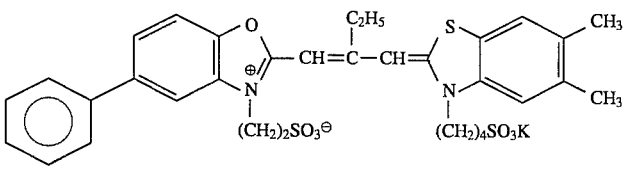 ExS-4

-continued
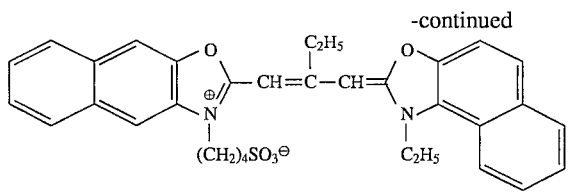 ExS-5
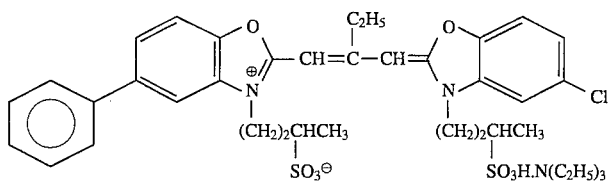 ExS-6
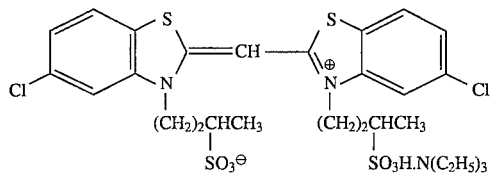 ExS-7
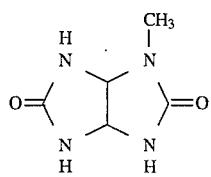 S-1
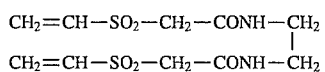 H-1
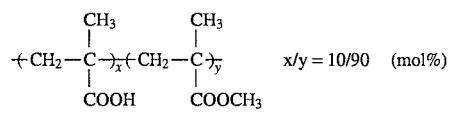 B-1    x/y = 10/90 (mol%)
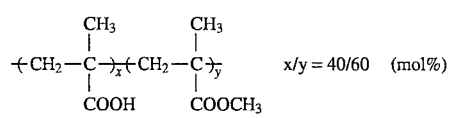 B-2    x/y = 40/60 (mol%)
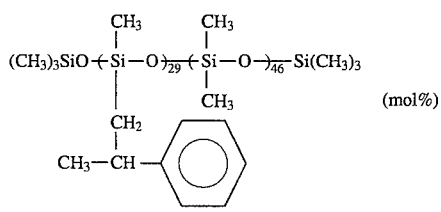 B-3 (mol%)
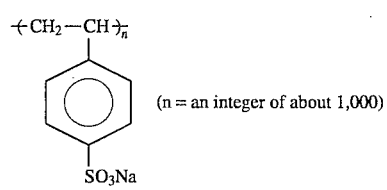 B-4
(n = an integer of about 1,000)
$C_8F_{17}SO_2NHCH_2CH_2CH_2OCH_2CH_2\overset{\oplus}{N}(CH_3)_3$    W-1
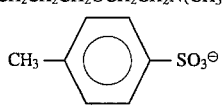 W-2
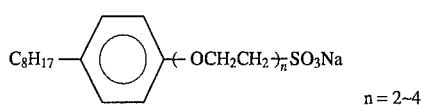
n = 2~4

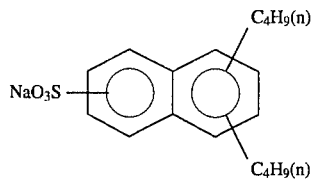 W-3
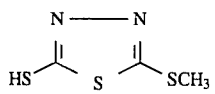 F-1
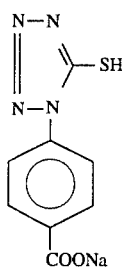 F-2
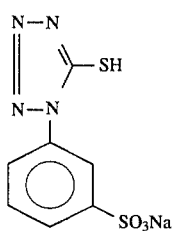 F-3
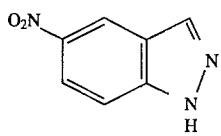 F-4
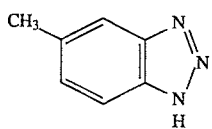 F-5
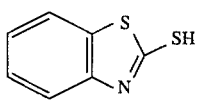 F-6
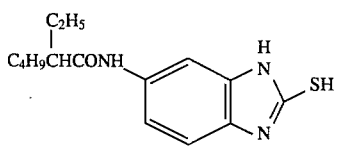 F-7
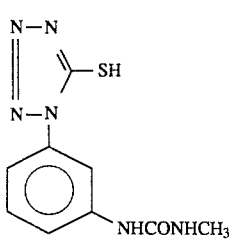 F-8
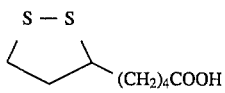 F-9

-continued
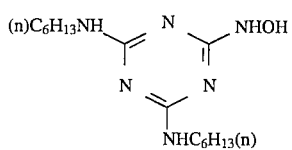
F-10
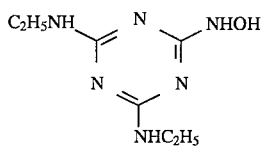
F-11
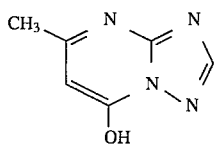
F-12
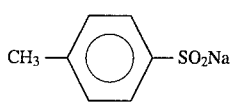
F-13
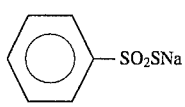
F-14
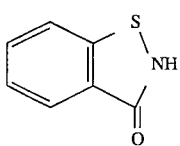
F-15
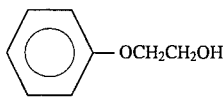
F-16
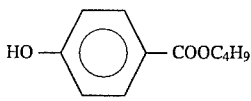
F-17
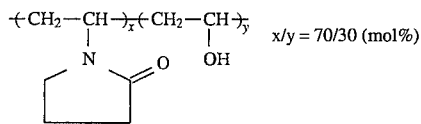 x/y = 70/30 (mol%)
B-5
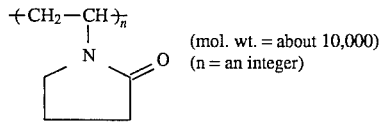 (mol. wt. = about 10,000) (n = an integer)
B-6
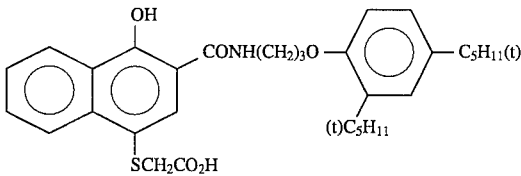
ExC-6
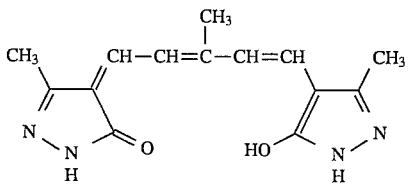
ExF-3

-continued

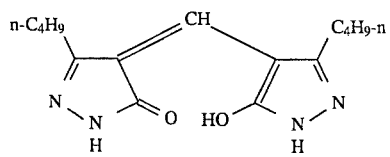

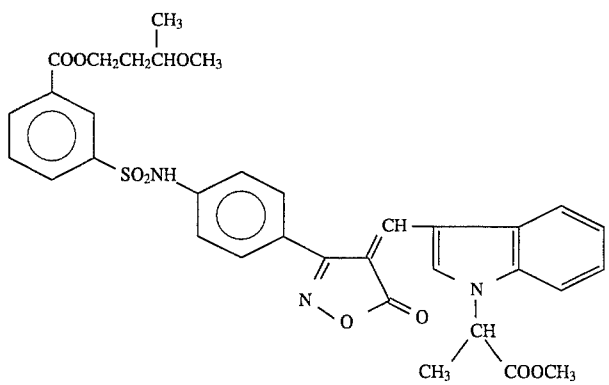

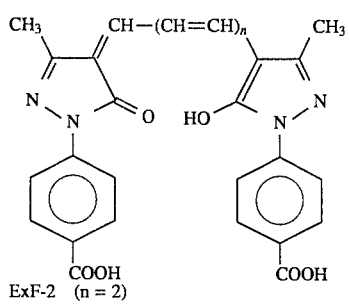

ExF-2 (n = 2)

ExF-4 (n = 1)

ExF-5 (n = 0)

ExF-6

ExF-7

Sample No. 101 prepared as described above and cut into 35 mm width was subjected to an imagewise exposure, and continuously processed with the following processing solutions until the replenishment amount of bleach-fixing solution was 10 times the value of the tank.

In the bleach-fixing solution, silver was removed inline using a silver-recovering apparatus, part of the overflow from the silver-recovering apparatus was discharged as a wasted liquid, and the remaining was regenerated to be reused as a replenishing solution for the bleach-fixing solution. The silver-recovering apparatus used was a small-size electrolytic silver-recovering apparatus having an anode composed of carbon and a cathode composed of stainless steel and was operated at a current density of 0.5 A/dm$^2$. The schematic view of the silver-recovering system is depicted on FIG. 1 of JP-A-6-175305. To be specific, overflow 21 of bleach-fixing tank 20 was directly connected to silver-recovering apparatus 22, part of overflow was returned to the original bleach-fixing tank 20 at 100 ml/minute through filter 24 by means of pump 23. Overflow 25 from the silver-recovering apparatus 22 was recovered in regenerating tank 26 in an amount of 300 ml per liter of the overflow, and when the recovered amount was 1 liter, air was blown for about 2 hours, after which regenerating agent 28 was added which was transferred to replenishing tank 30 for bleach-fixing solution by means of pump 29. The remaining solution (100 ml) was discharged as a wasted liquid. An amount of the wasted liquid was 220 ml per m$^2$ of Sample No. 101.

In the water washing, a 5-stage multi-room washing tank was used in a horizontal arrangement, and countercurrent cascade was carried out. Typically, one described in FIG. 1 of JP-A-66540 was used.

The overflow solution of the first washing water $W_1$ was cascaded to the bleach-fixing tank, which was the pre-bath. A reverse osmosis (RO) apparatus, RC 30, (produced by Fuji Photo Film Co., Ltd.) was provided between the fourth washing water $W_4$ and the fifth washing water $W_5$. That is, the washing water taken from $W_4$ was applied to the RO apparatus, the concentrate was returned to $W_4$, and the transmitted solution was returned to $W_4$. The outline of the processing apparatus is depicted on FIG. 2 of JP-A-6-175305. The processing stages was as follows:

| | Processing Stage | | | |
|---|---|---|---|---|
| | Processing Period | Processing Temp. | Replenishing amount | Tank volume (l) |
| Color developing | 1'50" | 45° C. | 104 ml | 2 |
| Bleach-fixation | 1'50" | 45° C. | 200 ml | 2 |
| Water washing (1) | 15" | 45° C. | — | 0.5 |
| Water washing (2) | 15" | 45° C. | — | 0.5 |
| Water washing (3) | 15" | 45° C. | — | 0.5 |

| | Processing Stage | | | |
|---|---|---|---|---|
| | Processing Period | Processing Temp. | Replenishing amount | Tank volume (l) |
| Water washing (4) | 15" | 45° C. | — | 0.5 |
| Water washing (5) | 15" | 45° C. | 104 ml | 0.5 |
| Stabilization | 2" | Room Temp. | 30 ml | Coating |
| Drying | 50" | 70° C. | — | — |

*[1]: The replenishing amount was an amount per 1 m² of the photosensitive material.

The crossover period from the color developing to the bleach-fixation and from bleach-fixation to water washing (1) was 3 minutes. The crossover period was included in the processing period in the pre-bath. An average carrying over amount per m² of the photosensitive material was 65 ml.

In each tank, for the adjustment of distillation, the temperature and humidity out of the processing machine were detected by a thermo/humidity meter as described in JP-A-3-280042 to calculate the amount of the distillation which was adjusted. The ion-exchanged water for the above washing water was used for the adjustment of distillation.

The compositions of the processing solutions were as follows:

| (Color (Developer)) | Mother Solution (g) | Replenishing Solution (g) |
|---|---|---|
| Diethyltriaminepentaacetic acid | 1.2 | 4.0 |
| 1-Hydroxyethylidene-1,1-disulfonic acid | 2.7 | 3.3 |
| Caustic potassium | 2.50 | 3.90 |
| Sodium sulfite | 3.84 | 9.0 |
| Sodium bicarbonate | 1.8 | — |
| Potassium carbonate | 31.7 | 39.0 |
| Potassium bromide | 5.60 | — |
| Potassium iodide | 1.3 mg | — |
| Hydroxyamine sulfate | 2.5 | 6.9 |
| 2-Methyl-4-[N-ethyl-N-(β-hydroxyethyl)amino]aniline sulfate | 9.0 | 18.5 |
| Water to make | 1.0 l | 1.0 l |
| pH | 10.05 | 11.90 |

| (Bleach-fixing Solution) | Mother Solution (mol) | Replenishing Solution at starting (mol) |
|---|---|---|
| Ammonium thiosulfate | 1.4 | 2.31 |
| Chelating agent described in Table 3 | 0.17 | 0.28 |
| Ferric nitrate nonahydorate | 0.15 | 0.25 |
| Ammonium bisulfite | 0.10 | 0.17 |
| Metacarboxybenzene sulfinic acid | 0.05 | 0.09 |
| Water to make | 1.0 l | 1.0 l |
| pH (25° C.) | 6.0 | 6.0 |

(Adjusted with acetic acid and ammonium water)

| Regenerating Agent for Bleach-fixing Agent) | Amount per liter of the recovering solution for regeneration (g) |
|---|---|
| Ammonium thiosulfate | 0.91 |
| Chelating agent described in Table 3 | 0.11 |
| Ferric nitrate nonahydrate | 0.10 |
| Ammonium sulfite | 0.07 |
| Methacarboxybenzene-sulfinic acid | 0.04 |

| (Washing Water) | Common to the mother solution and tank solution. |
|---|---|

Tap water was passed through a mixed bed type column filled with an H type strongly acidic cation exchange resin (Amberite IR-120B, produced by Rohm & Haas) and an OH type strongly basic anion exchange resin (Amberite IRA-400, produced by Rohm & Haas) to reduce calcium and magnesium ion concentration to be not more than 3 mg/l, and then 20 mg/l of sodium dichloroisocyanurate and 150 mg/l of sodium sulfate were added. The pH of this solution was from 6.5 to 7.5.

| (Stabilizing Solution) for Coating | (unit: g) |
|---|---|
| Formalin (37%) | 2.0 ml |
| Polyoxyethylene-p-monononylphenyl ether (average polymerization degree: 10) | 0.3 |
| Disodium ethylenediaminetetraacetate | 0.05 |
| Water to make | 1.0 l |
| pH | 5.0–8.0 |

When the above processing system was carried out, the amount of wasted liquid after 100 m² of Sample No. 101 was processed was 22 l.

The amount of the remaining silver on the highest density portion for Sample No. 101 of the multi-layered color photosensitive material having been processed in the above manner was determined by a fluorescent X ray analysis. The results are shown in Table 3. Furthermore, as for Samples obtained after the processing, $D_{min}$ value determined with a green light (G-light) was read.

Subsequently, as a standard processing process without bleach fogging, the processing was carried out changing the bleach-fixing stage to the four stages of bleaching/water washing (A)/water washing (B)/fixing. In the processing, no alternation was made, except for the following:

| Processing stage | Processing Period | Processing Temp. | Replenishing amount |
|---|---|---|---|
| Beaching | 3'00" | 38° C. | 710 ml |
| Water washing (A) | 15" | 24° C. | Countercurrent piping from (B) to (A) |
| Water washing (B) | 15" | 24° C. | 430 ml |
| Fixing | 3'00" | 38° C. | 430 ml |

| | Tank Solution (g) | Replenishing Solution (g) |
|---|---|---|
| (Standard Bleaching Solution) | | |
| Sodium ethylenediaminetetra-acetato ferrate trihydrate | 100.0 | 120.0 |
| Disodium ethylenediamine-tetraacetate | 10.0 | 11.0 |
| 3-Mercapto-1,2,4-triazole | 0.03 | 0.08 |
| Ammonium bromide | 140.0 | 160.0 |
| Ammonium nitrate | 30.0 | 35.0 |
| An aqueous ammonia (27%) | 6.5 ml | 4.0 ml |
| Water to make | 1.0 l | 1.0 l |
| pH (adjusted with an aqueous ammonia and nitric acid) | 6.0 | 5.7 |
| (Fixing Solution) | | |
| Disodium ethylenediamine-tetraacetate | 0.5 | 0.7 |
| Ammonium sulfite | 20.0 | 22.0 |

-continued

| | Tank Solution (g) | Replenishing Solution (g) |
|---|---|---|
| An aqueous ammonium solution (700 g/l) | 295.0ml | 320.0ml |
| Acetic acid (90%) | 3.3 | 4.0 |
| Water to make | 1.0 l | 1.0 l |
| pH (adjusted with an aqueous ammonia and acetic acid) | 6.7 | 6.8 |

As for the processed photosensitive material obtained by using the standard bleaching solution, a $D_{min}$ value was similarly read. These resulting $D_{min}$ values were used to obtain differences between $D_{min}$ of the photosensitive materials, $\Delta D_{min}$, taking the $D_{min}$ value obtained by the standard bleaching solution as a standard. The $D_{min}$ value obtained by the standard bleaching solution was 0.60. Bleach fogging $(\Delta D_{min})=(D_{min}$ of each sample$)-(D_{min}$ obtained by the standard bleaching solution)

Subsequently, the above-mentioned Sample No. 101 was stored under the following conditions and an increase in the staining during the storage of the processed photosensitive material was determined from the change in the density of $D_{min}$ of the uncolored portion before and after the storage. Dark, humidity, thermal conditions: 60° C., 70% RH, 4 weeks Increase in staining $(\Delta D)=(D_{min}$ after storage$)-(D_{min}$ before storage)

Furthermore, the generation of staining on the back surface of the photosensitive material and the states of the filer blockage were observed by the following methods. Staining: The surface of Sample No. 101 where no emulsion had been applied after completion of running was observed, and the presence or absence of the staining was observed:
Evaluation:
A: No generation of staining
B. Slight generation of staining, but not problem in practical use
C: Generation of Staining
Blockage of filter:
The filter portion was taken out after completion of running, the states of inner blockage were observed.
Evaluation:
A: Almost no blockage
B: Partly blockage
C: Blockage on almost all portions, but the solution could be passed.
D: Perfect blockage, stage where the solution was very difficult to be passed.
The results are shown in Table 3.

TABLE 3

| No. | Chelating agent | Residual silver μg/cm² | Bleach fogging ΔDmin (G) | Increase in staining ΔD (G) | Staining | Filter blockage | Remarks |
|---|---|---|---|---|---|---|---|
| 101 | Comparative A | 48.5 | 0.00 | 0.01 | A | A | Comparative |
| 102 | Comparative B | 39.7 | 0.08 | 0.08 | C | D | Comparative |
| 103 | comparative C | 35.0 | 0.07 | 0.06 | C | C | Comparative |
| 104 | Comparative D | 12.0 | 0.00 | 0.01 | B | C | Comparative |
| 105 | Compound 1 | 6.2 | 0.00 | 0.01 | A | A | Comparative |
| 106 | Compound 6 | 5.9 | 0.00 | 0.01 | A | A | Inventive |
| 107 | Compound 7 | 5.6 | 0.00 | 0.01 | A | A | Inventive |
| 108 | Compound 8 | 4.8 | 0.00 | 0.01 | A | A | Inventive |
| 109 | Compound 9 | 4.6 | 0.00 | 0.01 | A | B | Inventive |
| 110 | Compound 10 | 3.8 | 0.00 | 0.02 | A | A | Inventive |
| 111 | Compound 12 | 4.0 | 0.01 | 0.02 | A | A | Inventive |
| 112 | Compound 16 | 4.2 | 0.01 | 0.02 | A | A | Inventive |
| 113 | Compound 17 | 4.5 | 0.01 | 0.02 | A | A | Inventive |
| 114 | Compound 19 | 3.4 | 0.02 | 0.02 | B | B | Inventive |
| 115 | Compound 20 | 3.0 | 0.02 | 0.02 | B | B | Inventive |
| 116 | Compound 34 | 5.0 | 0.01 | 0.01 | A | A | Inventive |
| 117 | Compound 35 | 4.2 | 0.00 | 0.01 | A | A | Inventive |
| 118 | Compound 36 | 4.8 | 0.00 | 0.01 | A | A | Inventive |
| 119 | Compound 42 | 3.0 | 0.01 | 0.01 | A | A | Inventive |
| 120 | Compound 43 | 3.1 | 0.01 | 0.01 | A | A | Inventive |
| 121 | Compound 44 | 3.5 | 0.01 | 0.01 | A | A | Inventive |

Comparative Compound A

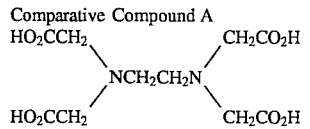

Comparative Compound B

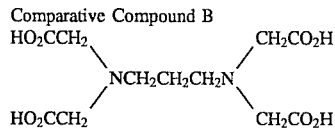

Comparative Compound C

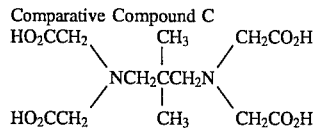

Compound described in JP-A-3-192254

TABLE 3-continued

| No. | Chelating agent | Residual silver μg/cm² | Bleach fogging ΔDmin (G) | Increase in staining ΔD (G) | Staining | Filter blockage | Remarks |
|-----|----------------|------------------------|--------------------------|------------------------------|----------|-----------------|---------|

Comparative Compound D $$\text{HO}_2\text{C}-\underset{\underset{\text{CH}_3}{|}}{\text{CH}} \diagdown \overset{}{} \diagup \text{CH}_2\text{PO}_3\text{H}_2$$
$$\phantom{XXXXX}\text{NCH}_2\text{CH}_2\text{N}$$
$$\text{HO}_2\text{CCH} \diagup \phantom{X} \diagdown \text{CH}_2\text{PO}_3\text{H}_2$$
$$\underset{\text{CH}_3}{|}$$

Compound described in JP-A-3-216650

As shown in Table 3, the significance of the present invention which totally satisfies desilvering property, bleach fogging, increase in staining, generation of staining, and blockage of filter is clarified.

EXAMPLE 4

The multi-layered color photographic paper described in Example 4 of JP-A-5-303186 (Sample No. 001) and the following processing solutions were prepared.

|  | Mother Solution | Replenishing Solution |
|---|---|---|
| (Color Developer) | | |
| Water | 700 ml | 700 ml |
| Diethylenetriaminepentaacetic acid | 0.4 g | 0.4 g |
| N,N,N-tris(methylene-sulfonic acid) | 4.0 g | 4.0 g |
| Disodium 1,2-dihydroxy-benzene-4,6-disulfonate | 0.5 g | 0.5 g |
| Triethanolamine | 12.0 g | 12.0 g |
| Potassium chloride | 6.5 g | — |
| Potassium bromide | 0.03 g | — |
| Potassium carbonate | 27.0 g | 27.0 g |
| Diaminosutilbene brightening agent (WHITEX 4, produced by Sumitomo Chemicals) | 1.0 g | 3.0 g |
| Sodium sulfite | 0.1 g | 0.1 g |
| N,N-bis(sulfoethyl)hydroxylamine | 10.0 g | 13.0 g |
| N-ethyl-N-(β-methanesulfonamide ethyl)-3-methyl-4-aminoaniline sulfate | 5.0 g | 11.5 g |
| Water to make | 1000 ml | 1000 ml |
| pH (25° C.) | 10.10 | 11.10 |
| (Bleach-fixing Solution) | | |
| Water | 600 ml | 600 ml |
| Ammonium thiosulfate (700 g/l) | 100 ml | 250 ml |
| Ammonium sulfite | 40 g | 100 g |
| Chelating agent described in Table 4 | 0.166 ml | 0.407 mol |
| Ferric nitrate nonahydorate | 0.138 mol | 0.339 mol |
| Ethylenediaminetetraacetic acid | 5 g | 12.5 g |
| Ammonium bromide | 40 g | 75 g |
| Nitric acid (67%) | 30 g | 65 g |
| Water to make | 1000 ml | 1000 ml |
| pH (25° C.) (adjusted with acetic acid and an aqueous ammonia) | 5.8 | 5.6 |
| (Rinsing Solutions) | Common to the mother solution and replenishing solution. | |

Tap water was passed through a mixed bed type column filled with an H type strongly acidic cation exchange resin (Amberite IR-120B, produced by Rohm & Haas) and an OH type strongly basic anion exchange resin (Amberite IRA-400, produced by Rohm & Haas) to reduce calcium and magnesium ion concentration to be not more than 3 mg/l, and then 20 mg/l of sodium dichloroisocyanurate and 150 mg/l of sodium sulfate were added. The pH of this solution was from 6.5 to 7.5.

In order to determine the amount of remaining silver, the multi-layered color photographic paper (Sample No. 001) was uniformly exposed so that the gray density was 2.2, and processed by the following processing stages. The amount of the remaining silver was determined by a fluorescent X ray analysis. In order to determine an increase in staining after the processing, the sample was applied to gradation-exposure through a wedge, and similarly processed. The sample after processing was left standing at 80° C. and at 70% relative humidity for 1 week, and an increase in staining after the elapse of time was determined. In the processing, the above-mentioned processing solutions were used, and the processing was carried out via the following processing stage, and at beginning each tank solution was incorporated in each processing tank, and the replenishing solutions were added according to the amount of processing to continue the processing. The processing was carried out until the accumulative replenishing amount was three times the volume of the tank, and the results of the processing at this time are shown in Table 4.

| Processing Stage | Temp. | Period | Replenishing amount | Tank volume |
|---|---|---|---|---|
| Color developing | 39° C. | 45" | 70 ml | 20 l |
| Bleach-fixation | 35° C. | (1) 45" (2) 20" | 60 ml**[2] | 20 l |
| Rinsing (1) | 35° C. | 20" | — | 10 l |
| Rinsing (2) | 35° C. | 20" | — | 10 l |
| Rinsing (3) | 35° C. | 20" | 360 ml | 10 l |
| Drying | 80° C. | 60" | | |

*[1]: The replenishing amount was an amount per 1 m² of the photosentive material.
Three tank countercurrent manner from rinse (3) to (1)
**[2]: In addition to 60 ml of the bleach-fixing solution, the solution from rinse 91) was poured in an amount of 120 ml per 1 m² of the photosensitive material

TABLE 4

| No. | Chelating agent | Bleach-fixing period (sec.) | Residual silver μg/cm² | Increase in staining ΔD (G) | Remarks |
|---|---|---|---|---|---|
| 201 | Comparative A | 45 | 2.6 | 0.11 | Comparative |
|  |  | 20 | 8.0 | 0.20 | " |
| 202 | Comparative B | 45 | 10.6 | 0.03 | " |
|  |  | 20 | 20.2 | 0.04 | " |
| 203 | Comparative C | 45 | 9.8 | 0.08 | " |
|  |  | 20 | 18.6 | 0.09 | " |
| 204 | Compound 6 | 45 | 1.0 | 0.03 | Invention |
|  |  | 20 | 3.8 | 0.04 | " |
| 205 | Compound 7 | 45 | 0.9 | 0.02 | " |
|  |  | 20 | 2.8 | 0.03 | " |
| 206 | Compound 10 | 45 | 0.7 | 0.02 | " |
|  |  | 20 | 1.5 | 0.03 | " |
| 207 | Compound 12 | 45 | 1.2 | 0.03 | " |
|  |  | 20 | 4.2 | 0.04 | " |
| 208 | Compound 19 | 45 | 1.0 | 0.02 | " |
|  |  | 20 | 3.8 | 0.03 | " |
| 209 | Compound 20 | 45 | 0.9 | 0.02 | " |
|  |  | 20 | 3.2 | 0.03 | " |
| 210 | Compound 21 | 45 | 0.9 | 0.03 | " |
|  |  | 20 | 3.0 | 0.04 | " |
| 211 | Compound 42 | 45 | 0.7 | 0.02 | " |
|  |  | 20 | 2.2 | 0.03 | " |

Comparative compounds A, B, C were the same as those of Example 3.

As shown in Table 4, the metal chelate compounds of the present invention had desilvering property and staining after the processing with the elapse of time superior to those of Comparative compounds. Particularly, in the processing where the period of bleach-fixing was shortened, these effect were remarkable. To be specific, even when the bleach-fixing period was half, the amounts of the remaining silver before and after the running were small, and staining with the elapse of time was also excellent. In the Comparative compounds, although there was almost no remaining silver when processed immediately after the preparation of the solution, the drastically decrease in desilvering property as described above and the formation of precipitate took place with the progress of running.

EXAMPLE 5

Sample No. 301 was prepared as in Example 1 of JP-A-5-165176, except for using a 100 μm thick polyethylene terephthalate as a support instead of the triacetate cellulose film support with a subbing layer used in multi-layered color photosensitive material produced in Examples 1 of JP-A-5-165176, and applying the stripe magnetically recording layer described in Example 1 of JP-A-4-124628 to the back surface. When Sample No. 301 was used to carry out the tests similar to those of Sample Nos. 101 and 106 of Example 3 of the present invention, the effects of the present invention similar to Example 3 were obtained.

Sample No. 302 was prepared as in Example 3 of the present invention, except for using the same support and the back same layer as those of Sample No. I-3 of Example 1 of JP-A-4-62543 instead of the support used in the multi-layered color photosensitive material No. 101 of Example 3, and applying $C_8F_{17}SO_2N(C_3H_7)CH_2COOK$ to the second protective layer such that the amount was 15 mg/m². When Sample No. 302 was processed in a format as depicted on FIG. 5 of JP-A-4-62543, and the tests similar to those of Sample Nos. 101 and 106 of Example 3 were carried out, the effects of the present invention similar to Example 3 were obtained.

EXAMPLE 6

Sample No. 101 was cut into 35 mm width, photographed by a camera, and the following processing was carried out for 15 days using 1 m² of the photographed photosensitive material per day (Running processing).

An automatic developing machine, FP-560B, produced by Fuji Film Co., Ltd. was used in each processing as follows. The alternation had been made that the overflow solution from the bleaching bath was not run into the post-bath and all of the overflow solution was discharged into a waste liquid tank.

The processing stages and the processing compositions were as follows:

|  | Processing Period | Processing Temp. | Replenishing amount*¹ | Tank volume |
|---|---|---|---|---|
| Color developing | 3'5" | 37.6° C. | 15 ml | 17 l |
| Bleaching | 50" | 38.0° C. | 5 ml | 5 l |
| Fixing (1) | 50" | 38.0° C. | — | 5 l |
| Fixing (2) | 50" | 38.0° C. | 8 ml | 5 l |
| Water washing | 30" | 38.0° C. | 17 ml | 3.5 l |
| Stabilization (1) | 20" | 38.0° C. | — | 3 l |
| Stabilization (2) | 20" | 38.0° C. | 15 ml | 3 l |
| Drying | 1'30" | 60° C. |  |  |

*The replenishing amount was an amount per 35 mm width and 1.1 m length of the photosensitive material (corresponding to one 24 Ex.)

The stabilizing solution and the fixing solution were a countercurrent manner from (2) to (1), and all of the overflow solutions of the washing water were introduced into the fixing (2). The carrying over amounts of the color developer to the bleaching stage, of the bleaching solution to the fixing stage (1), of the fixing solution to the fixing stage (2), and of the fixing solution to the waster washing stage were 2.5 ml, 2.0 ml, 2.0 ml, and 2.0 ml, respectively, per 35 mm width and 1.1 m length of the photosensitive material. All of the crossover periods were 6 seconds, and the crossover periods were included in the previous processing stages.

The opening area of the processing machine was 120 cm² in the color developer, 120 cm² in the bleaching solutions, and approximately 100 cm² in the other processing solutions.

The compositions of the processing solutions were as follows:

|  | Tank Solution (g) | Replenishing Solution (g) |
|---|---|---|
| (Color Developer) |  |  |
| Diethyltriamine pentaacetic acid | 2.2 | 2.2 |
| Disodium catechol-3,5-disulfonate | 0.3 | 0.3 |
| 1-Hydroxyethylidene-1,1-disulfonic acid | 2.0 | 2.0 |
| Sodium sulfite | 3.9 | 5.5 |
| Potassium carbonate | 37.5 | 39.0 |
| Disodium N,N-bis(2-sulfoethyl)hydroxylamine | 2.0 | 2.0 |
| Potassium bromide | 1.4 | - |
| Potassium iodide | 1.3 mg | - |
| Hydroxylamine sulfate | 2.4 | 3.6 |
| 2-Methyl-[N-ethyl-N-(β-hydroxyethyl)amino]aniline sulfate | 4.5 | 6.8 |
| Water to make | 1.0 l | 1.0 l |
| pH (adjusted with potassium hydroxide and sulfuric acid) | 10.05 | 10.21 |
| (Bleaching Solution) |  |  |
| Chelating agent 10 according to the present invention | 0.18 mol | 0.27 mol |
| Ferric nitrate.nonahydrate | 0.16 mol | 0.24 mol |
| Ammonium bromide | 70 | 105 |
| Glutaric acid | 93 | 140 |
| Water to make | 1.0 l | 1.0 l |
| pH (adjusted with an aqueous ammonia) | 4.6 | 4.2 |

(Fixing (1) Tank Solution)

The mixed solution of the above bleaching solution and the following fixing tank solution in a mixing ratio of 7 to 93 (volume ratio). (pH 7.0)

|  | Tank Solution (g) | Replenishing Solution (g) |
|---|---|---|
| (Fixing Solution) |  |  |
| Ammonium sulfite | 19 | 57 |
| An aqueous ammonium thiosulfate solution (700 g/l) | 280 ml | 840 ml |
| Imidazole | 15 | 45 |
| Ammonium metanethiosulfonate | 40 | 120 |
| Ethylenediaminetetraacetic acid | 15 | 45 |
| Water to make | 1.0 l | 1.0 l |
| pH (adjusted with an aqueous ammonia and acetic acid) | 7.4 | 7.45 |
| (Washing Water) |  |  |
| the same as Example 3. |  |  |

(Stabilizing Solution) the same as Example 3.

After the running processing, when the amount of the remaining silver at the portion of the highest density was determined in the same manner as in Example 3, it was found to be 4.2 mg/cm², indicating good desilvering property.

EXAMPLE 7

The time elapse test (1 weeks) was carried out at 25° C. using the bleach-fixing tank solution in Example 3 without passing through any photosensitive material to observe the filter blockage. The results are shown in Table 5.

TABLE 5

| No. | Chelating agent | Filter blockage | Remarks |
|---|---|---|---|
| 401 | Comparative compound B | D | Comparative |
| 402 | Comparative compound C | C | Comparative |
| 403 | Comparative compound D | C | Comparative |
| 404 | Exemplified compound 1 | A | Inventive |
| 405 | Exemplified compound 6 | A | Inventive |
| 406 | Exemplified compound 7 | A | Inventive |
| 407 | Exemplified compound 8 | A | Inventive |
| 408 | Exemplified compound 9 | A | Inventive |
| 409 | Exemplified compound 10 | A | Inventive |
| 410 | Exemplified compound 12 | A | Inventive |
| 411 | Exemplified compound 16 | A | Inventive |
| 412 | Exemplified compound 17 | A | Inventive |
| 413 | Exemplified compound 21 | B | Inventive |
| 414 | Exemplified compound 35 | A | Inventive |
| 415 | Exemplified compound 36 | A | Inventive |
| 416 | Exemplified compound 42 | A | Inventive |
| 417 | Exemplified compound 43 | A | Inventive |
| 418 | Exemplified compound 44 | A | Inventive |
| 419 | Exemplified compound 49 | A | Inventive |

Comparative compounds B, C, and D were the same as those of Example 3, the criteria for evaluating the filter blockage were also the same as those of Example 3. It was understood that the bleach-fixing compositions of the present invention were of significance in terms of the filter blockage with time elapse over the comparative compounds.

EXAMPLE 8

Sample No. 601 of a multi-layered color photosensitive material (color positive film) was produced by applying a photosensitive layers described from page 96, the left column, line 20 to page 114 of Kogiho No. 94-6023 (published from Japan Patent Association) on a cellulose triacetate film support with a subbing layer.

Sample No. 601 was applied to continuous gradation wedge exposure at a color temperature of 4800 K, and to a running processing in the following processing stages using the following processing solutions with a cinematic automatic developing machine (until the accumulative replenishing amount was three times the volume of the tank).

In the bleach-fixing solution, silver was removed inline using a silver-recovering apparatus, part of the overflow from the silver-recovering apparatus was discharged as a wasted liquid, and the remaining was regenerated to be reused as a replenishing solution for the bleach-fixing solution. The silver-recovering apparatus used was a small-size electrolytic silver-recovering apparatus having an anode composed of carbon and a cathode composed of stainless steel at a current density and was operated at a current density of 0.5 A/dm². The schematic view of the silver-recovering system is depicted on FIG. 1 of JP-A-6-175305. To be specific, the overflow of the bleach-fixing tank was directly connected to the silver-recovering apparatus, part of overflow was returned to the original bleach-fixing tank at 100 ml/minute through a filter by means of pump 1. The overflow from the silver-recovering apparatus was recovered in a regenerating tank in an amount of 300 ml per liter of the overflow, and when the recovered amount was 1 liter, air was blown for about 2 hours, after which a regenerating agent was added which was transferred to a replenishing tank for bleach-fixing tank by means of pump 2. The remaining solution (100 ml) was discharged as a wasted liquid. An amount of the wasted liquid was 220 ml per m² of Sample No. 601.

In the water washing, a 5-stage multi-room washing tank was used in a horizontal arrangement, and countercurrent cascade was carried out. Typically, one described in FIG. 1 of JP-A-66540 was used.

The overflow solution of the first washing water $W_1$ was cascaded to the bleach-fixing tank, which was the pre-bath. A reverse osmosis (RO) apparatus, RC 30, (produced by Fuji Photo Film Co., Ltd.) was provided between the fourth washing water $W_4$ and the fifth washing water $W_5$. That is, the washing water taken from $W_4$ was applied to the RO apparatus, the concentrate was returned to $W_4$, and the transmitted solution was returned to $W_4$. The processing stages were as follows. The outline of the processing apparatus is depicted on FIG. 2 of JP-A-6-175305.

| | Processing Stage | | | |
|---|---|---|---|---|
| | Processing Period | Processing Temp. | Replenishing amount*¹ | Tank volume (l) |
| Color developing | 1'00" | 45° C. | 260 ml | 2 |
| Bleach-fixation | 1'00" | 40° C. | 200 ml | 2 |
| Water washing (1) | 15" | 40° C. | — | 0.5 |
| Water washing (2) | 15" | 40° C. | — | 0.5 |
| Water washing (3) | 15" | 40° C. | — | 0.5 |
| Water washing (4) | 15" | 40° C. | — | 0.5 |
| Water washing (5) | 15" | 40° C. | 104 ml | 0.5 |
| Stabilization | 2" | R.T. | 30 ml | Coating |
| Drying | 50" | 70° C. | — | — |

*¹The replenishing amount was an amount per 1 m² of the photosensitive material.

The crossover period from the color developing to the bleach-fixation and from bleach-fixation to water washing (1) was 3 minutes. An average carrying over amount per m² of the photosensitive material was 65 ml.

In each tank, for the adjustment of distillation, the temperature and humidity out of the processing machine were detected by a thermo/humidity meter as described in JP-A-3-280042 to calculate the amount of the distillation which was adjusted. The following ion exchanged water for water washing was used as the water for adjusting distillation.

In order to clarify the achieved level for the problem to be solved by the compound of the present invention, states where the pH of the color developer was changed were forcedly prepared. To be specific, the tests were carried out in the case of increasing the pH value to 0.2 (pH: 10.25) and in the case of decreasing the pH value to 0.2 (pH: 9.85).

The compositions of the processing solutions were as follows:

| (Color Developer) | | |
|---|---|---|
| | Mother Solution (g) | Replenishing Solution (g) |
| Diethyltriaminepentaacetic acid | 4.0 | 4.0 |
| Chelating agent (Compound described in Table 6) | 0.01 mol | 0.01 mol |
| Sodium sulfite | 4.0 | 6.0 |
| Potassium carbonate | 40.0 | 40.0 |
| Potassium bromide | 2.0 | — |
| Potassium iodide | 1.3 mg | — |
| 4-Hydroxy-6-methyl-1,3,3a,7-tetrazaindene | 0.14 | — |
| Disodium-N,N-bis(sulfonato-ethyl)hydroxylamine | 13.2 | 17.2 |
| 2-Methyl-4-[N-ethyl-N-(β-hydroxyethyl)amino]aniline sulfate | 11.0 | 14.5 |
| Water to make | 1.0 l | 1.0 l |
| pH (adjusted with potassium hydroxide and sulfuric acid) | 10.25 or 9.85 | 10.50 or 10.10 |

| (Bleach-fixing Solution) | | |
|---|---|---|
| | Mother Solution (mol) | Replenishing Solution at starting (mol) |
| Ammonium 2-{[1-(carboxyethyl)-carboxymethylamino]-ethyl}-carboxymethylaminobenzoato ferrate monohydrate | 0.08 | 0.13 |
| Ammonium ethylenediaminetetraacetato ferrate dihydrate | 0.10 | 0.17 |
| An aqueous ammonium thiosulfate solution (700 g/l) | 300 ml | 495 ml |
| Ammonium iodide | 2.0 g | — |
| Ammonium sulfite | 0.10 | 0.17 |
| Methacarboxybenzenesulfonic acid | 0.05 | 0.09 |
| Succinic acid | 0.10 | 0.17 |
| Water to make | 1.0 l | 1.0 l |
| pH (adjusted with nitric acid and an aqueous ammonia) | 6.0 | 5.5 |

| (Regenerating Agent for Bleach-fixing Solution) | |
|---|---|
| | Amount of the addition per liter of recovering solution for regeneration (mol) |
| Ammonium 2-{[1-(carboxyethyl)-carboxymethylamino]-ethyl}-carboxymethylaminobenzoato ferrate monohydrate | 0.05 |
| Ammonium ethylenediaminetetraacetato ferrate dihydrate | 0.07 |
| An aqueous ammonium thiosulfate solution (700 g/l) | 195 mg |
| Ammonium sulfite | 0.07 |
| Metacarboxybenzene sulfinic acid | 0.04 |
| Succinic acid | 0.07 |

(Washing Water)

Common to the mother solution and replenishing solution.

Tap water was passed through a mixed bed type column filled with an H type strongly acidic cation exchange resin (Amberite IR-120B, produced by Rohm & Haas) and an OH type strongly basic anion exchange resin (Amberite IRA-400, produced by Rohm & Haas ) to reduce calcium and magnesium ion concentration to be not more than 3 mg/l, and then 20 mg/l of sodium dichloroisocyanurate and 150 mg/l of sodium sulfate were added. The pH of this solution was from 6.5 to 7.5.

| (Stabilizing Solution) for Coating | (Unit: g) |
|---|---|
| Sodium p-toluenesulfonic acid | 0.03 |
| Polyoxyethylene-p-mononoylphenyl ether (Average polymerization degree: 10) | 0.2 |
| Disodium ethylenediaminetetraacetate | 0.05 |
| 1,2,4-Triazole | 1.3 |
| 1,4-Bis(1,2,4-triazol-1-ylmethyl)-piperidine | 0.75 |
| Water to make | 1.0 l |
| pH | 5.0–8.0 |

The residual rates of the developing agent and of hydroxylamine after the running processing were analyzed. Furthermore, the presence or absence of precipitation in the solution of the color developer having pH 10.25 after the running processing was visibly determined. These results are summarized in Table 6.

TABLE 6

| No. | Chelating agent | Residual amount of developing agent pH 10.25 | Residual amount of developing agent pH 9.85 | Residual amount hydroxylamine pH 10.25 | Residual amount hydroxylamine pH 9.85 | Precipitation | Remarks |
|---|---|---|---|---|---|---|---|
| 501 | None | 39% | 52% | 34% | 48% | xxx | Comparative |
| 502 | Diethylenetriamine-pentaacetic acid | 42% | 60% | 38% | 55% | x | Comparative |
| 504 | 1-Hydroxyethylidene-1,1-diphosphonic acid | 59% | 71% | 54% | 68% | o | Comparative |
| 505 | Ethylenediamine diacetic acid dipropionic acid | 41% | 57% | 37% | 52% | x | Comparative |
| 506 | Exemplified compound 2 | 75% | 77% | 68% | 72% | o | Inventive |
| 509 | Exemplified compound 7 | 83% | 86% | 81% | 85% | o | Inventive |
| 510 | Exemplified compound 8 | 84% | 86% | 81% | 86% | o | Inventive |
| 512 | Exemplified compound 10 | 74% | 75% | 64% | 70% | o | Inventive |
| 513 | Exemplified compound 11 | 83% | 84% | 78% | 79% | o | Inventive |
| 515 | Exemplified compound 13 | 71% | 75% | 70% | 74% | o | Inventive |
| 516 | Exemplified compound 16 | 77% | 78% | 72% | 76% | o | Inventive |
| 517 | Exemplified compound 20 | 77% | 80% | 77% | 80% | o | Inventive |
| 518 | Exemplified compound 34 | 68% | 72% | 68% | 72% | o | Inventive |
| 522 | Exemplified compound 42 | 75% | 79% | 75% | 76% | o | Inventive |
| 523 | Exemplified compound 43 | 69% | 72% | 71% | 72% | o | Inventive | o: No precipitate existed
x: The higher the number, more the generation of precipitation in the solution.

As is clear from Table 6, no sufficient effect was sometimes obtained when no cheleate compound was added or when the conventional cheleating agent was added by the variation of pH. It was understood that such an effect could be obtained only by the addition of the compound of the present invention.

EXAMPLE 9

Sample No. 702 described below was processed in the same processing stages and processing solutions as in Example 3 using a cinematic automatic developing machine, and the same evaluation as in Example 3 was carried out.

(1) Quality of Material of Support, etc.

The support used in the present invention was produced by the following process.

PEN:

After 100 parts by weight of commercially available poly(ethylene-2,6-naphthalate) polymer and 2 parts of Tinuvin P.326 (produced by Gaigy) as a ultraviolet absorber were dried according to the conventional process, the mixture was melted at 300° C., extruded from a T die, stretched by 330% at 140° C. in the machine direction, and stretched by 330% at 130° C. in the transverse direction, and then thermally fixed at 250° C. for 6 minutes. The glass transition temperature was found to be 120° C.

(2) Coating of Subbing Layer

After both surfaces of the support had been subjected to a corona discharge treatment, a subbing layer coating solution having the following composition was applied to provide a subbing layer on the face residing on the a high temperature side when being stretched. The corona discharge treatment was carried out using Solid state corona discharger, Model 6 KVA, produced from Pillar Inc. which treated a 30 cm width support at 20 m/min. Form the read values of current and voltage, the support to be treated was treated at 0.375 KV.A.min/m². The discharge frequency during the course of the treatment was 9.6 KHz and the gap clearance between the electrode and dielectric substance was 1.6 mm.

| | |
|---|---|
| Gelatine | 3 g |
| Distilled water | 250 ml |
| Sodium α-sulfodi-2-ethylhexyl succinate | 0.05 g |
| Formaldehyde | 0.02 g |

On the support, TAC, a subbing layer having the following composition was provided.

| | |
|---|---|
| Gelatine | 0.2 g |
| Salicylic acid | 0.1 g |
| Methanol | 15 ml |
| Acetone | 85 ml |
| Formaldehyde | 0.01 g |

(3) Coating of Backing Layer

On one side of the support with subbing layer produced under (2) the following first to third backing layers were applied.

a) First Backing Layer

| | |
|---|---|
| Fine Co-containing needle-form γ-iron oxide grain (incorporated as a gelatine dispersion; average grain size: 0.08 μm) | 0.2 g/m² |
| Gelatine | 3 g/m² |
| The following compound $(CH_2=CHSO_2NHCH_2CH_2NH)_2CO$ | 0.1 g/m² |
| The following compound | 0.02 g/m² |

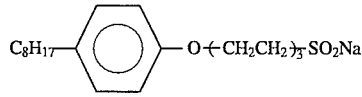

-continued

| | |
|---|---|
| Poly(ethyl acrylate) (average diameter: 0.08 μm) | 1 g/m² |
| b) Second Backing Layer | |
| Gelatine | 0.05 g/m² |
| Electric conductive material [SnO₂/Sb₂O₃ ((:1), grain size: 0.15 μm) | 0.16 g/m² |
| Sodium dodecylbenzenesulfate | 0.05 g/m² |
| c) Third Backing Layer | |
| Gelatine | 0.5 g/m² |
| Polymethyl methacrylate (average grain size: 1.5 μm) | 0.02 g/m² |
| Cetyl stearate (dispersing sodium dodecylbenzenesufonate) | 0.01 g/m² |
| Sodium di(2-ethylhexyl)sulfosuccinate | 0.01 g/m² |
| The following compound | 0.01 g/m² |

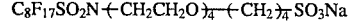

$$C_8F_{17}SO_2N(-CH_2CH_2O\overline{)_4}(-CH_2\overline{)_3}SO_3Na$$

with $C_3H_7$ substituent on N.

The resulting back layers had a coercive force of 960 e.

(4) Heat Treatment of Support

After the subbing layer and backing layers were applied as described above, dried and rolled, a heat treatment was carried out at 110° C. for 48 hours.

(5) Production of Photosensitive Layer

Sample No. 702 of a multi-layered color photosensitive material was produced by applying a photosensitive layers described from page 116, the left column, line 17 to page 133 of Kogiho No. 94-6023 (published from Japan Patent Association) on the portion opposite to the backing layer obtained as described above.

The sensitive material produced as described above was cut into a size of 24 mm (width)×160 cm, and two 2 mm square perforations were provided on the position 0.7 mm form a wide direction of one side of the length direction of the sensitive material at 5.8 mm interval. A sample having the two sets provided at an interval of 32 mm was produced and stored in a plastic-made film cartridge as explained in FIG. 1 to FIG. 7 of U.S. Pat. No. 5,296,887.

Sample No. 702 was processed and evaluated as described in Example 3 of the present invention. The exposed and processed Sample No. 702 was again stored in the original plastic-made film cartridge.

Similar to the results of Example 8, good results were obtained in the present invention even in the case of the photosensitive material having a magnetically recording layer on the back surface opposite to the emulsion layer.

EXAMPLE 10

The color paper of Sample No. 001 of Example 4 of JP-A-5-303186 was used to be processed with the following processing solutions in the following processing process.

In order to clarify the achieved level for the problem to be solved by the compound of the present invention, states where the pH of the color developer was changed were forcedly prepared. To be specific, the tests were carried out in the case of increasing the pH value to 0.2 (pH: 10.25) and in the case of decreasing the pH value to 0.2 (pH: 9.85).

| (Color Developer) | |
|---|---|
| Water | 700 ml |
| Disodium 1,2-dihydroxybenzene-4,6-disulfonate | 4.0 g |
| Triethanolamine | 12.0 g |

-continued

| (Color Developer) | |
|---|---|
| Potassium chloride | 1.5 g |
| Potassium bromide | 0.01 g |
| Potassium carbonate | 27.0 g |
| Diaminosutilbene brightening agent (WHITEX 4, produced by Sumitomo Chemicals) | 1.0 g |
| Sodium sulfite | 0.1 g |
| Disodium-N,N-bis(sulfonateethyl)-hydroxylamine | 10.0 g |
| N-ethyl-N-(β-methanesulfonamido-ethyl)-3-methyl-4-aminoaniline sulfate | 5.0 g |
| Water to make | 1000 ml |
| pH (25° C.) | 10.25 or 9.85 |

The color developer as described above was designated Sample No. 801 and those further containing, thereto, the compound of the present invention or comparative compound in an amount as shown in Table 7 were designated Sample Nos. 802 to 810, respectively.

| (Bleach-fixing Solution) | |
|---|---|
| Water | 600 ml |
| Ammonium thiosulfate (700 g/l) | 100 ml |
| Ammonium sulfite | 40 g |
| Ammonium ethylenediaminetetraacetato ferrate | 55 g |
| Ethylenediaminetetraacetic acid | 5 g |
| Ammonium bromide | 40 g |
| Nitric acid (67%) | 30 g |
| Water to make | 1000 ml |
| pH (25° C.) (adjusted with acetic acid and an aqueous ammonia) | 5.8 |

[Rinsing Solution]

Ion exhanged water (contents of calcium and magnesium: not more than 3 ppm, respectively)

To the color developer described above were added 5 ppm of ferric ion and 150 ppm of calcium ion, and the mixture was left standing in a beaker having an opening rate of 0.10 cm⁻¹ at 38° C. for 20 days.

The color photosensitive material as described above was subjected to gradation exposure of three color separation filter for sensitometry using a sensitometer (Type FWH, produced by Fuji Photo Film Co., Ltd.). The exposure was carried out so that an amount of exposure was 250 CMS for an exposure period of 0.1 second.

After the exposure, the color developer immediately after the prepared (fresh solution) and the color developer after the elapse of time (time elapsed solution) were used to process the photosensitive material according to the following stages.

| | Processing Stage | | | |
|---|---|---|---|---|
| | Temp. | Period | Replenishing amount | Tank volume |
| Color developing | 35° C. | 45" | 161 ml | 17 l |
| Bleach-fixation | 35° C. | 45" | 215 ml | 17 l |
| Rinsing (1) | 35° C. | 20" | — | 10 l |
| Rinsing (2) | 35° C. | 20" | — | 10 l |
| Rinsing (3) | 35° C. | 20" | 360 ml | 10 l |
| Drying | 80° C. | 60" | | |

*¹The replenishing amount was an amount per 1 m² of the photosensitive material.

The amount of the developing agent remaining in the time elapsed solution was quantitatively determined by a high performance liquid chromatography. The presence or absence of precipitation in the color developer after the elapse of time was observed. The results are summarized in Table 7.

To the color developer described above were added 5 ppm of ferric chloride as a ferric ion and 150 ppm of calcium nitrate as a calcium ion to prepare Sample Nos. 901–913. In a hard vinyl chloride-made container having a length of 10 cm, a width of 25 cm, and the depth of 30 cm was placed 5 l of each sample, and a time elapse test was carried out at a

TABLE 7

| No. | Chelating agent (Amount) | Residual amount of main developing agent (%) | | Formation of precipitation | Remarks |
| --- | --- | --- | --- | --- | --- |
| | | pH 10.25 | pH 9.85 | | |
| 801 | None | 51 | 68 | xxx | Comparative |
| 802 | Sodium hexametaphosphate (1 g/l) | 70 | 82 | xx | Comparative |
| 803 | 1-Hydroxyethylidene-1,1-diphosphonic acid (60%) (1.6 g/l) | 72 | 85 | xx | Comparative |
| 804 | Ethylenediaminetetraacetic acid (1 g/l) | 60 | 71 | o | Comparative |
| 805 | Ethylenediaminediacetic acid dipropionic acid (1 g/l) | 57 | 69 | x | Comparative |
| 806 | Exemplified compound 2 (1 g/l) | 81 | 85 | o | Inventive |
| 807 | Exemplified compound 8 (1 g/l) | 85 | 91 | o | Inventive |
| 808 | Exemplified compound 10 (1 g/l) | 83 | 89 | o | Inventive |
| 809 | Exemplified compound 42 (1 g/l) | 81 | 84 | o | Inventive |
| 810 | Exemplified compound 43 (1 g/l) | 80 | 82 | o | Inventive | o: No formation of precipitate
x: Formation of precipitate (The higher the number, more the generation of precipitation in the solution.)

As is clear from Table 7, no sufficient effect was sometimes obtained when no chelate compound was added or when the conventional chelating agent was added by the variation of pH. However, when the compound of the present invention was added, it was understood that the amount of the developing agent remained in an amount for obtaining a sufficient ability. Moreover, with regard to the generation of precipitate, the compound of the present invention was found to be drastically improved in comparison with Comparative Example.

Particularly, in the case of one conventional compound, whereas an effect for preventing the formation of precipitate was great, the preserving property was poor, and in the other conventional compound, whereas the decomposition of the developing agent is small, the prevention of the formation of precipitation was insufficient.

In contrast, it was proved that the compound of the present invention provided a stable color developer without formation of precipitate.

EXAMPLE 11

The following processing solution was prepared.

| (Color Developer) | (Unit: g) |
| --- | --- |
| Diethyltriaminepentaacetic acid | 1.0 |
| Chelating agent (Compound described in Table 8) | 0.01 mol |
| Sodium sulfite | 4.0 |
| Potassium carbonate | 30.0 |
| Potassium bromide | 1.4 |
| Potassium iodide | 1.5 mg |
| Hydroxyethylamine sulfate | 2.4 |
| 4-(N-ethyl-N-β-hydroxyethylamino)-2-methylaniline sulfate | 4.5 |
| Water to make | 1000 ml |
| pH | 10.05 | conditioned temperature of 38° C. for 30 days while continuously circulating the solution in the container by a pump at a rate of 3 l/minute.

To this container was provided a floating cap which covered 200 cm² of the solution surface, and an air-opened solution surface was 50 cm².

Subsequently, Sample No. 101 of Example 1 of JP-A-4-274236 was cut into 35 mm width, applied to a 5 CMS wedge exposure at a color temperature of 4800 K. This was processed with Sample Nos. 901-913 immediately after the preparation (fresh solution) or after the time elapse test as a developer in the following processing stages.

| Processing Stage | | |
| --- | --- | --- |
| | Processing period | Processing temp. |
| Color developing | 3'5" | 38.0° C. |
| Bleaching | 50" | 38.0° C. |
| Fixing | 1'40" | 38.0° C. |
| Water washing (1) | 30" | 38.0° C. |
| Water washing (2) | 20" | 38.0° C. |
| Stabilization | 20" | 38.0° C. |

| | (Unit: g) |
| --- | --- |
| (Bleaching Solution) | |
| Ammonium 1,3-propanediaminetetraacetato ferrate | 0.55 mol |
| Ammonium brimide | 85 |
| Ammonium nitrate | 20 |
| Glycolic acid | 55 |
| Water to make | 1000 ml |
| pH | 4.2 |
| (Fixing Solution) | |
| Secondary ammonium ethylenediaminetetraacetate | 1.7 |
| Ammonium sulfite | 14.0 |

-continued

| Processing Stage | |
| --- | --- |
| Aqueous ammonium thiosulfate solution (700 g/l) | 260.0 ml |
| Water to make | 1000 ml |
| pH | 7.0 |

(Washing Water)

Tap water was passed through a mixed bed type column filled with an H type strongly acidic cation exchange resin (Amberite IR-120B, produced by Rohm & Haas) and an OH type strongly basic anion exchange resin (Amberite IRA-400, produced by Rohm & Haas) to reduce calcium and magnesium ion concentration to be not more than 3 mg/l, and then 20 mg/l of sodium dichloroisocyanurate and 150 mg/l of sodium sulfate were added. The pH of this solution was from 6.5 to 7.5.

| (Stabilizing Solution) | (Unit: g) |
| --- | --- |
| Sodium p-toluenesulfonate | 0.03 |
| Polyoxyethylene-p-monononylphenyl ether (Average polymerization degree: 10) | 0.2 |
| Disodium ethylenediaminetetraacetate | 0.05 |
| 1,2,4-Triazole | 1.3 |
| 1,4-Bis(1,2,4-triazol-1-ylmethyl)-piperidine | 0.75 |
| Water to make | 1000 ml |
| pH | 8.5 |

At an exposure amount that the B density determined with a blue light (B-light) was 2.5 when processed with the fresh solution, the B density obtained from the solution after the time elapse test was determined by an X light 310 type photographic densitometer to obtain the difference from that of the fresh solution, $\Delta D_B$. The residual rates of the developing agent and of hydroxylamine after the time elapse were analyzed. Furthermore, the presence or absence of precipitation in the color developing solution after the time elapse was visibly determined. These results are summarized in Table 8.

As is clear from Table 8, it was understood that when the conventional chelating agent was added, the prevention of the formation of precipitation and the securing the solution stability were at insufficient levels, but the addition of the compound of the present invention gave a great effect.

EXAMPLE 12

To the fixer of Example 11 was added 3 g/l of Compound 1, 2, 4, 7, 8, 11, 12, 20, 34 or 44 according to the present invention, and was further added an amount of ferric ion corresponding to the carrying over amount from the bleaching solution which was pre-bath to prepare Sample Nos. 1001 to 1010. These samples were left standing at an opening pore rate of 0.1 cm$^{-1}$ at 38° C. for 30 days, and the muddiness of the solution was observed. In the samples having no compound added, remarkable muddiness took place, but the fixers having a compound according to the present invention being added maintained their transparent states, indicating that no precipitate was generated.

EXAMPLE 13

The stabilizing solution of Example 11 itself was designated as Sample No. 1101 for comparison and 100 mg/l of the exemplified compounds 1, 2, 6, 8, 10, 16, 35, 43, 44 or 46 was added to the stabilizing solution to prepare Sample Nos. 1102–1111. Using these stabilizing solutions and fresh solutions of color developer Sample No. 901 of Example 11, etc., Sample No. 101 of the multi-layer color negative photosensitive material was processed in the process as described in Example 11. Sample No. 101 of the multi-layered color negative photosensitive material after the processing was left standing at 45° C. and at 70% relative humidity over a period of 1 week, and an increase in the staining of magenta ($\Delta D_{min}$) was determined.

The results are shown in Table 9.

TABLE 9

| No. | Chelating agent | $\Delta D_{min}$ | Remarks |
| --- | --- | --- | --- |
| 1101 | None | 0.25 | Comparative |
| 1102 | Exemplified Compound 1 | 0.09 | Inventive |
| 1103 | Exemplified Compound 2 | 0.08 | Inventive |

TABLE 8

| No. | Chelating agent | $\Delta D_{max}$ | Residual rate of developing agent | Residual rate of hydroxylamine** | Precipitation |
| --- | --- | --- | --- | --- | --- |
| 901 | None | −0.5 | 60% | 20% | BBB |
| 902 | Ethylenediaminetetraacetic acid | −0.4 | 62% | 30% | G |
| 903 | Ethylenediaminetetra-methylenephosphonic acid | −0.05 | 88% | 70% | B |
| 904 | Exemplified compound 1 | −0.04 | 90% | 75% | G |
| 905 | Exemplified compound 2 | −0.05 | 91% | 77% | G |
| 906 | Exemplified compound 6 | −0.04 | 92% | 76% | G |
| 907 | Exemplified compound 12 | −0.05 | 83% | 71% | G |
| 908 | Exemplified compound 13 | −0.08 | 80% | 68% | G |
| 909 | Exemplified compound 20 | −0.06 | 82% | 69% | G |
| 910 | Exemplified compound 34 | −0.07 | 84% | 71% | G |
| 911 | Exemplified compound 36 | −0.06 | 84% | 70% | G |
| 912 | Exemplified compound 42 | −0.07 | 87% | 73% | G |
| 913 | Exemplified compound 44 | −0.08 | 88% | 74% | G |

G: No precipitate existed
B: The higher the number, more the generation of precipitation in the solution.
**After oxidized with iodine, sulfanic acid and α-naphtylamine were added to be colored (red), and then a rate was spectrometrically obtained.

TABLE 9-continued

| No. | Chelating agent | ΔD$_{min}$ | Remarks |
|---|---|---|---|
| 1104 | Exemplified Compound 6 | 0.10 | Inventive |
| 1105 | Exemplified Compound 8 | 0.08 | Inventive |
| 1106 | Exemplified Compound 10 | 0.08 | Inventive |
| 1107 | Exemplified Compound 16 | 0.11 | Inventive |
| 1108 | Exemplified Compound 35 | 0.12 | Inventive |
| 1109 | Exemplified Compound 43 | 0.13 | Inventive |
| 1110 | Exemplified Compound 44 | 0.11 | Inventive |
| 1111 | Exemplified Compound 46 | 0.11 | Inventive |

It was understood that the stabilizing solution of the present invention having the compound according to the present invention suppressed an increase in staining, thereby enhancing the image storage ability.

While the invention has been described in detail and with reference to specific embodiments thereof, it will be apparent to one skilled in the art that various changes and modifications can be made therein without departing from the spirit and scope thereof.

What is claimed is:

1. A process for processing a silver halide photosensitive material, comprising the step of processing an imagewise exposed and developed silver halide photosensitive material in the presence of a compound represented by formula (I) or a metal chelate compound thereof,

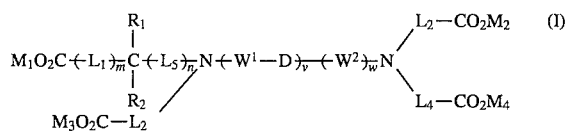

wherein $R_1$ is an aliphatic hydrocarbon group, an aryl group, or a heterocyclic ring group;

$R_2$ is hydrogen, an aliphatic hydrocarbon group, an aryl group, or a heterocyclic ring group;

$L_1$, $L_2$, $L_3$, $L_4$ and $L_5$ are independently an alkylene group;

m and n are independently 0 or 1;

$W^1$ and $W^2$ are independently an alkylene group, an arylene group, aralkylene group or a divalent nitrogen-containing heterocyclic ring group;

D is a single bond, —O—, —S— or —N($R_w$)—, where $R_2$ is hydrogen, an aliphatic hydrocarbon group or an aryl group;

v is 0 or an integer or from 1 to 3;

w is an integer of from 1 to 3; and $M_1$, $M_2$, $M_3$ and $M_4$ are independently hydrogen or a cation.

2. The process according to claim 1, wherein said compound represented by formula (I) is represented by formula (II):

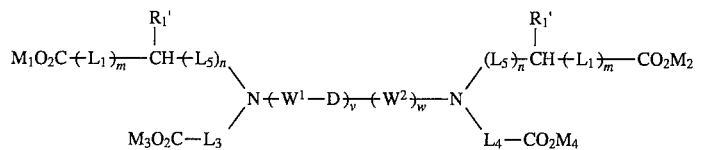

wherein $R_1'$ is an aliphatic hydrocarbon group;

$L_1$, $L_3$, $L_4$ and $L_5$ are independently an alkylene group;

m and n are independently 0 or 1;

$W^1$ and $W^2$ are independently an alkylene group, an arylene group, aralkylene group or a divalent nitrogen-containing heterocyclic ring group;

D is a single bond, —O—, —S— or —N($R_w$)—, where $R_w$ is hydrogen, an aliphatic hydrocarbon group or an aryl group;

v is 0 or an integer of from 1 to 3;

w is an integer of from 1 to 3; and $M_1$, $M_2$, $M_3$ and $M_4$ are independently hydrogen or a cation.

3. The process according to claim 1, wherein said compound represented by formula (I) is represented by formula (III):

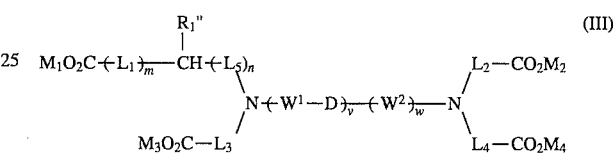

wherein $R_1''$ is an aryl group;

$L_1$, $L_2$, $L_3$, $L_4$ and $L_5$ are independently an alkylene group;

m and n are independently 0 or 1;

$W^1$ and $W^2$ are independently an alkylene group, an arylene group, aralkylene group or a divalent nitrogen-containing heterocyclic ring group;

D is a single bond, —O—, —S— or —N($R_w$)—, where $R_w$ is hydrogen, an aliphatic hydrocarbon group or an aryl group;

v is 0 or an integer of from 1 to 3;

w is an integer of from 1 to 3; and $M_1$, $M_2$, $M_3$ and $M_4$ are independently hydrogen or a cation.

4. The process according to claim 1, wherein said metal chelate compound is represented by formula (I-a):

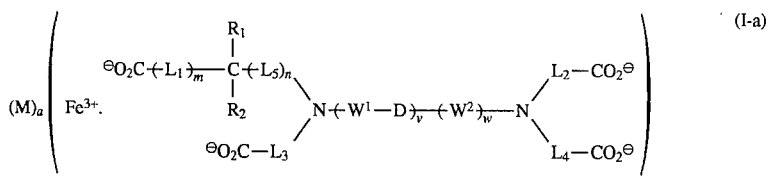

wherein $R_1$, $R_2$, $L_1$, $L_2$, $L_3$, $L_4$, $L_5$, m, n, $W^1$, $W^2$, D, v and w have the same meanings as those in formula (I), M is hydrogen or a cation, and a is a number defined so that the iron complex becomes neutral.

5. The process according to claim 1, wherein said metal chelate compound is represented by formula (I-d) or (I-e):

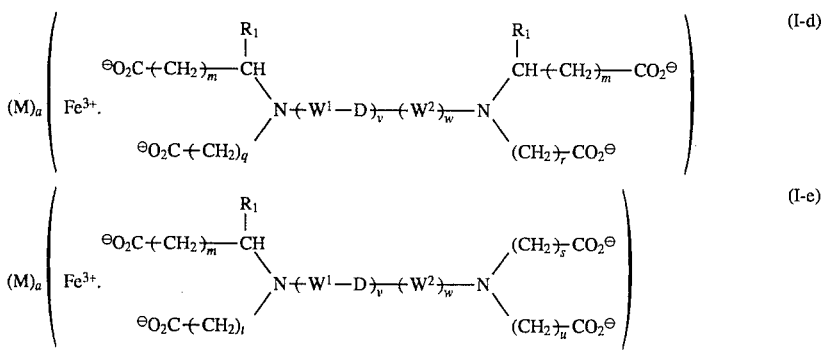

wherein $R_1$, m, $W^1$, $W^2$, D, v and w have the same meanings as those in formula (I), M is hydrogen or a cation, a is a number defined so that the iron complex becomes neutral, and q, r, s, t, and u are independently 1 or 2.

6. The process according to claim 5, wherein $R_1$ represents an alkyl group having 1 to 7 carbon atoms or a phenyl group.

* * * * *